(12) United States Patent
Roe et al.

(10) Patent No.: US 12,214,110 B2
(45) Date of Patent: Feb. 4, 2025

(54) ANTIMICROBIAL SYSTEM WITH DISTRIBUTED DISINFECTION CONTROLS, INTEGRATED ARMING SWITCH SENSORS, AND STREAMLINED SAFE LOCKOUT PROTOCOL

(71) Applicant: ABL IP HOLDING LLC, Conyers, GA (US)

(72) Inventors: Steven T. Roe, Atlanta, GA (US); Richard L. Westrick, Jr., Social Circle, GA (US)

(73) Assignee: ABL IP HOLDING LLC, Conyers, GA (US)

( * ) Notice: Subject to any disclaimer, the term of this patent is extended or adjusted under 35 U.S.C. 154(b) by 923 days.

(21) Appl. No.: 17/333,685

(22) Filed: May 28, 2021

(65) Prior Publication Data

US 2022/0296764 A1 Sep. 22, 2022

Related U.S. Application Data

(63) Continuation-in-part of application No. 17/314,655, filed on May 7, 2021, which is a continuation-in-part
(Continued)

(51) Int. Cl.
*A61L 9/20* (2006.01)
*A61L 2/10* (2006.01)
(Continued)

(52) U.S. Cl.
CPC ........ *A61L 9/20* (2013.01); *A61L 2/10* (2013.01); *A61L 2/24* (2013.01); *A61L 2/26* (2013.01);
(Continued)

(58) Field of Classification Search
CPC .......... A61L 2/24; A61L 2/10; A61L 2202/11; A61L 2202/14; A61L 2202/25
See application file for complete search history.

(56) References Cited

U.S. PATENT DOCUMENTS 9,153,397 B2 10/2015 Lacey et al.
10,226,541 B2 3/2019 Trapani
(Continued)

FOREIGN PATENT DOCUMENTS

CN 109222447 A 1/2019
EP 3417348 B1 10/2020

OTHER PUBLICATIONS

Canadian Examination Report for Canadian Application No. 3,141,297, dated Feb. 21, 2023, 4 pages.
(Continued)

*Primary Examiner* — Kevin Joyner
(74) *Attorney, Agent, or Firm* — Buchanan Ingersoll & Rooney PC

(57) ABSTRACT

Antimicrobial system including a luminaire configured to emit a disinfection light in an ultraviolet band for disinfecting a vicinity of a target pathogen. A switching device that includes a primary relay pack. A control station, an integrated arming switch, a room sensor. The integrated arming switch has a communication interface, an integrated room sensor, a processor, and integrated arming switch programming in a memory. Execution of the integrated arming switch programming by processor configures the integrated arming switch to perform the following functions. Based on a second input from the operator, produce a visual inspection signal. In response to the integrated room sensor detecting occupancy of the vicinity of the physical space by the human, produce a room state signal. Send, via the communication interface, the visual inspection signal to enable the primary relay pack to control power to the luminaire to emit the disinfection light.

19 Claims, 24 Drawing Sheets

Related U.S. Application Data of application No. 17/204,082, filed on Mar. 17, 2021.

(51) Int. Cl.
    *A61L 2/24* (2006.01)
    *A61L 2/26* (2006.01)
    *G08B 5/22* (2006.01)
    *G08C 23/04* (2006.01)

(52) U.S. Cl.
    CPC ............ *G08B 5/22* (2013.01); *G08C 23/04* (2013.01); *A61L 2202/11* (2013.01); *A61L 2202/14* (2013.01); *A61L 2202/25* (2013.01); *A61L 2209/111* (2013.01); *A61L 2209/12* (2013.01); *A61L 2209/15* (2013.01)

(56) References Cited

U.S. PATENT DOCUMENTS

| | | | |
|---|---|---|---|
| 10,702,617 B2 | 7/2020 | Weeks, Jr. et al. | |
| 10,767,843 B2 | 9/2020 | Weeks, Jr. et al. | |
| 2009/0278479 A1* | 11/2009 | Platner | H05B 47/155 |
| | | | 340/309.9 |
| 2013/0117936 A1* | 5/2013 | Stryker | A61L 2/235 |
| | | | 422/24 |
| 2015/0062893 A1* | 3/2015 | Lynn | F21V 7/00 |
| | | | 362/231 |
| 2015/0086420 A1* | 3/2015 | Trapani | A61L 9/20 |
| | | | 422/24 |
| 2017/0246331 A1 | 8/2017 | Lloyd | |
| 2018/0255622 A1 | 9/2018 | Spero | |

OTHER PUBLICATIONS

Canadian Examination Report for Canadian Application No. 3,141,305, mailed Feb. 21, 2023, 5 pages.
Canadian Examination Report for Canadian Application No. 3,141,952, mailed Feb. 21, 2023, 5 pages.
Canadian Examination Report for Canadian Application No. 3,141,949, mailed Feb. 22, 2023, 6 pages.
Canadian Examination Report for Application No. 3,141,297, dated Jul. 27, 2023, 3 pages.
Canadian Examination Report for Application No. 3,141,949, dated Aug. 23, 2023, 3 pages.
Canadian Examination Report for Application No. 3,141,952, dated Aug. 23, 2023, 3 pages.
Non-Final Office Action issued by the U.S. Patent and Trademark Office in U.S. Appl. No. 17/314,655, mailed Jun. 11, 2024, U.S. Patent and Trademark Office, Alexandria, VA. (33 pages).
Notice of Allowance issued by the U.S. Patent and Trademark Office in U.S. Appl. No. 17/204,082, mailed May 22, 2024, U.S. Patent and Trademark Office, Alexandria, VA. (27 pages).

* cited by examiner

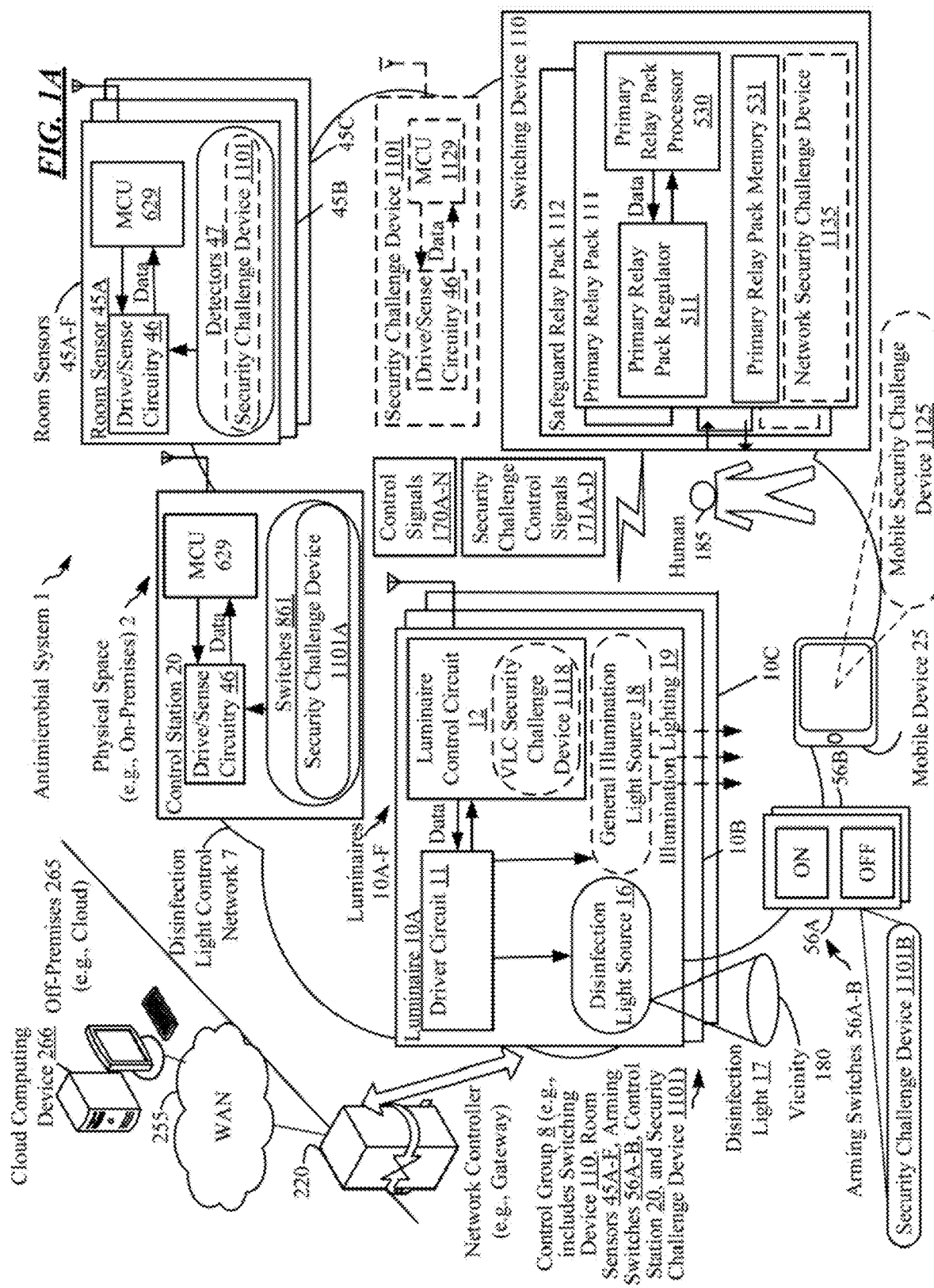

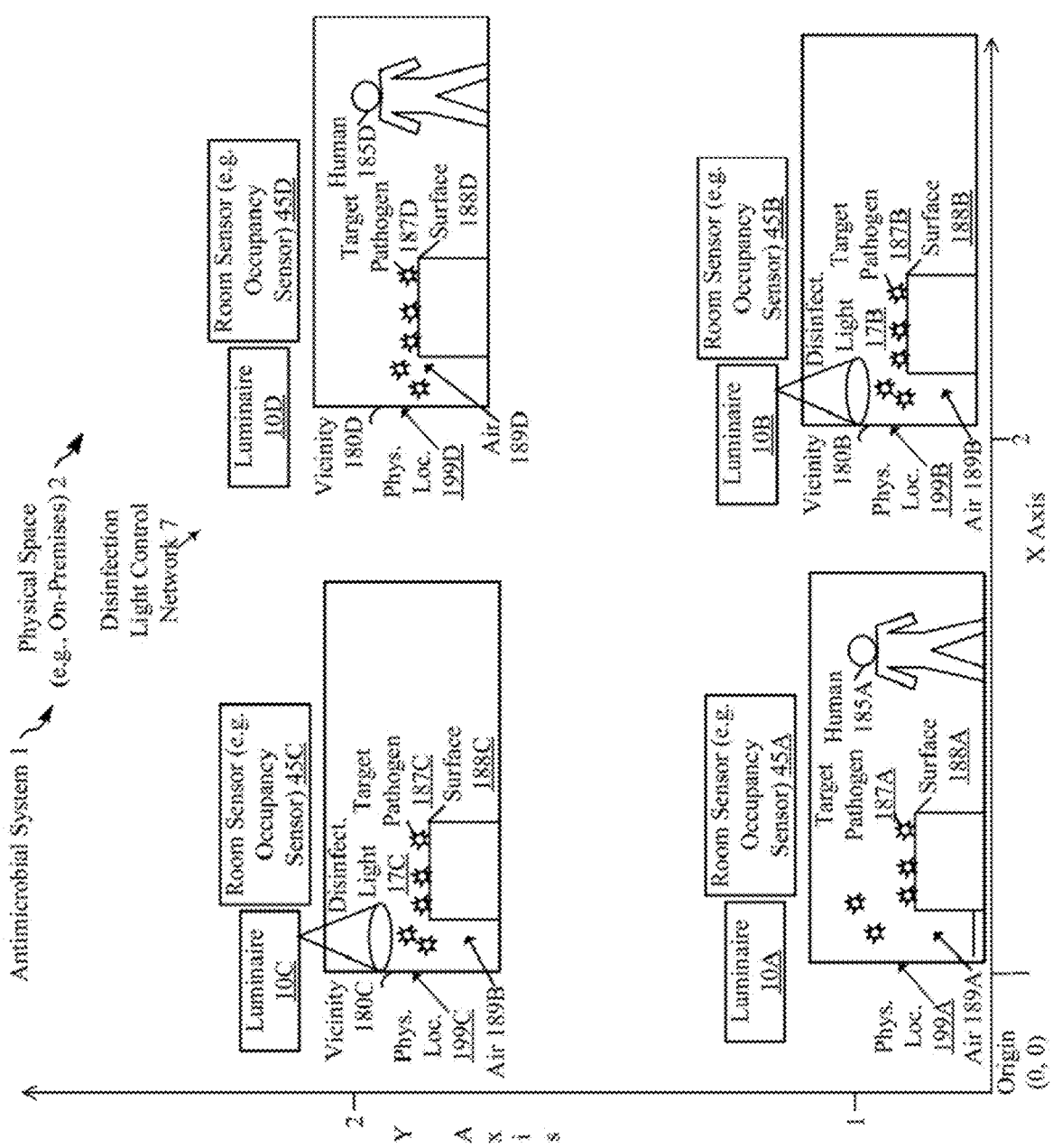

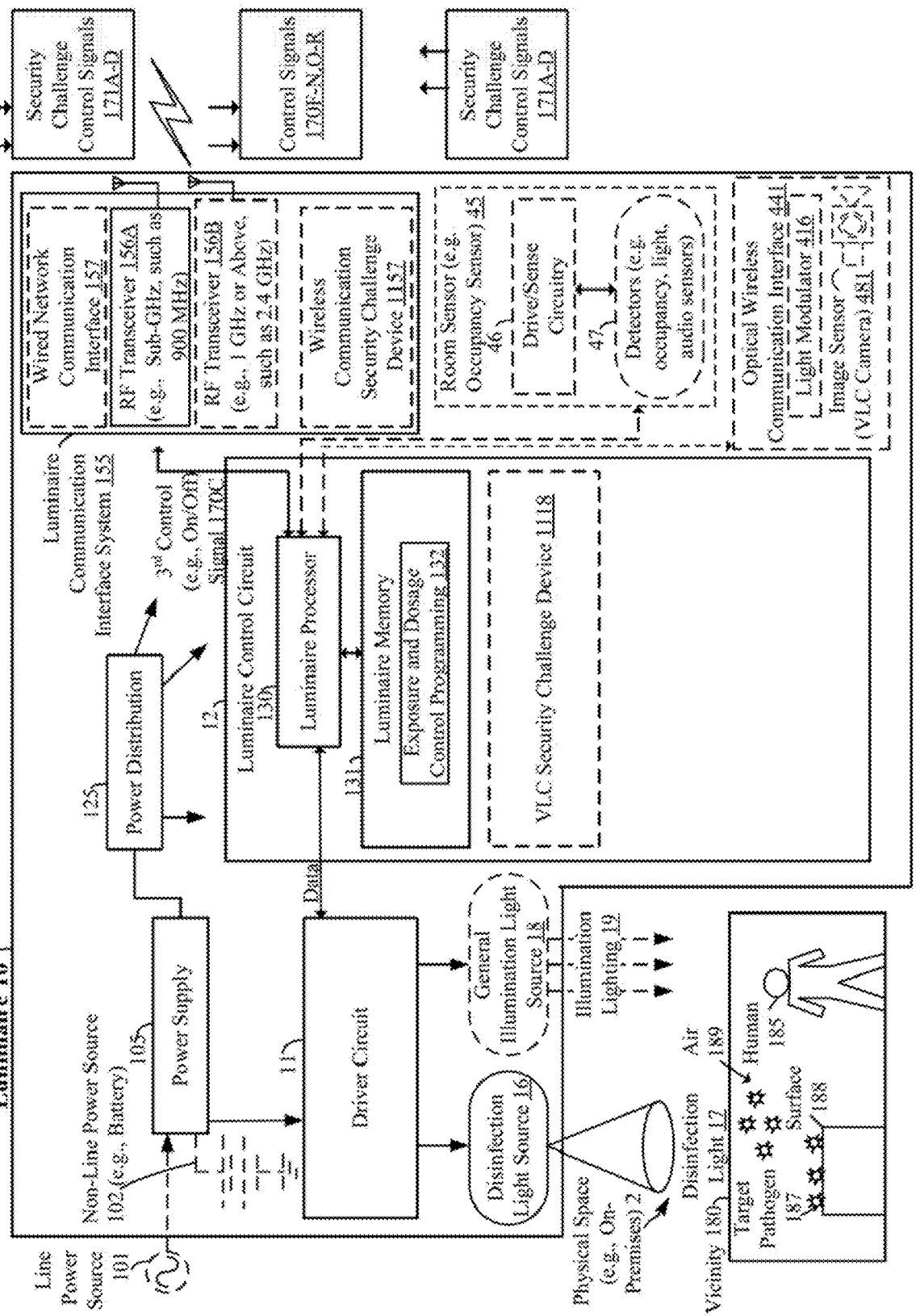

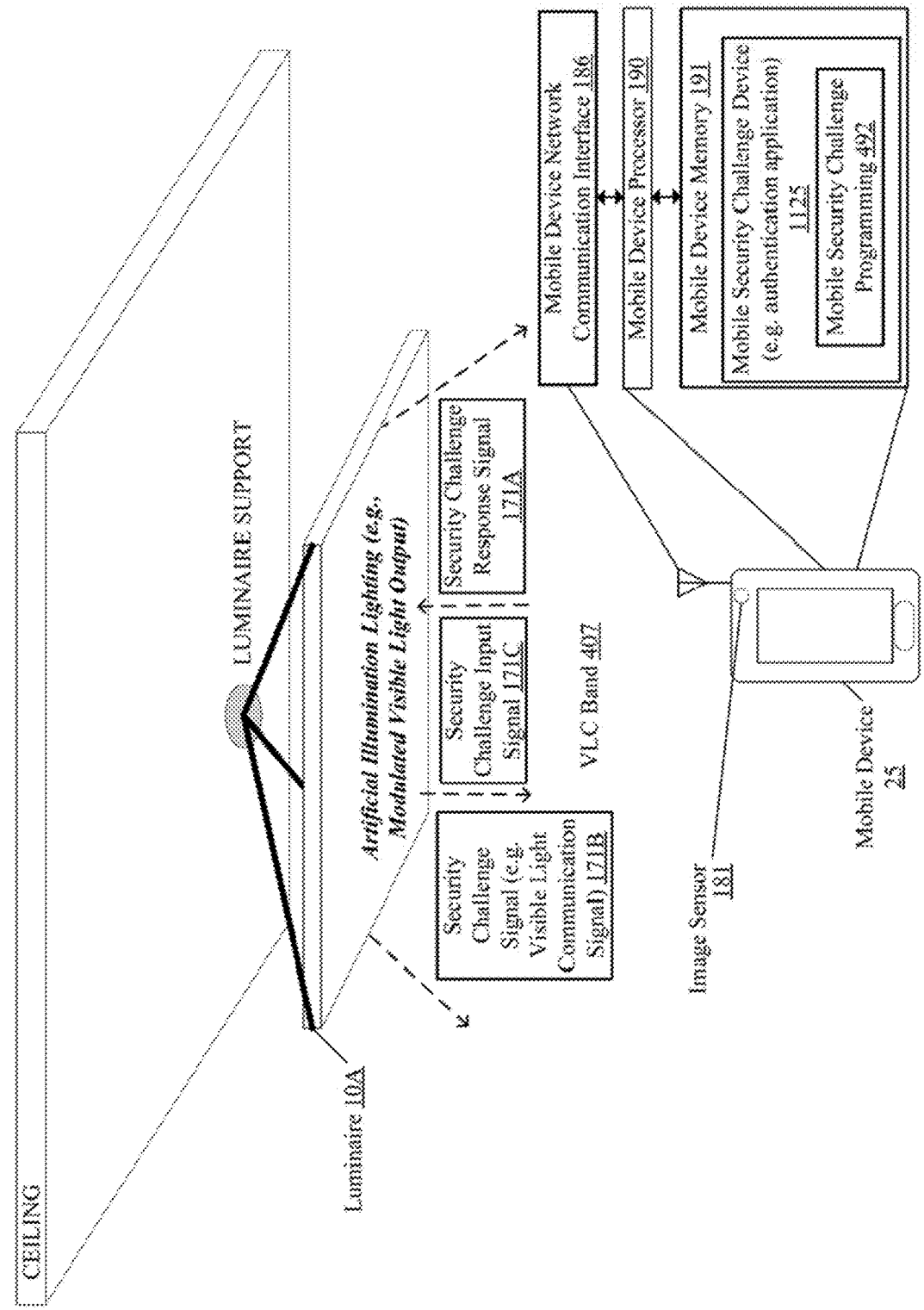

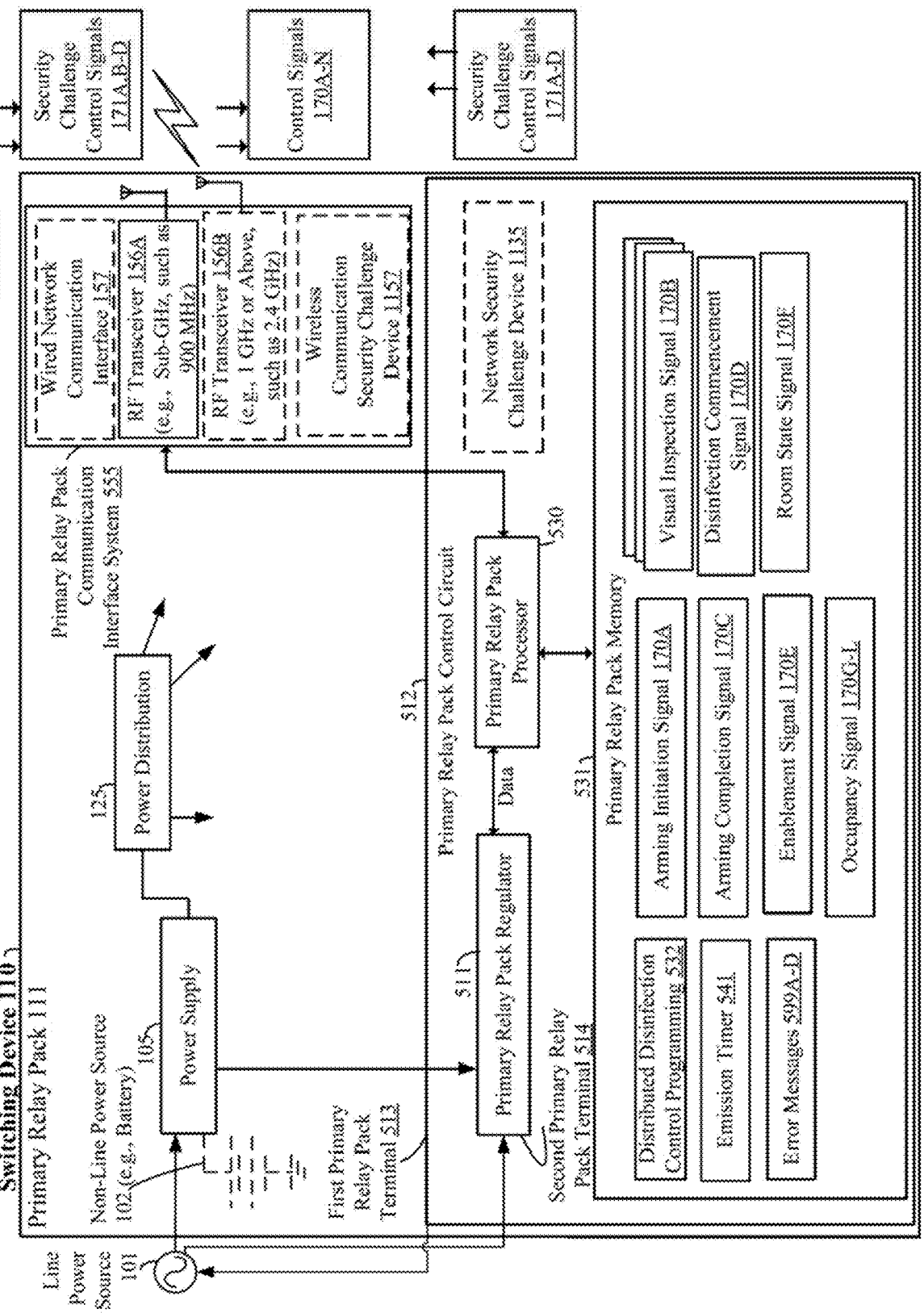

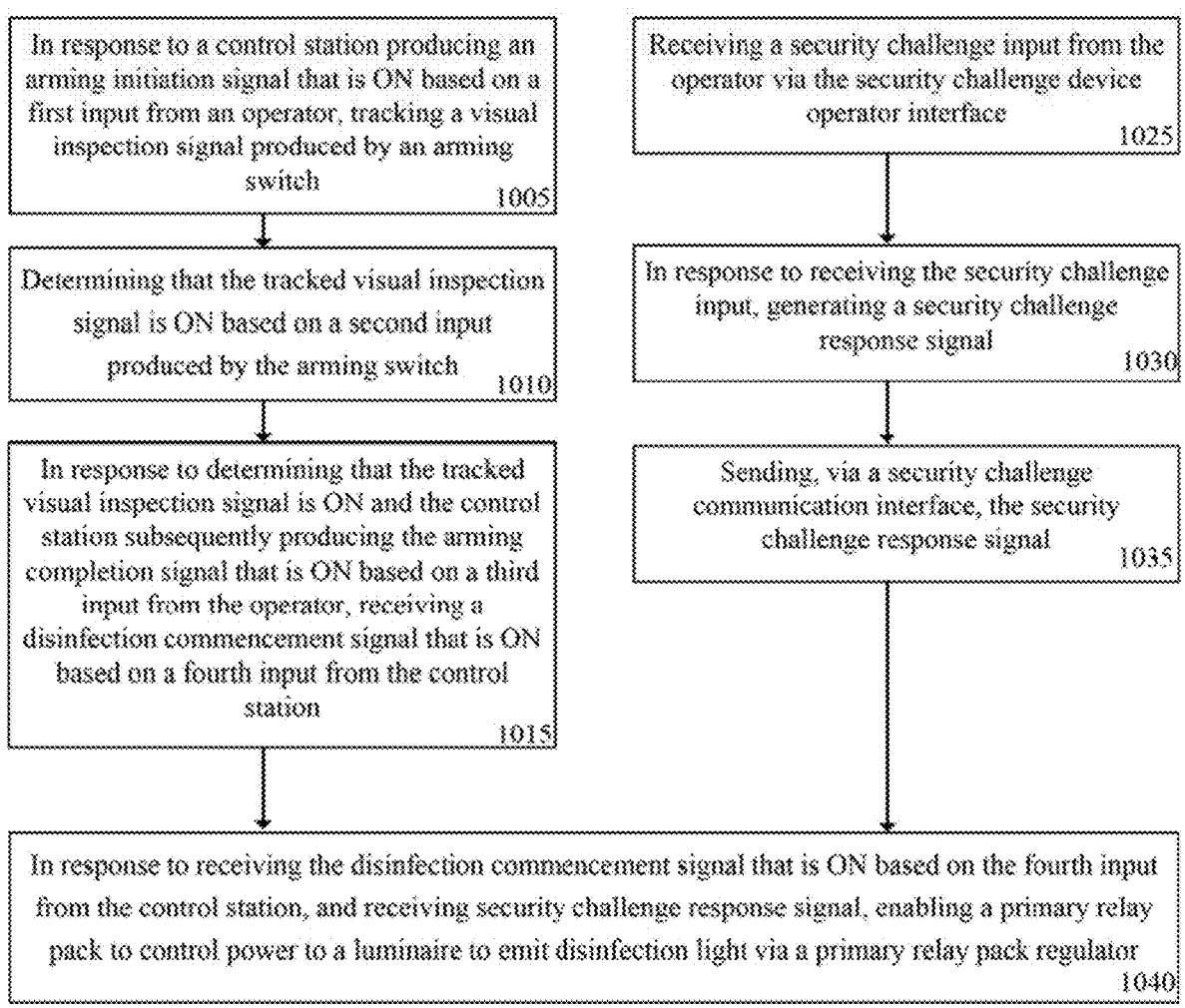

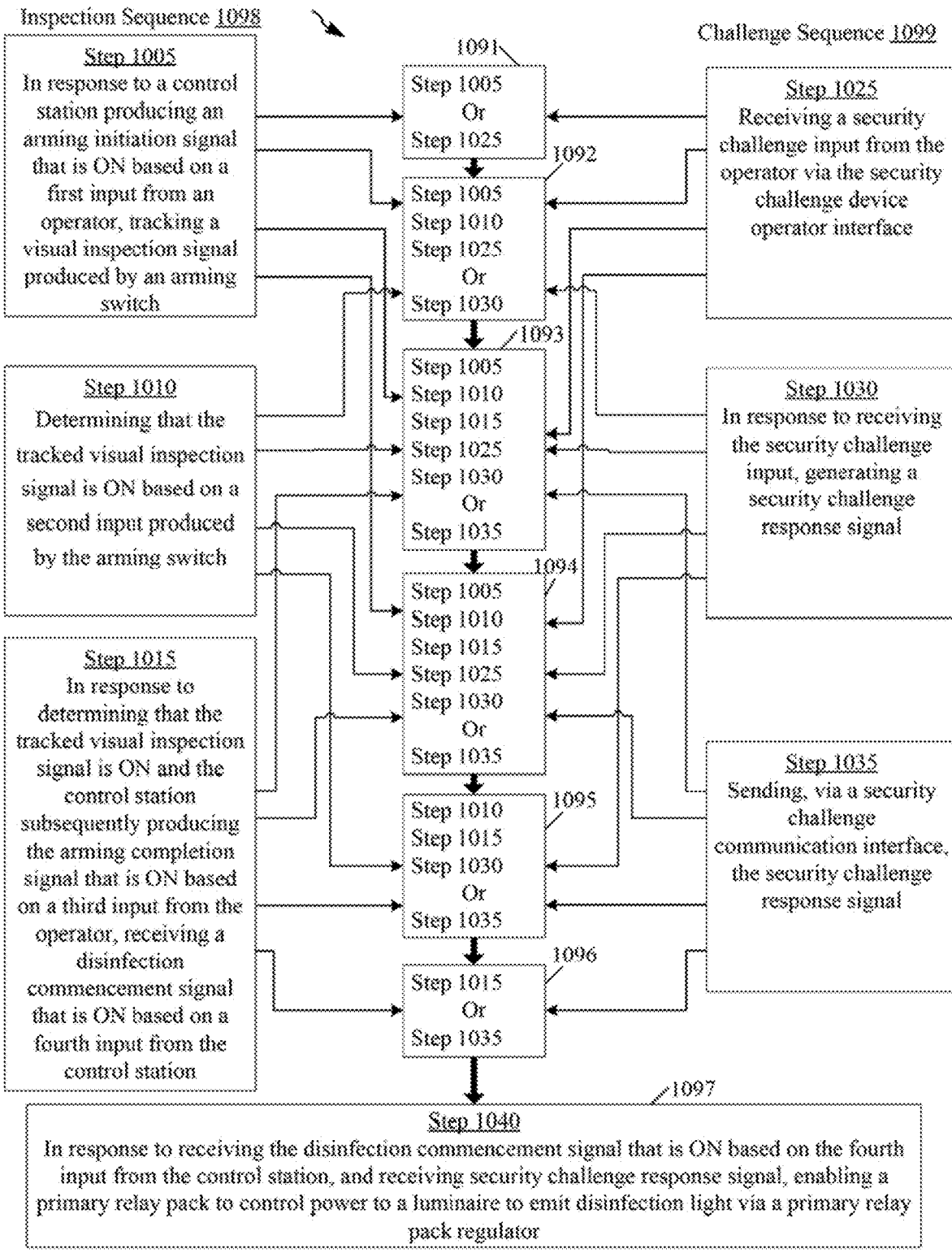

Fingerprint Reader 1201 (e.g. Security Challenge Device Operator Interface 1161)

Retinal Scanner 1206 (e.g. Security Challenge Device Operator Interface 1161)

Keypad 1211 (e.g. Security Challenge Device Operator Interface 1161)

Card Swipe Reader 1216 (e.g. Security Challenge Device Operator Interface 1161)

ANTIMICROBIAL SYSTEM WITH DISTRIBUTED DISINFECTION CONTROLS, INTEGRATED ARMING SWITCH SENSORS, AND STREAMLINED SAFE LOCKOUT PROTOCOL

CROSS-REFERENCE TO RELATED APPLICATIONS

This application is a continuation-in-part of U.S. patent application Ser. No. 17/314,655, filed on May 7, 2021, titled "Antimicrobial System with Distributed User Authenticated Disinfection Controls and Authenticated Safe Lockout Protocol," which is a continuation-in-part of U.S. patent application Ser. No. 17/204,082, filed on Mar. 17, 2021, titled "Antimicrobial System with Distributed Disinfection Controls and Safe Lockout Protocol," the entire disclosures of which are incorporated herein by reference.

TECHNICAL FIELD

The present subject matter relates to disinfection lighting devices, luminaires incorporating disinfection light components, and techniques of operating such equipment to provide disinfection light, e.g., ultraviolet (UV) light, to deactivate a pathogen for an antimicrobial application, e.g., for disinfection.

BACKGROUND

Disinfection light, such as ultraviolet (UV) light, is known to deactivate various types of pathogens. In recent years, there have been various proposals to incorporate, in general lighting equipment, light sources specifically configured to deactivate bacteria, viruses, and other pathogens on a surface, such as Methicillin-Resistant *Staphylococcus aureus* (MRSA) on work surfaces, sinks, floors etc. of hospitals, nursing homes or the like.

A number of these proposals have suggested use of disinfection light at or around 405 nanometers (nm), that is to say, in the near-ultraviolet end of the visible spectrum. Some examples of such equipment have utilized light in a wavelength range that includes at least a portion in the humanly visible spectrum for the disinfection light, e.g., disinfection light having a maximum peak at a wavelength in a range of 400 nanometers (nm) to 450 nm, which may be perceptible as visible light during disinfection operations. Other types of lighting equipment providing a disinfection illumination function or service, however, may utilize appropriate wavelengths in the range from 180 nm to 380 nm in the ultraviolet portion of the spectrum that is not visible to a human 185 during a disinfection operation. At least some UV wavelengths appear to be more efficacious for disinfection than visible wavelengths. Although some UV wavelengths (e.g. far-UVC in the range of 200 nm to 280 nm), if used properly, may have little or no harmful effect on human 185 occupants, other UV wavelengths suitable for disinfection may be harmful to the people in the area. However, even far-UVC light, if used improperly, can still be harmful to humans.

For many UV applications, such as disinfection, effectiveness requires at least a certain minimum intensity of the applied UV light. For example, to ensure effective disinfection of a surface or air in a room in a hospital or the like, it may be necessary to apply UV of a particular intensity for a specific duration of time. The application of sufficient intensity over a specific duration serves to apply a cumulative amount of UV light energy so as to deactivate or kill pathogens, such as viruses, bacteria, protozoans, fungi, such as mold, or other harmful microorganisms.

As noted above, UV light for disinfection or other functions is not visible to a human. Unlike general illumination with visible light, a person in or entering a space being treated might not realize that a luminaire is outputting UV light. Possible acute and chronic damage to eyes and skin may result from the UV wavelength used in many germicidal lamps. For certain bands of UV light (e.g., UVB) penetration of human tissue can cause sunburn, skin cancer, cataracts, photokeratitis, and other conditions. These particular concerns are more pronounced when a person operating the UV light is untrained on or unauthorized to use a luminaire outputting UV light. A person who is unfamiliar with the potential risks of UV light may place themselves and others in danger. In addition, although disinfection lamps which product light in the lower end of the visible light range, such as the 405-430 nm wavelength range, can be used for disinfection in occupied spaces, the 405-430 nm range is not as effective against viruses as UV light and typically require a much longer duration of exposure for disinfection of a surface.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1A is a high-level functional block diagram of an example of an antimicrobial system that distributed disinfection controls includes six luminaires and a control group.

FIG. 1B illustrates tying the control of a disinfection light source of the luminaire to the position of an occupant (e.g., human) in the physical space.

FIG. 4A is a block diagram of a luminaire of the antimicrobial system.

FIG. 4B is an isometric view of a luminaire mounted in the physical space and in visible light communication (VLC) with a mobile device.

FIG. 5 is a block diagram of a switching device including a primary relay pack of the antimicrobial system.

FIG. 10A is a flowchart diagramming of an authenticated safe lockout protocol of the antimicrobial system.

FIG. 10B is a block flowchart diagramming of the authenticated safe lockout protocol interleaving strategy.

DETAILED DESCRIPTION

Figure 2A:
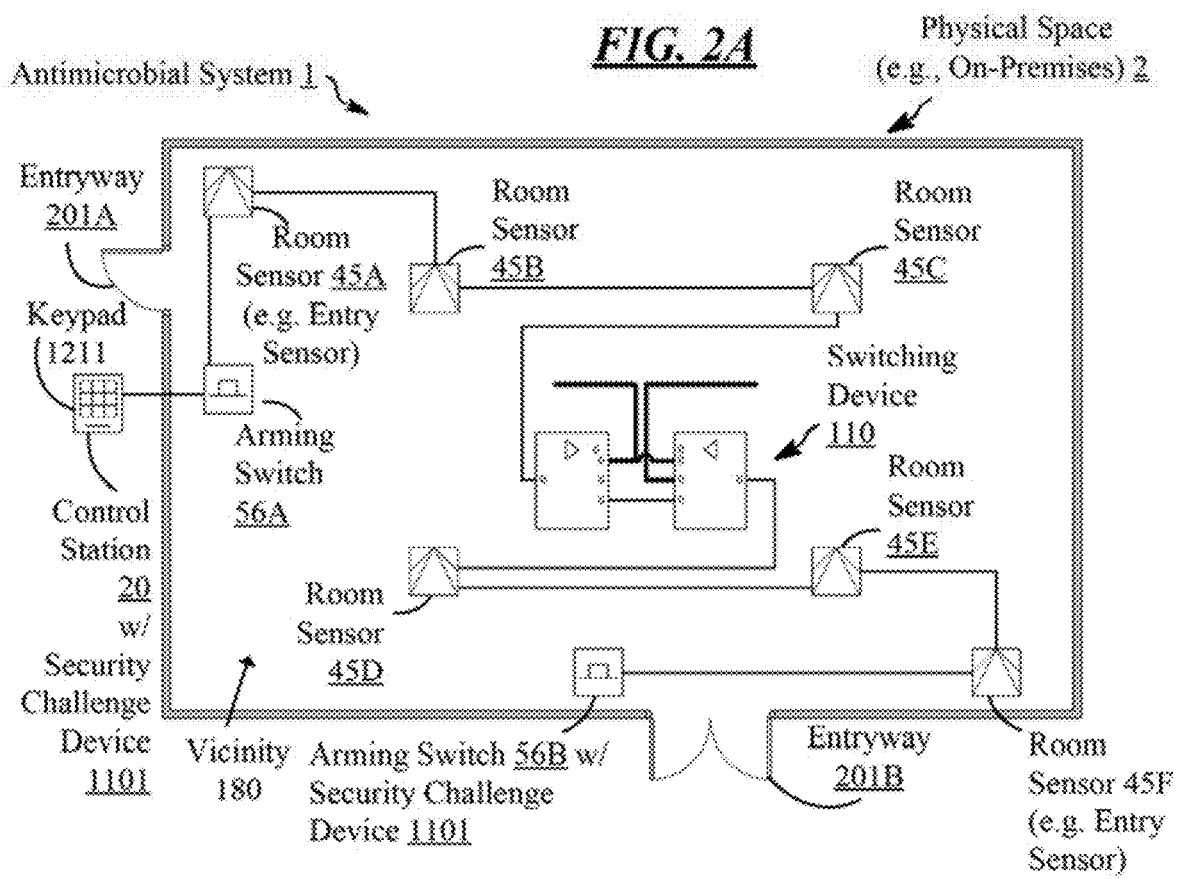
FIG. 2A is a high-level functional block diagram of an example of an antimicrobial system that includes luminaires with external sensors and data connections.

Accordingly, an antimicrobial system 1 is needed to safely control human 185 exposure to disinfection light 17 emission in a potentially harmful wavelength range while allowing for more rapid disinfection of a target pathogen on a surface 188 or suspended in air 189. The examples described herein describe to the antimicrobial system 1, e.g., germicidal ultraviolet (GUV) system, with distributed disinfection controls. The distributed disinfection controls can be used to implement an authenticated safe lockout protocol 1001 (see FIG. 10A) to secure a vicinity 180 or room of a physical space 2. In particular, an integrated arming switch 1456 either replacing or in addition to arming switches 56A-B and room sensors 45A-F can be used to enhance or replace the authenticated safe lockout protocol 1001 via the streamlined safe lockout protocol 1800 (see FIG. 18). Secured rooms are rooms devoid of humans 185, and therefore the antimicrobial system 1 can safely emit high levels of disinfection light 17 in a potentially harmful wavelength range without risk of overexposing the human 185 to disinfection light 17. Rooms are secured in part by having an authorized operator confirm their authorization by completing a security challenge via a security challenge device 1101.

As described in further detail below, distributed disinfection control programming 532 of a switching device 110 (see FIG. 5) implements an authenticated safe lockout protocol 1001 (see FIG. 10A) with the following arming sequence to enable disinfection of a physical space 2. First, an operator begins the arming sequence at a control station 20 by pressing a disinfection initiation user interface element 862, such as a "start check" button. Second, within a limited time (e.g., 5 minutes), the operator inspects the physical space 2 for occupants, e.g., human(s) 185, and verify that no occupants are in the room by pressing an inspection switch 761, such as a top button on each arming switch 56A-B. Third, once all arming switches 56A-B have been pressed, the operator returns to the control station 20 and presses an arming completion user interface element 863, such as a "finish check" button. If all arming switches 56A-B have been pressed and the room sensors 45A-F have timed out indicating no occupancy by a human 185 in the physical space 2, then the touch screen display 811 or a pilot light status indicator of the control station 20, such as a "safeguards OK" indicator, will light and a disinfection commencement user interface element 864, such as a key switch, will be enabled. Fourth, the operator can then start the disinfection process using the disinfection commencement user interface element 864, such as the key switch.

The streamlined safe lockout protocol 1800 enhances or replaces the authenticated safe lockout protocol 1001 by adding additional safety features. Before the operator starts the disinfection process using the disinfection commencement user interface element 864, an integrated arming switch 1456 can disable the functions to produce or send the room state signal 1770B; the integrated arming switch 1456 can enable these functions to produce or send the room state signal 1770B in response to receiving the disinfection commencement signal 170D when the operator starts the disinfection process using the disinfection commencement user interface element 864. The integrated arming switch 1456 can also produce a motion status signal 1762 via the integrated arming switch status indicator 1761.

During the authenticated safe lockout protocol 1001, the operator will also need to complete at least one security challenge. A security challenge device 1101 will receive a security challenge input from the operator via a security challenge device operator interface 1161. Next, in response to receiving the security challenge input, the security challenge device 1101 generates a security challenge response signal 171A. Then, the security challenge device 1101 sends, via a security challenge communication interface system 1155, the security challenge response signal 171A. Having both started the disinfection process and completed the security challenge, the luminaires 10A-F will turn on to emit disinfection light 17 for a disinfection time period, for example. If any of the room sensors 45A-F or integrated arming switches 1456A-B detect occupants, e.g., human(s) 185, or any inspection switch 761, such as the top button on the arming switches 56A-B is pressed during the disinfection time period, then the disinfection light 17 of the luminaires 10A-F is immediately turned off by the switching device 100 and the disinfection sequence aborted.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various examples disclosed herein relate to an antimicrobial system 1 that includes lighting devices for disinfection and to luminaire(s) 10 incorporating a disinfection light source 16 and an optional general illumination light source 18. The luminaire(s) 10 implements distributed disinfection control programming 532 with an authenticated safe lockout protocol 1001 for disinfection of a target pathogen 187 on a surface 188 or suspended in air 189. The disinfection light 17 produced has properties (e.g. wavelength, energy and/or time duration) suitable to deactivation of one or more potentially harmful target pathogen(s) 187.

Target pathogen(s) 187, for example, include microorganisms, bacteria, viruses (e.g., coronavirus, norovirus, etc.), protozoa, prions, fungal spores, and other infectious agents. Such a target pathogen 187 is deactivated, for example, if the disinfection light exposure deactivates the pathogen or otherwise damages the target pathogen 187 (e.g. ruptures the cell membrane or breaks DNA or RNA chain in the pathogen) so as to limit or prevent the harmful function of the target pathogen 187.

Although the discussion herein is focused on light fixture type luminaire(s) 10 that have a fixed position in a space, it should be understood that other types of luminaire(s) 10 can be used/sensed in lieu of light fixtures, such as lamps. The term "luminaire" 10 as used herein, is intended to encompass essentially any type of device, e.g., a light fixture or a lamp that processes energy to generate or supply disinfection light 17 from a disinfection light source 16. The luminaire 10 optionally emits artificial illumination lighting 19 from a general illumination light source 18, for example, for general illumination of a physical space 2 intended for use of or occupancy or observation, typically by a living organism that can take advantage of or be affected in some desired manner by the light emitted from the device. The luminaire 10 may provide the optional artificial illumination lighting 19 for use by automated equipment, such as sensors/monitors, robots, etc. that may occupy or observe the illuminated physical space 2, instead of or in addition to light provided for an organism. However, it is also possible that one or more luminaire(s) 10A-F in or on a particular premises have other lighting purposes, such as signage for an entrance or to indicate an exit. In most examples, the luminaire(s) 10A-F disinfect a physical space 2 of a target pathogen 187 and optionally illuminate a physical space 2 of a premises to a level useful for a human 185 in or passing through the space 2, e.g. general illumination lighting 19 of an office, room, or corridor in a building or of an outdoor physical space 2 such as a street, sidewalk, parking lot or performance venue. The actual disinfection light source 16 of the luminaire 10 that emits disinfection light 17 may be any type of light emitting device, several examples of which are included in the discussions below. Each example of the luminaire 10 with integrated disinfection capability described later includes a disinfection light source 16.

The "luminaire" 10 can include other elements such as electronics and/or support structure, to operate and/or install the particular luminaire implementation. Such electronics hardware, for example, may include some or all of the appropriate driver(s) for the disinfection light source 16 and optional general illumination light source 18, any associated control processor or alternative higher level control circuitry, and/or data communication interface(s). As noted, the lighting component(s) are located into an integral unit, such as a light fixture or lamp implementation of the luminaire 10. The electronics for driving and/or controlling the lighting component(s) may be incorporated within the luminaire 10 or located separately and coupled by appropriate means to the light source component(s).

The term "antimicrobial system" 1, 1401 "lighting control system," or "lighting system" as used herein, is intended to encompass essentially any type of system that either includes a number of such luminaires 10A-F coupled together for data communication and/or luminaire(s) including or coupled together for data communication with one or more switching device(s) 110 (e.g., primary relay pack 111 and/or safeguard relay pack 112), room sensors 45A-F, arming switch(es) 56A-B, control station(s) 20, mobile device(s) 25, security challenge devices 1101, remote controls, central lighting or building control systems, servers, etc.

Figure 6:
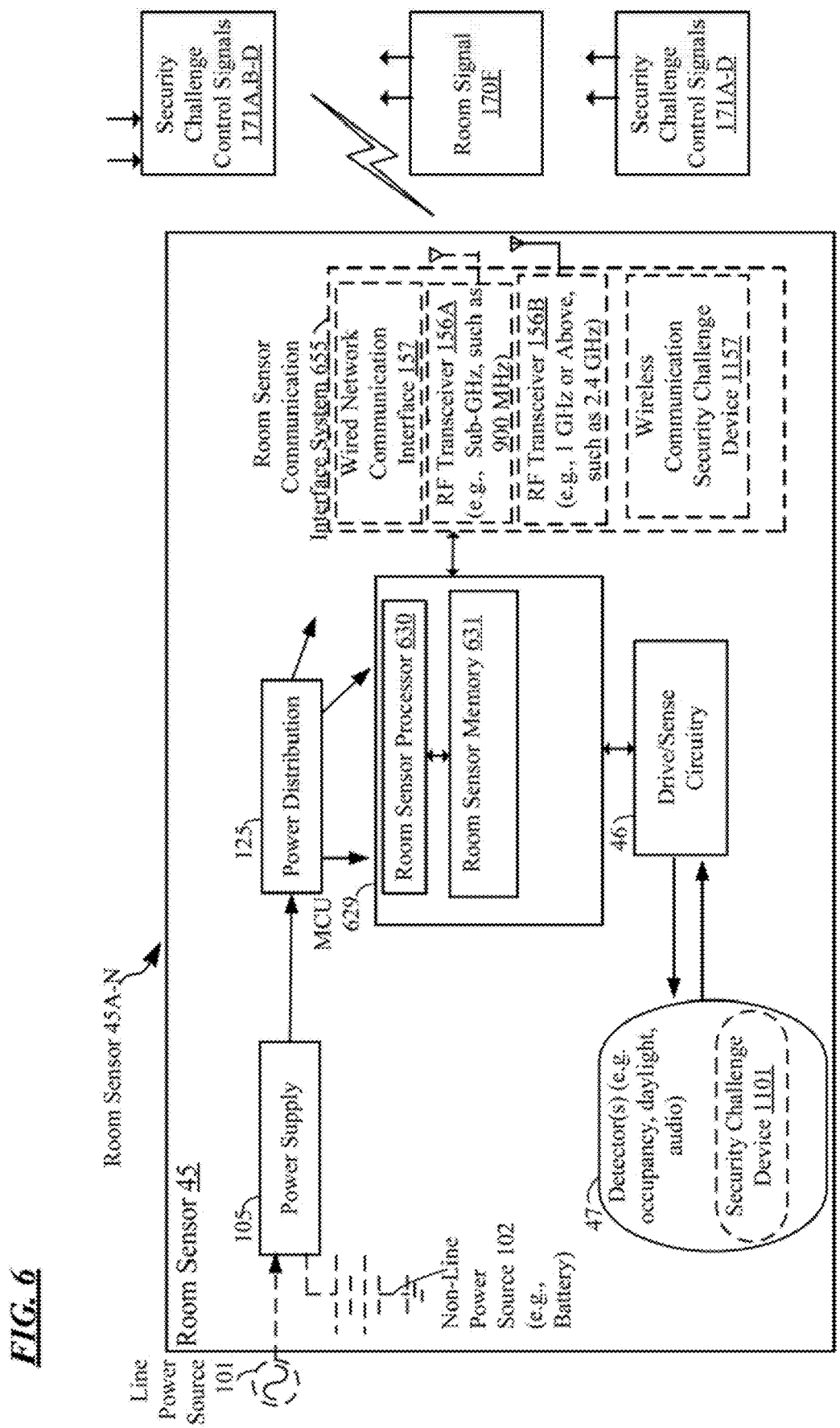
FIG. 6 is a block diagram of a room sensor of the antimicrobial system.
Figure 7:
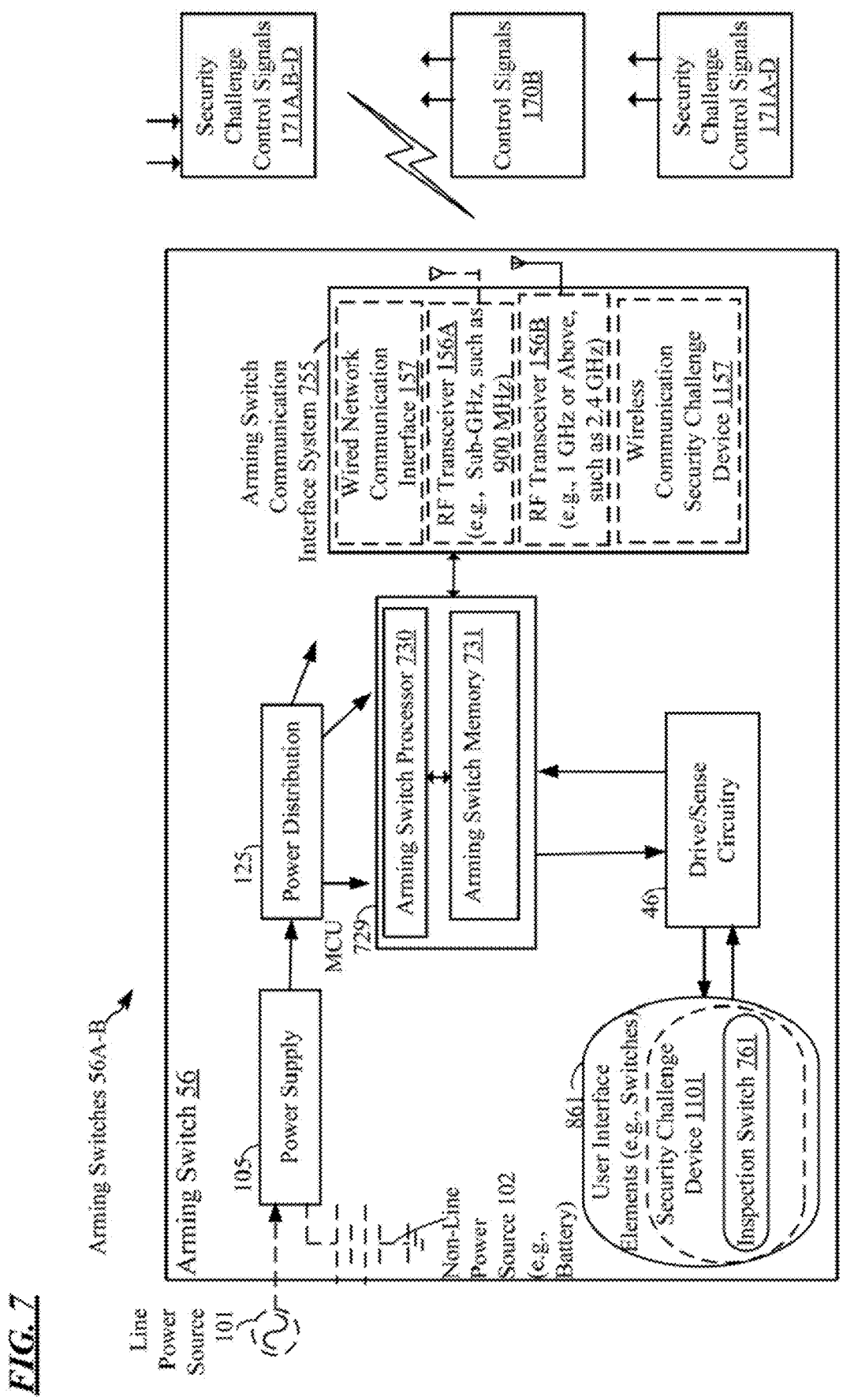
FIG. 7 is a block diagram of an arming switch of the antimicrobial system.

The term "integrated arming switch" 1456 as used herein, is intended to encompass any combination of components, features, or traits found in the arming switch 56 of FIG. 7 and the room sensor 45 of FIG. 6. This includes disclosed optional components such as the room sensor communication interface system 655, arming switch communication interface system 755, and their subcomponents; Optional security challenge device 1101 and any feasible species of security challenge device 1101 are also contemplated as components of the integrated arming switch 1456. Additionally, the antimicrobial system 1401 will broadly treat the visual inspection signal 1770A from the integrated arming switch 1456 as equivalent to the visual inspection signal 170B from an arming switch 56 in both the authenticated safe lockout protocol 1001 and in execution of the functions of the distributed disinfection control programming 532; and likewise the antimicrobial system 1401 will broadly treat the room state signal 1770B from the integrated arming switch 1456 as equivalent to the room state signal 170F from a room sensor 45 in both the authenticated safe lockout protocol 1001 and in execution of the functions of the distributed disinfection control programming 532.

The disinfection light 17 of a luminaire 10, for example, may have an intensity and/or other characteristic(s) that satisfy an industry acceptable performance standard for disinfection of surface(s) 188 or air 189 in a vicinity 180 of the physical space 2. The term "antimicrobial" means to disinfect by disinfecting or otherwise deactivating, killing, or slowing the spread of the target pathogen 187. The term "disinfect" means to reduce an amount of target pathogen 187 by a desired amount, for example, by a desired log reduction. The disinfection performance standard may vary for different uses or applications of the physical space 2, for example, as between residential, medical, hospital, office, manufacturing, warehouse, or retail spaces. Moreover, the disinfection performance standard may vary among multiple vicinities 180A-D of the physical space 2, for example, a physical space 2 may subdivided into different areas requiring varying levels of disinfection requirements, such as a desired amount (e.g., desired log reduction). Any luminaire 10, however, may be controlled in response to commands received with the network technology of the antimicrobial system 1, e.g. to turn the disinfection light source 16 on ON/OFF, to dim the light intensity of the disinfection light 17, to adjust the disinfection light 17 output, etc.

Terms such as "disinfection light" 17 when referring to the disinfection light source 16 or "artificial lighting" or "illumination lighting" 19 when referring to the general illumination light source 18, are intended to encompass essentially any type of lighting in which a luminaire 10 produces light by processing of electrical power to generate the light. A luminaire 10 for disinfection light 17, for example, may take the form of a lamp, light fixture, or other luminaire 10 that incorporates a disinfection light source 16, where the disinfection light source 16 by itself contains no intelligence or communication capability, such as one or more lamps (e.g., gas excimer lamps), LEDs or the like, etc. of any suitable type. However, the luminaire 10 includes a luminaire control circuit 12 implements distributed disinfection control programming 532 with the authenticated safe lockout protocol 1001 described herein.

Illumination lighting 19 output from the general illumination light source 18 of the luminaire 10 may carry information, such as a code (e.g. to identify the luminaire or its location) or downstream transmission of communication signaling and/or user data. The light based data transmission may involve modulation or otherwise adjusting parameters (e.g. intensity, color characteristic or distribution) of the illumination lighting 19 from the general illumination light source 18.

Terms such as "disinfection lighting device," "lighting device," or "lighting apparatus," as used herein, are intended to encompass essentially any combination of an example of a luminaire 10 discussed herein with other elements such as electronics and/or support structure, to operate and/or install the particular luminaire implementation. Such electronics hardware, for example, may include some or all of the appropriate driver(s) for the disinfection light source 16, any associated control processor or alternative higher level control circuitry, and/or data communication interface(s). The electronics for driving and/or controlling the lighting component(s) may be incorporated within the luminaire 10 or located separately and coupled by appropriate means to the light source component(s).

The term "coupled" as used herein refers to any logical, optical, physical or electrical connection, link or the like by which signals or light produced or supplied by one system element are imparted to another coupled element. Unless described otherwise, coupled elements or devices are not necessarily directly connected to one another and may be separated by intermediate components, elements or communication media that may modify, manipulate or carry the light or signals.

The direction of the arrows in the drawings, however, are for ease of illustration only. In actual implementations of the luminaire 10, the beams of the disinfection light 17 may be aimed in a variety of different directions, to facilitate optical processing by the various components discussed herein and/or to direct the disinfection light 17 output in a manner suitable to a particular application or installation. Also, the drawings show disinfection light 17 and illumination lighting 19 outputs from the luminaire 10 in a downward direction, for example, as if mounted to direct output light down from a ceiling, pedestal or lamp post through an illuminated volume toward a floor, an object surface 188 (e.g., work surface), or air 189 positioned above the floor. It should be apparent that a luminaire 10 may be positioned in a variety of other orientations suitable for disinfection of a target pathogen 187 in a particular physical space 2, including surface(s) 188 and air 189 by a desired amount (e.g., desired log reduction).

Reference now is made in detail to the examples illustrated in the accompanying drawings and discussed below. FIG. 1A is a high-level functional block diagram of an example of an antimicrobial system 1 that includes six luminaires 10A-F like that of FIG. 4 and a control group 8. The control group 8 includes a switching device 110 like that of FIGS. 5 and 9, six room sensors 45A-F like that of FIG. 6, two arming switches 56A-B like that of FIG. 7, and a control station 20 like that of FIG. 8. Antimicrobial system 1 implements the authenticated safe lockout protocol 1001 (see FIG. 10A). As described herein, the authenticated safe lockout protocol 1001 (see FIG. 10A) also includes communications in support of turning a disinfection light source 16 of luminaires 10A-F on/off, adjusting intensity, sensor trip events, and other control signals 170A-N and security challenge control signals 171A-D. As shown, the control signals 170A-N and security challenge control signals 171A-D can be received from the control group 8 via the disinfection light control network 7.

Antimicrobial system 1 may be designed for a physical space 2 (e.g., on-premises), which can be indoor or outdoor. As shown in the example, antimicrobial system 1 includes a variety of lighting network elements, including luminaires 10A-F, room sensors 45A-F, a switching device 110, arming switches 56A-B, and control station 20. Luminaires 10A-F can be coupled via a disinfection light control network 7 (e.g., wired or wireless network) to various control group 8 members to receive control signals 170A-N or security challenge control signals 171A-D for the disinfection light 17 via the disinfection light network 7 or alternatively include (e.g., integrate or incorporate) control group 8 members to receive control signals 170A-N or security challenge control signals 171A-D for the disinfection light 17.

Hence, control operations for the disinfection light 17 of the antimicrobial system 1 can involve networked collaboration between the luminaires 10A-F and the devices that comprise the disinfection light control group 8. Luminaires 10A-F can receive the control signals 170A-N or security challenge control signals 171A-D from control group 8 members via the disinfection light control network 7. All or some of the components of the depicted control group 8, such as room sensors 45A and safeguard relay pack 112 of the switching device 110 (see FIG. 9), etc. can be directly incorporated into the luminaires 10A-F, as shown in FIG. 5.

The control group 8 includes room sensors 45A, which are occupancy, motion, ozone, daylight, or audio detector(s) 47, to enable controls for occupancy and intensity adjustment of the disinfection light 17. The arming switches 56A-B are included in order to allow an operator to input into the antimicrobial system 1 that no human 185 is within the vicinity 180 of any disinfection light 17. The control station 20 includes user interface elements (e.g., switches 861) to allow an operator to activate the arming switches 56A-B, and ultimately energize the luminaires 10A-F in order to emit disinfection light 17. The security challenge device 1101 is included to verify that the operator is authorized to operate the antimicrobial system 1, and the security challenge device 1101 may be a standalone device physically separate from the other members of the control group 8 and the luminaires 10A-F, or the security challenge device 1101 may be integrated into a member of the control group 8, as well as other devices such as mobile devices 25 or cloud computing devices 8 not within the control group 8.

Distributed and networked control devices in a control group 8 minimize risk of unintentional exposure to disinfection light 17 that is potentially harmful to human(s) 185 and animals. This is accomplished with an intelligent networked control antimicrobial system 1 in which each device in the antimicrobial system 1 must properly function and communicate before the primary relay pack 111 and safeguard relay pack 112 are enabled to provide power to luminaires 10A-F that emit disinfection light 17. The primary application advantage of using this approach is that the antimicrobial system 1 is expandable and adaptable for a wide variety of sizes of the physical space 2 and unique room designs.

Figure 9:
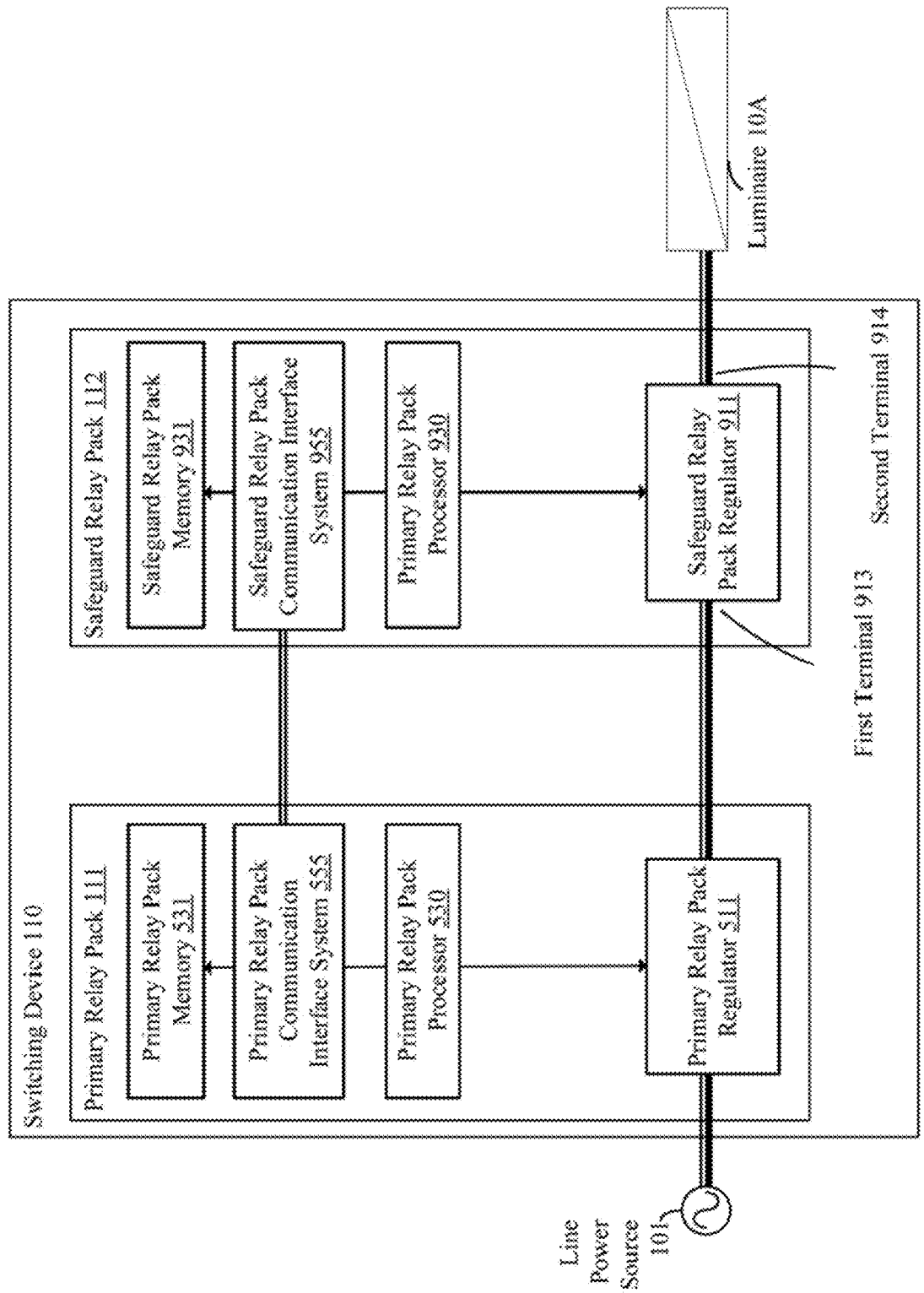
FIG. 9 is a block diagram of a switching device including a primary relay pack and a safeguard relay pack of the antimicrobial system.

In one example, the devices in the control group are: a control station 20 with access control implemented as a security challenge device 1101, one or more arming switch(es) 56A-B, one or more entry or door motion sensor(s) and one or more ceiling or fixture-mount motion sensor(s) collectively labeled room sensors 45A-F, and one or more switching device pair(s) of a primary relay pack 111 and a safeguard relay pack 112 as a collective switching device 110, with an integrated relay in each relay pack 111, 112. The relays in the relay packs 111, 112 control power to the 10A-F that emit disinfection light 17 via the electrical regulators 511, 911 as shown in FIGS. 5 and 9. At least two relay packs 111, 112 per circuit connected in series are implemented to safeguard against internal relay control circuit malfunction, or a relay failure. In most applications a normally open electromechanical relay is the preferred switching component of the switching device 110 since it will automatically disconnect power to the luminaires 10A-F in case of electronics failure in the switching device 110. However, due to the layered safeguards incorporated into the system, any electromechanical switching component (e.g. normally closed relay, latching relay, or solenoid) or semiconductor switching component (e.g. thyristor, Solid State Relay, MOSFETs, BJTs, IGBTs) with sufficient electrical ratings may be used instead of the normally open electromechanical relay.

The arming switch(es) 56A-B are mounted in a physical space 2 as needed to validate that all areas of the physical space 2 have been visually inspected for human(s) 185. The entry point motion sensor(s) of the room sensors 45A, F in FIG. 2 are installed adjacent to each entryway 201A-B in FIG. 2 and disable the luminaires 10A-F that emit disinfection light 17 when someone enters the room during the disinfectant period. The room occupancy sensors of the room sensors 45B-E mounted on the ceiling, room corners or walls, provide overlapping coverage. The switching device 110 monitors the status of all networked devices, and enables power delivery to the luminaires 10A-F only after all devices of the control group 8 are discovered, and all of the following conditions are confirmed in the system. First, a healthy hardware status of each device of the control group 8 broadcasting on the disinfection light control network 7, meaning all devices are discovered and communicating with other devices. Second, a healthy network status between each device in the antimicrobial system 1, for example no errors, dropped packets, nor significant noise detected. Third, all room entry sensors 45A,F are functional. Fourth, no room occupancy sensor type of room sensors 45B-E detects sending occupancy signals 170F of FIG. 6. Fifth, no entry sensor type of room sensors 45A,F detect sending room state signals 170F of FIG. 5 of indicating human(s) 185 (e.g., people) or animals are present in the vicinity 180 of the physical space. Sixth, all arming switches 56A-B are enabled. Seventh, all security challenge devices 1101A-B are enabled.

Figure 8:
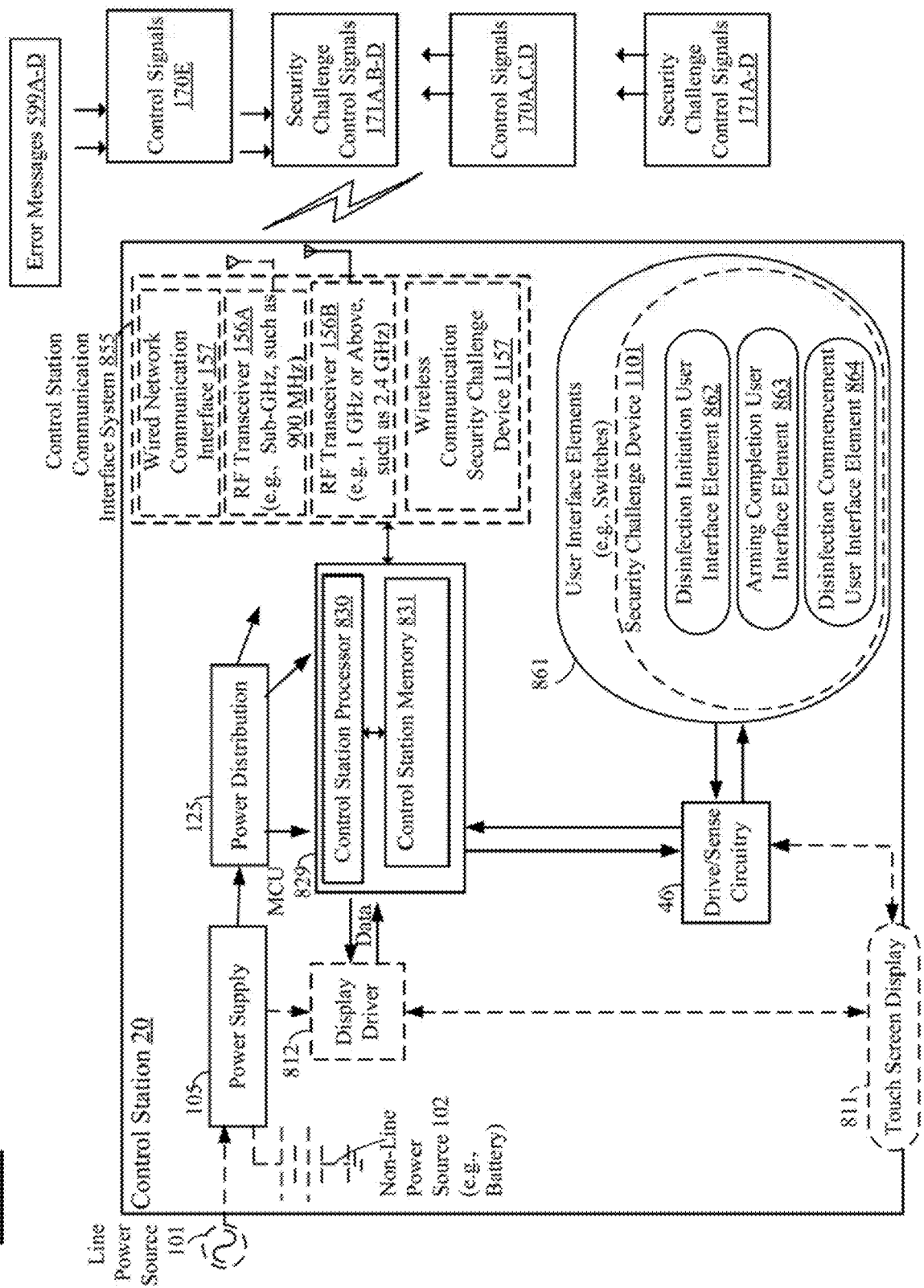
FIG. 8 is a block diagram of a control station device of the antimicrobial system.
Figure 11:
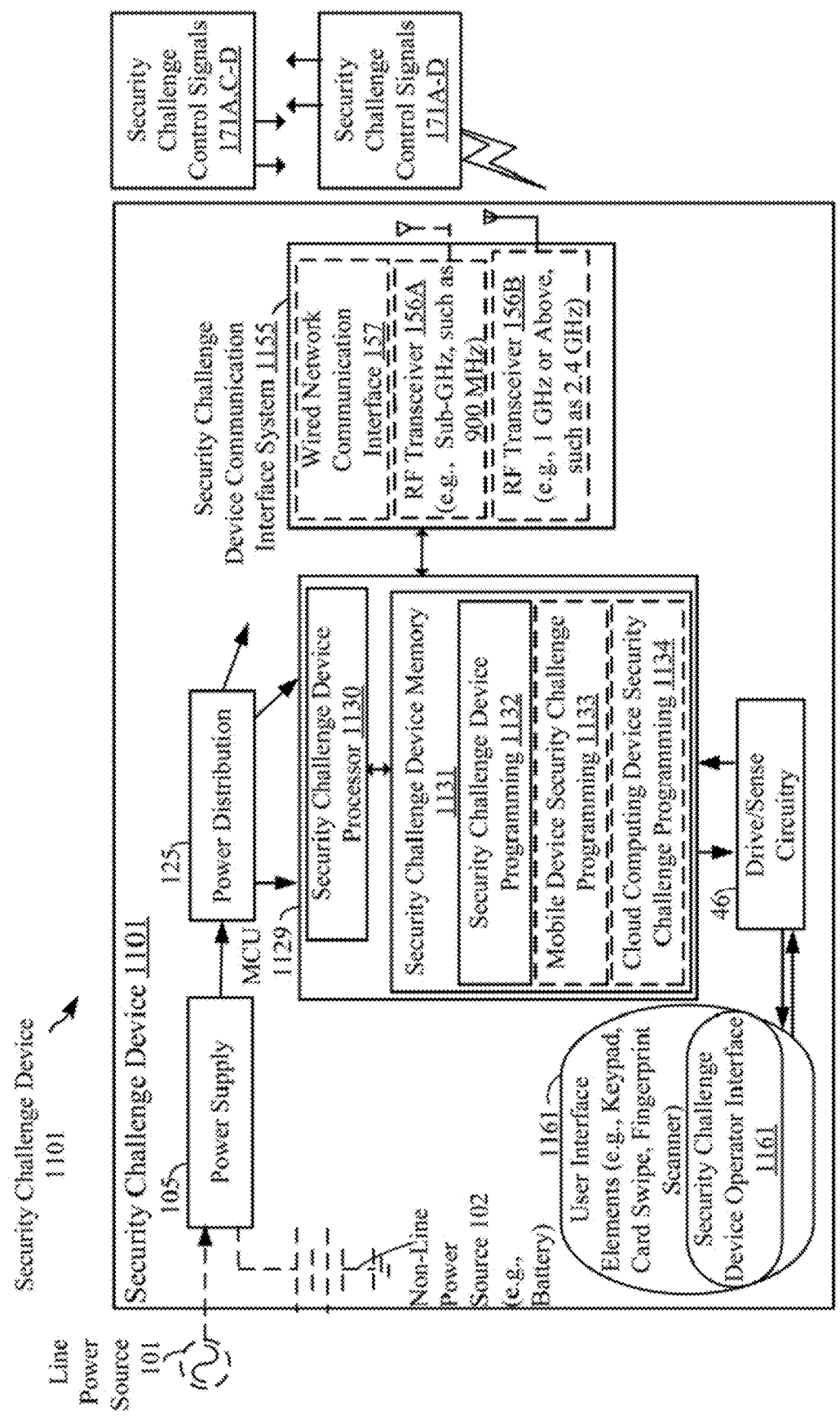
FIG. 11 is a block diagram of a security challenge device of the antimicrobial system.
Figure 12A:
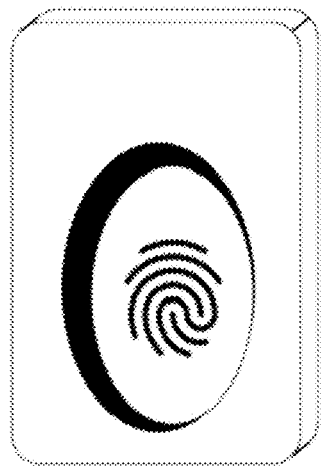
FIG. 12A is an example security challenge device with a fingerprint reader as the security challenge device operator interface.
Figure 12B:
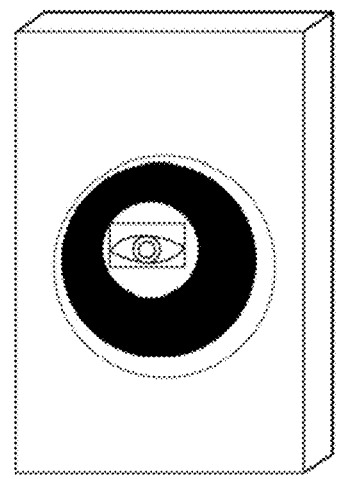
FIG. 12B is an example security challenge device with a retinal scanner as the security challenge device operator interface.
Figure 12C:
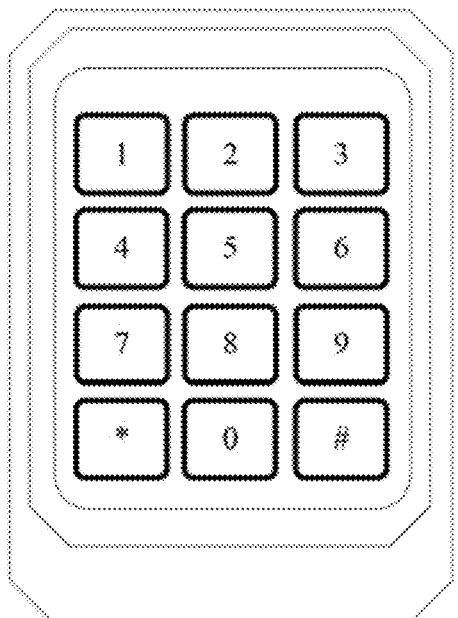
FIG. 12C is an example security challenge device with a keypad as the security challenge device operator interface.
Figure 12D:
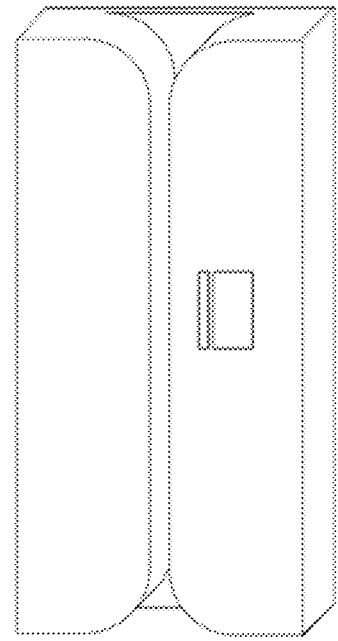
FIG. 12D is an example security challenge device with a card swipe reader as the security challenge device operator interface.

Another example of an additional safeguard to guard against inadvertently powering the luminaires 10A-F that emit disinfection light 17 is the use of a security challenge device 1101, which is shown in more detail in FIGS. 11 and 12. In this example, the security challenge device 1101A is embedded within the control station 20, but security challenge devices 1101 can be optionally placed in any of the room sensors 45A-F, luminaires 10A-D, switching device 110 and relay packs 111, 112, arming switches 56A-B, a mobile device 25, or even as a standalone component that is separately interactable from the other members of the control group 8. In this example, a second security challenge device 1101B is present in the first arming switch 56A. The antimicrobial system may have one security challenge device 1101A to generate a first security challenge response signal 171A, or multiple security challenge device 1101A-B to generate a second or more security challenge response signal 171D. Each member of the control group 8, along with the mobile device 25 and the cloud computing device 266, could have a security challenge device 1101. Additionally, the types of security challenge devices 1101 within the antimicrobial system 1 can vary, including between elements such as arming switches (e.g. a first arming switch 56A may have a retinal scanner 1206, while a second arming switch 56B may have a card swipe reader 1216. Generally, the security challenge device 1101 is a keyswitch (a user interface device which requires an external physical object, such as a key, RFID- or NFC-based access badge, or mobile phone equipped with BLE, WiFi, or NFC) which is part of the switches 861 of the access control station 20 and/or as the arming switches 56A-B that can be networked in the antimicrobial system 1. The keyswitch is a type of security challenge device 1101, and any type of security challenge device 1101 may be used to guard against inadvertently powering the luminaires 10A-F that emit disinfection light 17. A security challenge device 1101 challenges an operator to, by some means, prove that they are authorized to interact with the antimicrobial system 1 in the manner in which the operator is attempting to perform. Some examples of security challenge devices 1101 beyond a keyswitch are presented in FIG. 12, and can include a keypad 1211 or code entry device for numeric code or password authentication. In FIGS. 6, 7, and 8, a near field communication (NFC), Bluetooth (BLE), or Wi-Fi wireless communication security challenge device 1157 is shown. The wireless communication security challenge device may communicate with a mobile device 25 that is in the possession of and has authorized the operator. In FIGS. 4A and 4B, a visible light communication (VLC) security challenge device 1118 is shown. Security challenge devices 1101 including the subset of wireless communication security challenge devices 1157, VLC security challenge device 1118, and a mobile device security challenge device 1125 (described below) may include: a fingerprint reader configured to determine whether the fingerprint of the operator is within a listing of authorized fingerprints; a retinal scanner configured to determine whether the retinal scan of the operator is within a listing of authorized retinas; a facial recognition camera configured to determine whether a facial scan of the operator is within a listing of authorized faces; or any combination of the above. The combinations may be spread across functions; for example the arming switches 56A-B may require a fingerprint scan, but the control module 20 may require a password and a NFC communication with an authorized mobile device 25 which itself has authorized the operator via a facial scan. Some other examples of security challenge devices 1101 include mobile security challenge device 1125, where the security challenge is completed within a mobile device 25 and the security challenge response signal is forwarded to the rest of the antimicrobial system 1, and a network security challenge device 1135, where the security challenge input is collected elsewhere in the antimicrobial system, but evaluated within the network security challenge device 1135 to produce the security challenge response signal 171A.

Each control device of the control group 8 is physically connected to the disinfection light network 7, which can be a wired network via communication wires or cables (ex: CAT5 cable) or enabled for wireless network communication (ex: BLE, Wi-Fi, etc.). Therefore, the antimicrobial system 1 may comprise of all wired connected control devices, wireless only connected devices, or hybrid combination of both wired and wireless control devices. The room sensors 45A-F can include a traditional passive infrared motion sensor (PIR) enhanced with microphonics, or an audio detector circuit, for improved reliability of motion and occupancy sensing. In other embodiments, the motion sensors of the room sensors 45A-F may be based on ultrasonic, UWB, radar, or other motion sensing technologies.

The room sensors 45A-F may be further improved with a proximity and ranging sensor based on radar, UWB, BLE, WiFi or active infrared based technology in order to count occupants during regular room usage time of the vicinity 180 of the physical space 2, so that this information can be processed by the control group 8 to automatically calculate the required dosage disinfection time necessary to sanitize the room. The room sensors 45A-F (e.g., motion sensors) may be integrated in the luminaires 10A-F to simplify the system installation and reduce cost by reducing or eliminating the need for ceiling and wall mounted sensors. Similarly, the primary relay pack 111 and safeguard relay pack 112 may be separate devices embodied in a switching device 110, which control power to the driver circuit 11 of the luminaires 10A-F. Alternatively, primary relay pack 111, safeguard relay pack 112, or both may be integrated into the luminaires 10A-F, room sensors 45A-F, or wall switches including the control station 20 and arming switching 56A-B.

An integrated luminaire 10A-F occupancy/motion sensor or external power pack 111 of the switching device 111 may include a dimming circuit to reduce power from the driver circuit 11, or ballast, regulating voltage, current and/or power delivered to UVC light source. A lamp lumen depreciation algorithm may be implemented to extend the expected life of the disinfection light source 16 and ensure adequate disinfection light 17 levels over the life of the fluorescent or LED lamps. One example of the algorithm implementation starts with an 80% initial dimming intensity and gradually increases the output level to 100% over the extended lifetime of the disinfection light source 16. An alternate approach would extend the disinfection period based on the lumen depreciation of the disinfection light source 16 as it ages. These two approaches may also be combined by, for example, increasing the dimming intensity over a first period of time, then increasing the disinfection period once the dimming level has reached 100%. The room sensor(s) 45A-F or relay packs 111, 112 may be equipped with a dimmer circuit to directly control voltage, current and/or power to UVC lamp. Alternatively, the room sensor(s) 45A-F may send a signal to the ballast or driver circuit 11 via any of the analog or digital dimming signals known to the art (e.g. 0-10V or 4-20 mA analog low voltage, forward or reverse phase cut line voltage, or DALI, DMX, BACnet/IP, LONWORKS, KNX, BLE or similar wired or wireless digital control signal) to instruct the ballast or driver circuit 11 controlling the respective luminaire 10A-F to adjust the voltage, current and/or power delivered to the lamp.

The control station 20, relay packs 111,112, or a supervisory controller may be configured to record and report dosage periods with a date and time stamp information for audit purposes. This data may be displayed on a touch screen display 811 in FIG. 8 of the control station 20, or transmitted to computer, remote server, smart phone, or cloud data storage within a cloud computing device 266.

As shown, each of the luminaires 10A-F include an on-board luminaire control circuit 12, such as a micro-control unit (MCU), which is shown in more detail in FIG. 4A. The luminaire control circuit 12 includes a luminaire memory 131 (volatile and non-volatile) and a central processing unit (CPU) 130. As shown, the control circuit 12 of the luminaires 10A-N is coupled to a driver circuit 11 that controls light source operation of a disinfection light source 16 and an optional general illumination light source 18. Room sensors 45A-F have a micro-control unit (MCU) 629 coupled to drive/sense circuitry 46 operable to control detectors 47 (e.g., occupancy sensors). The control station 20 has an MCU 829 that includes a sense circuit 46 operable to control switches 861. Shown in further detail in FIG. 8, the switches 861 of the control station 20 include a disinfection initiation user interface element 862, an arming completion interface user element 863, and a disinfection commencement user interface element 864.

Luminaires 10A-F and the control group 8 can communicate control signal(s) 170A-N and security challenge control signal(s) 171A-D for the disinfection light 17 over a wireless disinfection light control network 7 (e.g., 900 MHz) and accordingly each include a first radio 156A in the sub-GHz range. A variety of control signals 170A-N and security challenge control signals 171A-D for the disinfection light 17 are transmitted over wireless disinfection light control network 7, including, for example, to turn the disinfection light source 16 on/off and sensor trip events. In a first example, each luminaire 10A-F and control group 8 member is also equipped with a second above 1 GHz radio 156B (e.g., near range 2.4 GHz Bluetooth Low Energy (BLE)) that communicates over a separate commissioning network (not shown) for purposes of commissioning and maintenance of the antimicrobial system 1, however no control signals 170A-N or security challenge control signals 171A-D for the disinfection light 17 pass over this commissioning network. In a second example, wireless disinfection light control network 7 and commissioning network are combined, such that both control signals 170A-N and security challenge control signals 171A-D for disinfection light 17 and commissioning/maintenance information pass over the above 1 GHz range wireless communication band. In the second example, luminaires 10A-F and the control group 8 are only equipped with the above 1 GHz radio 156B for communication of control signals 170A-N and security challenge control signals 171A-D for disinfection light 17 and commissioning/maintenance information.

Alternatively, the disinfection light control network 7 may be partially or completely wired, and the luminaires 10A-F and the control group 8 communicate over wired data connections. Furthermore, some control signals 170A-N and security challenge control signals 171A-D can be communicated over energy-providing wired connections, for example in the presence or absence of voltage or current, or in the timing of the presence or absence of voltage or current.

The antimicrobial system 1 can be provisioned with a mobile device 25 that includes a commissioning/maintenance application for commissioning and maintenance functions of the antimicrobial system 1. For example, a mobile device 25 enables mobile commissioning, configuration, and maintenance functions and can be a PDA or smartphone type of device with human interfacing mechanisms sufficient to perform clear and uncluttered user directed operations. A mobile device 25 runs mobile type applications on iOS, Android, or Windows 10 operating systems and commissioning/maintenance application to support commissioning.

Antimicrobial system 1 can leverage existing sensor and fixture control capabilities of Acuity Brands Lighting's commercially available nLight® wired product through firmware reuse. In general, Acuity Brands Lighting's nLight® wired product provides the lighting control applications. However, the illustrated antimicrobial system 1 includes a communications backbone and includes model-transport, network, media access control (MAC)/physical layer (PHY) functions. The sub-GHz communications of the wireless disinfection light control network 7 features are built on a near 802.15.4 MAC and PHY implantation with network and transport features architected for special purpose control and air time optimizations to limit chatter.

Antimicrobial system 1 can further include a gateway 220. The gateway 220 is a computing device that provides access between a wide area network (WAN) 255 and a local communication network, such as the disinfection light control network 7. The WAN 255 (e.g., Internet) can be a cellular network, optical fiber, cable network, or satellite network that can be connected to via Ethernet, for example. The gateway 220 may provide routing, access, and other services for the luminaires 10A-F and the control group 8 members residing at the physical space 2, for example.

Antimicrobial system 1 can still further include a cloud computing device 266, and the cloud computing device 266 resides off-premises 265 (e.g., cloud) meaning the cloud computing device 266 is a remote computing device or server hosted on the Internet to store, manage, and process data, rather than the local gateway 220. The gateway 220, cloud computing device 266, or mobile device 25 can also be used to monitor and control (e.g., switch on/off) the disinfection light 17 of the luminaires 10A-F and other components of the antimicrobial system 1, such as control group 8 members. Gateway 220, cloud computing device 266, and mobile device 25 can receive and process data from the luminaires 10A-F and the control group 8 members.

Antimicrobial system 1 can be deployed in standalone or integrated environments. Antimicrobial system 1 can be an integrated deployment, or a deployment of standalone groups with no gateway 220. Antimicrobial system 1 may comprise a mix and match of various indoor systems, wired lighting systems (nLight® wired), wireless lighting systems (nLight® AIR), emergency, and outdoor (dark to light) products that are networked together to form a collaborative and unified lighting solution. Additional control devices and lighting fixtures, gateway(s) 220 for backhaul connection, time sync control, data collection and management capabilities, and interoperation with the Acuity Brands Lighting's commercially available SensorView™ product may also be provided.

The instructions, programming, or application(s) implementing the distributed control programming described herein may be software or firmware used to implement any other device functions associated with luminaires 10A-F, control group 8 members, network controller (e.g., gateway 220), and cloud computing device 266. Program aspects of the technology may be thought of as "products" or "articles of manufacture" typically in the form of executable code or process instructions and/or associated data that is stored on or embodied in a type of machine or processor readable medium (e.g., transitory or non-transitory), such as memory 131, 191, 531, 631, 731, 831, 931 1131, 1331, 1731, 2031, 2131; a memory of gateway 220; and/or another computer used to download or otherwise install such programming into the with luminaires 10A-F, control group 8 members, network controller (e.g., gateway 220), cloud computing device 266, or a transportable storage device or a communications medium for carrying program for installation in the luminaires 10A-F, control group 8 members, network controller (e.g., gateway 220), and/or cloud computing device 266.

FIG. 1B depicts tying the control of a disinfection light source 17 of the luminaire 10 to the position of an occupant (e.g., human 185) in the physical space 2. In the example of FIG. 1B, the disinfection light 17 emission is stopped as the human 185 moves into a respective vicinity 180A-D of a respective luminaire 10A-D.

In the example of FIG. 1B, the physical space 2 on-premises (e.g., interior to a building or exterior) is comprised of four luminaires 10A-D in a respective vicinity 180A-D each operating independently of one another. The vicinities 180A-D are at different respective physical locations 199A-D throughout the physical space 2. Specifically, vicinity 180A is at a first physical location 199A with location coordinates (1,1); vicinity 180B is at physical location 199B with location coordinates (2,1); vicinity 180C is at physical location 199C with location coordinates (1,2); and vicinity 180D is at physical location 199D with location coordinates (2,2). Each luminaire 10A-D operates in a respective vicinity 180A-D of the physical space 2 to disinfect a respective surface(s) 188A-D and respective air 189A-D of a respective target pathogen 187A-D.

Each luminaire 10A-D can have a respective room sensor 45A-D (e.g. occupancy sensor). For example, as shown in FIG. 1B, luminaire 10A along with room sensor 45A are located in a respective vicinity 180A at physical location 199A. Similarly, luminaire 10B along with room sensor 45B are located in a respective vicinity 180B at physical location 199B. Luminaire 10C along with room sensor 45C are located in a respective vicinity 180C at physical location 199C. Luminaire 10D along with room sensor 45D are located in a respective vicinity 180D at physical location 199D.

As shown, a human 185A is in vicinity 180A and another human 185D is in vicinity 180D. Hence, luminaires 10A-D are controlled, such that only disinfection light source 16B of luminaire 10B emits disinfection light 17B and disinfection light source 16C of luminaire 10C emits disinfection light 17C because only vicinities 180B and 180C are unoccupied by humans 185.

Controlling the luminaires 10A-D by occupant position allows a physical space 2, such as a large room (e.g., store), to only deactivate the luminaires 10A-D in a part of the room where a human 185 is suspected of being and not significantly irradiating that part of the physical space 2. A human 185 in the non-irradiated part of the large room will not be irradiated and this allows the physical locations 199B, 199C of the large room to continue being disinfected.

Figure 2B:
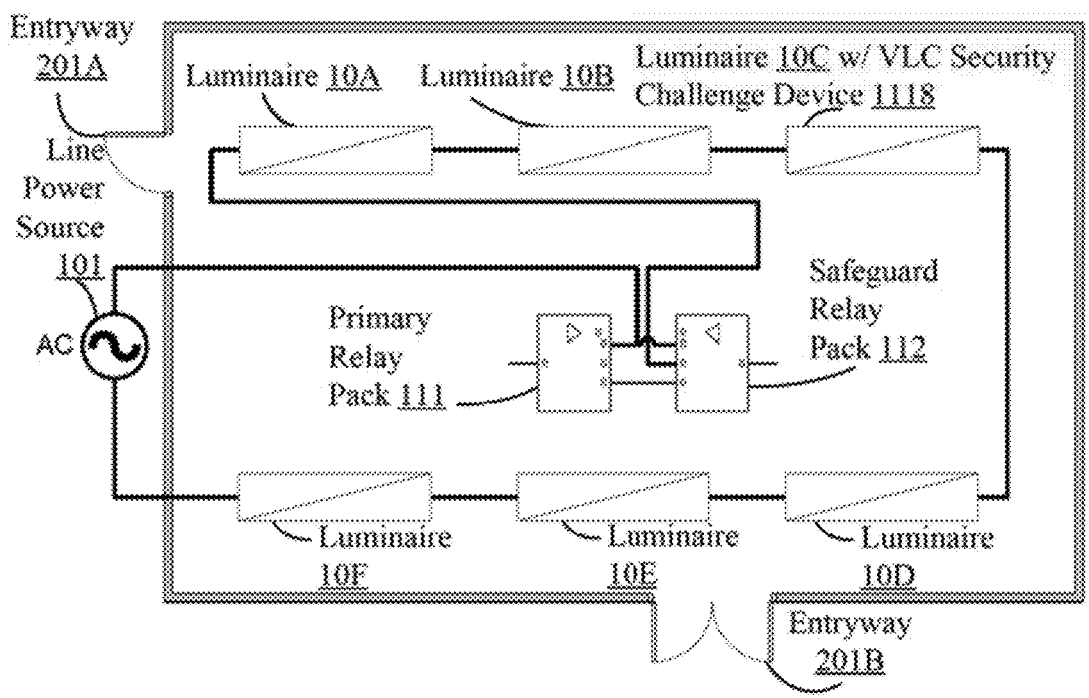
FIG. 2B is a high-level functional block diagram of an example of an antimicrobial system that includes luminaires with external sensors and electrical connections.

FIGS. 2A-B are high-level functional block diagrams of an example of an antimicrobial system 1 that includes luminaires 10A-F with external sensors. FIG. 2A illustrates the data connections between the elements within the antimicrobial system 1, and FIG. 2B illustrates the electrical connections between the elements within the antimicrobial system 1. This antimicrobial system 1 is designed to utilize disinfection light 17 to disinfect a vicinity 180, while only disinfecting that vicinity 180 where there are not humans 185 within the vicinity 180. This antimicrobial system 1 ideally meets safety certification standards for germicidal systems, in particular by relying on multiple redundant systems to prevent a human 185 from receiving unsafe dosages of disinfection light 17.

FIG. 2A shows an antimicrobial system 1 with a switching device 110 that includes a pair of relay packs: a primary relay pack 111 and a safeguard relay pack 112. The primary relay pack 111 as shown in FIG. 5 has a primary relay pack regulator 511 by which is can provide or withhold line voltage and current from the luminaires 10A-F via the primary relay pack regulator 511, thereby controlling the luminaires 10A-F. The luminaires 10A-F and line voltage and current control are further described in FIG. 2B.

The antimicrobial system 1 further includes six room sensors 45A-F: in particular, two room sensors are entry sensors 45A, F near the two entryways 201A-B, and the remaining four are room sensors 45B-E mounted in the ceiling. In this example, these six room sensors 45A-F form part of the disinfection light control network 7 by being wired together, for example via an RS485 or Ethernet connection. These six room sensors 45A-F are also joined to the switching device 110 by a wired data connection, which brings the switching device 110, primary relay pack 111, and safeguard relay pack 112 onto the disinfection light control network 7. The entry sensor room sensors 45A, F are located near the entryways 201A-B to the physical space 2 containing the vicinity 180, and these room sensors 45A, F are pointed to detect if a human 185 enters or leaves the physical space 2. The four remaining room sensors 45B-E are ceiling-mounted, and are pointed to generally detect motion within the physical space 2. The room sensors 45A-F are, when necessary, pointed with overlapping sensed areas, rather than pointed with gaps between a sensed area and the area of the physical space 2.

Additionally, two arming switches 56A-B are placed within the physical space 2. Though they are located near the entryways 21A-B, the arming switches 56A-B can be placed anywhere that, after a human 185 stands in the nearby surrounding area of each arming switch 56A-B and performs a visual inspection, the entire physical space 2 has been visually inspected for occupants. More arming switches 56 can be used than two arming switches 56A-B, and if only one arming switch 56A is needed to meet the standing visual inspection requirement, only one arming switch 56A is required. More arming switches 56 than are minimally required may be used, in order to enforce improved visual inspection by the operator performing the visual inspections in front of the arming switches 56A-B.

The arming switches 56A-B have additional components as described in FIG. 7, but can also minimally be a user interface element, such as simple inspection switch 761: one which sends a visual inspection signal 170B when the arming switch 56A is triggered, and which sends no signal when the arming switch 56A is not triggered. The example arming switches 56A-B are simple on/off switches, but the inspection switch 761 could by any kind of user interface element; the arming switches 56A-B could require a key, or a security challenge device operator interface 1161 such as a passphrase or PIN entry device like a keypad 1211, a badge scan or swipe into a card swipe reader 1216, or fingerprint scan by a fingerprint reader 1201, all shown in greater detail in FIGS. 11 and 12. Additionally, an arming switch 56A can implement a different security challenge, or could implement no security challenge or key requirement at all, even if another arming switch 56B implements a security challenge or key requirement. The inspection switch 761 could also be implemented virtually, as a digital object an operator interacts with via a computing component like the touch screen device 811 of FIG. 8.

The control station 20 in this example is connected to the arming switch 56A by a wired data connection, and requires a key to begin the disinfection commencement operation. The control station 20 starts at least three operation: the arming initiation operation, the arming completion operation, and the disinfection commencement operation, and can use separate triggers, switches, or user interface elements for each operation as further described in FIG. 8. Furthermore, in this example the disinfection commencement operation requires the entry of a password, as the control station 20 includes a keypad 1211 security challenge operator interface 1161 for the security challenge device 1101 (shown in further detail in FIGS. 11 and 12.) Though in this example, the password must be entered into the keypad 1211 by an operator to start the disinfection light 17, any or all of the three operations can require a key or security challenge, implemented in a security challenge device 1101 much like the arming switch 56A-B. These operations can be performed by user interface elements, such as a labeled mechanical button, a keypad 1211, or a graphical user interface element, among others.

These control group 8 members communicating over wired data connections on the disinfection light control network 7 are designed to perform an authenticated safe lockout protocol 1001 of FIG. 10A, confirming that no human 185 is within the physical space 2 once the disinfection light 17 is activated. Once the authenticated safe lockout protocol 1001 is completed, the switching device 110 provides power to the luminaires 10A-F.

FIG. 2B shows the electrical wiring of the antimicrobial system 1. Here, a line power source 101, with enough voltage and amperage to run the antimicrobial system 1 and all six luminaires 10A-F, has a power line running to both the primary relay pack 111 and the safeguard relay pack 112. Line power source 101 is the form of electrical power that consumers use when they plug in domestic appliances, televisions and electric lamps into wall outlets. A line power source 101 is referred to as grid power, wall power, and domestic power, alternating current (AC) electric power produced and delivered via AC mains to homes and businesses. Line power source 101 conveys line power (e.g., 120-volts alternating current (VAC), 240-VAC, or 277-VAC), sometimes referred to as "household power," "household electricity," "house current," "powerline," "domestic power," "wall power," "line power," "AC power," "city power," "street power" that is produced by an electric utility provider. Non-line power source 102 in the example is a battery, solar panel, or any other AC or DC source (e.g. a generator) that is not line powered.

A small communication line runs from the primary relay pack 111 to the safeguard relay pack 112, which exists in part to coordinate electrical flow to the luminaires 10A-F. Both the primary relay pack 111 and the safeguard relay pack 112 must agree that both the primary relay pack 111 and the safeguard relay pack 112 are operating correctly before powering the luminaires 10A-F, and the primary relay pack 111 and the safeguard relay pack 112 can perform this analysis using this small communication line. Another power line runs from the safeguard relay pack 112 to and through the luminaires 10A-F, completing a circuit back at the line power source 101.

The safeguard relay pack 112 confirms that the primary relay pack 111 is working correctly by checking for voltage coming from the primary relay pack 111 at any time that the primary relay pack 111 is open and not supposed to be providing voltage. At least one concern is that the primary relay pack 111 regulator 511 has fused closed, and that the primary relay pack 111 cannot stop providing voltage to the luminaires 10A-F. A reasonable time to check whether the primary relay pack 111 is inappropriately sending voltage and therefore electricity is during the authenticated safe lockout protocol 1001, because during the authenticated safe lockout protocol 1001 (i.e. while confirming the physical space 2 has no humans 185 present) the luminaires 10A-F should not be emitting disinfection light 17, and the primary relay pack 111 should not be providing power to the luminaires 10A-F. Therefore, if the safeguard relay pack 112 detects too much voltage when the luminaires 10A-F should not be emitting disinfection light 117, the primary relay pack 111 is not operating correctly. The safeguard relay pack 112 also determines whether the regulator 511 of the primary relay pack 111 has fused or broken open, by determining whether voltage is provided by the primary relay pack 111 soon after the beginning of the authenticated safe lockout protocol 1001 has completed and the commencement operation has been signaled by the control station 20. If the safeguard relay pack 112 does not detect enough voltage when the luminaires 10A-F should be emitting disinfection light, then the primary relay pack 111 is not operating correctly.

The primary relay pack 111 confirms that the safeguard relay pack 112 is working correctly by checking the current drawn from the primary relay pack 111 through the safeguard relay pack 112 when the primary relay pack 111 is providing voltage: if the primary relay pack 111 does not detect an increase in current drawn when the safeguard pack 112 is supposed to be closed and providing electricity to the luminaires 10A-F, then the regulator 911 of the safeguard relay pack 112 has fused or broken open, cannot complete a circuit back to the line power source 101, and the safeguard relay pack 112 is not operating correctly. Alternatively, when the antimicrobial system 1 determines that power should no longer be provided to the luminaires 10A-F, the antimicrobial system 1 is designed to first open the regulator 911 of the safeguard relay pack 112. Once the regulator 911 of the safeguard relay pack 112 is supposed to be open, the primary relay pack 111 checks whether the current drawn has decreased. If the current drawn by the safeguard relay pack 112 remains at the level commensurate to the luminaires 10A-F emitting disinfection light 17 while the luminaires 10A-F should not be emitting disinfection light 17, then the regulator 911 of the safeguard relay pack 112 has fused closed, and the safeguard relay pack 112 is not operating correctly.

The primary relay pack 111 and safeguard relay pack 112 are also capable of determining if any of the luminaires 10A-F are not emitting disinfection light 17. The current drawn by each luminaire 10A-F is material, and therefore both the primary relay pack 111 and the safeguard relay pack 112 can determine if the current drawn when the luminaires 10A-F should be emitting disinfection light 17 is lower than when the luminaires 10A-F were last commissioned, configured, or maintained. For example, if the current drawn when both the regulator 511 of the primary relay pack 111 and the regulator 911 of the safeguard relay pack 112 are closed is 50% lower than the current drawn when the antimicrobial system 1 was last maintained and the peak current draw was ascertained, then the antimicrobial system 1 can determine that three of the six luminaires 10A-F are not drawing current and therefore are not emitting disinfection light 17. It is also possible that there could be other unexpected errors causing the drop in current usage, so the antimicrobial system 1 may signal an error message 599A-D when the current experienced deviates from the expected current. It is also known that the luminaires 10A-F may draw more or less current as they approach their rated lifetime limit; this change in current draw can be expected, and tolerances within the primary relay pack 111 and safeguard relay pack 112 can be configured to account for this change in current usage. A first error message 599A indicates an issue with the primary relay pack 111, a second error message 599B indicates an issue with the luminaires 10A-F, a third error message 599C indicates an issue with the safeguard relay pack 112, and a fourth or more error message 599D indicates an error with another component of the antimicrobial system 1. Switching device 110 can detect when one or multiple luminaires 10A-F have failed by monitoring current and produce the second error message 599B based on the monitored current. These error messages 599A-D can be displayed on any control group 8 device, for example on a touch screen display 811 on the control device 20. Alternatively or additionally, the error messages 599A-D can be sent to an off-premises 265 device, such as a cloud computing device 266 via the network controller 220.

To begin the authenticated safe lockout protocol 1001 in this example, first an operator must move to the control station 20 to produce an arming initiation signal based 170A on a first input. In this example, an operator input can be pressing the disinfection initiation user interface element 862, which is a button. Next, in this example within a limited time of five minutes, the operator must inspect the physical space 2 by travelling to each arming switch 56A-B, and produce a visual inspection signal 170B based on a second input for each arming switch 56A-B. An operator can produce the visual inspection signals 170B by pressing the inspection switch 761, which is a button in this example. After producing a visual inspection signal 170B from each arming switch 56A-B, the operator returns to the control station 20 and produces an arming completion signal 170C based on a third input. In this example, an operator can produce the arming completion signal 170C by pressing the arming completion interface user element 863, which is a button. Here, the operator is an individual person; however, the operator can be multiple people sharing duties, such as a first operator performing a visual inspection by one arming switch 56A and a second operator performing a visual inspection by another arming switch 56B. Additionally, the control station 20 could be at a substantial distance from the physical space 2, and multiple operators may be required to coordinate over an alternative network (such as Wi-Fi or a cellular network) to inform an operator near the control station 20 that the arming switches 56A-B have all been activated.

At this point, the primary relay pack 111 has received the arming initiation signal 170A that is ON, which indicates the primary relay pack 111 must begin tracking, counting, and confirming visual inspection signals 170B that are ON from each arming switch 56A-B. Once the arming completion signal 170C that is ON is received by the primary relay pack 111, the primary relay pack 111 compares the number of visual inspection signals 170B received since the arming initiation signal 170A was received, to the known number of arming switches 56A-B within the physical space 2. When these two numbers are equal, the primary relay pack 111 has determined that the tracked visual inspection signals 170B are ON, and that the physical space 2 has been inspected by an operator, and that the luminaires 10A-F can operate within safety guidelines.

In addition to an operator inspection, the primary relay pack 111 will signal to the room sensors 45A-F to perform a sweep of the physical space 2, in order to quickly ascertain whether a human 185 is still in the physical space 2 despite the positive inspection results from the arming switches 56A-B from the operator. The room sensors 45A-F perform a sweep by attempting to detect occupancy via the detectors 47 of the room sensors 45A-F for a short period of time, for example within five seconds.

After the room sensors 45A-F perform a sweep of the physical space 2 and confirm the physical space 2 is empty of humans 185, the primary relay pack 111 indicates the control station 20 may enable the disinfection commencement user interface element 864 with an enablement signal 170E. The enablement signal 170E may light up a "Safeguards OK" button on the control station 20 when the control station 20 includes a user information display such as a pilot light status indicator or a touch screen display 811 as in FIG. 8.

Before this point, any human 185 attempting to utilize the disinfection commencement user interface element 864 would be unable to start the disinfection light 17 emission from the luminaires 10A-F, even if the human 185 had proper authorization and a required password for the keypad 1211. The disinfection light 17 emission from the luminaires 10A-F can only be started after both an operator confirms via the arming switches 56A-B that there are no humans 185 within the physical space 2 and the room sensors 45A-F via a sweep of the physical space 2 confirm that there are no humans 185 within the physical space. In some examples, an un-enabled disinfection commencement user interface element 864 is implemented by having the primary relay pack 111 and safeguard relay pack 112 ignore any disinfection commencement signal 170D sent by the disinfection commencement user interface element 864: this example is more likely to be used when the disinfection commencement user interface element 864 is a simple button. However, in example where the disinfection commencement user interface element 864 includes a status indicator, such as a light capable of emitting red (un-enabled) or green (enabled), then the enablement signal 170E will update that status indicator, and alert the operator that the disinfection commencement user interface element 864 is enabled.

With the disinfection commencement user interface element 864 enabled, the operator can enter the password into the security challenge device 1101 via the security challenge device operator interface 1161 (e.g. the keypad 1211) associated with the antimicrobial system 1 as a fourth input. This fourth input is a password entry and is a security challenge input. Entering a valid password into the keypad 1211 is the security challenge. The security challenge device 1101 receives the security challenge input from the operator via the security challenge device operator interface 1161, and in response to receiving the security challenge input, generates a security challenge response signal 171A. This security challenge response signal 171A will either enable the primary relay pack 111 to activate the antimicrobial system 1, or it will indicate an invalid security challenge input. In this example, the operator has entered a valid security challenge input, and the antimicrobial system 1 will be activated. Activating the antimicrobial system 1 in this example simply means that, in response to the primary relay pack 111 determining that the tracked visual inspection signal 170B is on, that the room sensors 45A-F did not detect any humans 185, that the disinfection commencement signal 170D was sent, and the security challenge response signal 171A indicates a valid security challenge input was inputted, controlling power to the luminaires 10A-F to emit the disinfection light 17. The primary relay pack 111 satisfies this role by providing the luminaires 10A-F with enough electricity to power their disinfection light sources 16: the luminaires 10A-F may have additional criteria to be satisfied before the luminaires 10A-F will produce disinfection light 17.

The safety of humans 185 that may enter the physical space 2 or humans 185 that were undetected by the operator or the room sensors 45A-F needs to be maintained. Therefore, while the primary relay pack 111 is providing electricity to the luminaires 10A-F emitting disinfection light 17, if the room sensors 45A-F detect any humans 185 in the physical space 2, the detecting room sensor 45A sends a room state signal 170F via the disinfection light control network 7, and the primary relay pack 111 and the safeguard relay pack 112 stop providing electricity to the luminaires 10A-F, and the luminaires 10A-F stop emitting disinfection light 17.

Barring the detection of human(s) 185 within the physical space 2, the luminaires 10A-F will continue emitting disinfection light 17 until the individual luminaires 10A-F determine that the vicinity 180 into which the individual luminaires 10A-F emit disinfection light 17 are sufficiently disinfected. This determination may be based upon logic that is further described in FIG. 4A. In addition, the primary relay pack 111 and safeguard relay pack 112, as well as the control station 20 may determine whether the luminaires 10A-F have emitted sufficient disinfection light 17, in this example based upon the expiration of an emission timer 541. The emission timer 541 of the primary relay pack 111 is the primary emission timer 921 as show in FIG. 9, and the emission timer 541 of the safeguard relay pack 112 is the safeguard emission timer 922. The primary emission timer 921, the safeguard emission timer 922, as well as the emission timer 541 of the control station 20 may be more conservative than the timers of the luminaires 10A-F, and act as a maximum time for the luminaires 10A-F to emit disinfection light 17 in order for the primary relay pack 111 or the safeguard relay pack 112 to detect if any luminaire 10A-F is malfunctioning and emitting disinfection light 17 for too long. The emission of disinfection light 17 by the luminaires 10A-F can also be stopped by a human 185 signaling via the control station 20 that the disinfection process must be ended prematurely, for example by pressing any of the switches 861, including the disinfection initiation user interface element 862, arming completion interface user element 863, or disinfection commencement user interface element 864.

Figure 3:
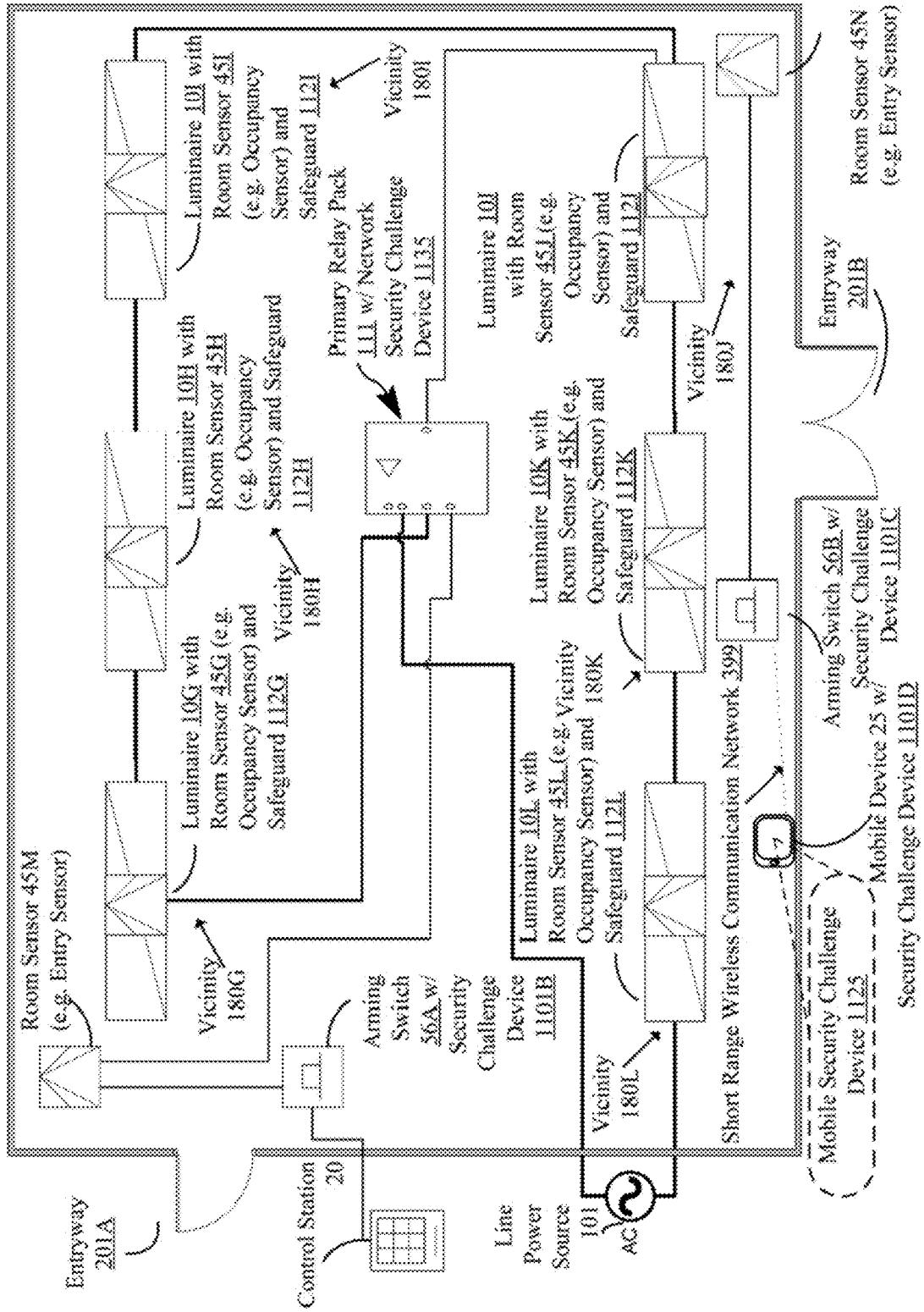
FIG. 3 is a high-level functional block diagram of an alternative example of an antimicrobial system that includes luminaires with integrated sensors and integrated switching devices.

FIG. 3 is a high-level functional block diagram of an alternative example of an antimicrobial system 1 that includes luminaires 10G-L with integrated room (e.g. occupancy) sensors 45G-L and integrated switching devices (e.g. safeguard relay packs 112G-L.) This example is similar to the example of FIGS. 2A-B, except in FIG. 3 each luminaire 10G-L has a room sensor 45G-L integrated into the luminaire 10G-L, and each luminaire 10G-L has a safeguard relay pack 112G-L integrated into the luminaire 10G-L. This allows for slightly different behavior as compared to FIGS. 2A-B.

The first difference between FIGS. 2A-B and FIG. 3 is that in the example of FIG. 3, each luminaire 10G-L is capable of verifying whether the primary relay pack 111 is operating correctly, using the embedded safeguard relay pack 112G-L. The luminaires 10G-L can detect voltage, and will be able to determine if voltage is being inappropriately provided by the primary relay pack 111 at all times. In this example, each luminaire 10G-L has a pass-through power line, so each luminaire 10G-L may determine whether the primary relay pack 111 is inappropriately providing voltage. The primary relay pack 111 can also determine if the current drawn by the luminaires 10G-L is incorrect, and therefore whether one of the safeguard relay packs 112G-L within the luminaires 10G-L is working incorrectly. Depending upon wiring strategy, for example wiring in sequence or wiring in parallel, the primary relay pack 111 may be able to determine which particular luminaires 10G-L are working incorrectly.

A second difference in design between the examples of FIGS. 2A-B and FIG. 3 is that in the example of FIG. 3 the control station 20 has no security challenge device 1101, and the security challenge device 1101 is split into two security challenge devices 1101B-C between the arming switches 56A-B. These security challenge devices 1101B-C implement the wireless communication security challenge device 1157 shown in FIG. 7. These example wireless communication security challenge devices 1157 implement near-field communication (NFC). The mobile device 25 is placed within short range wireless communication range and communicates over the short range wireless communication network 399, a security challenge. This security challenge may be as simple as being within the short range wireless communication network 399, which the operator possessing the mobile device 25 de facto has validated. In such an example, the mobile device 25 generates the security challenge response signal 171A, again in this example enabling the primary relay pack 111 to control power to the luminaire 10 to emit the disinfection light 17 via the primary relay pack regulator 511. This security challenge will need to be completed twice, once at the security challenge device 1101B of arming switch 56A, and once at the security challenge device 1101C of arming switch 56B In addition, the mobile device 25 itself may pose an additional security challenge, by utilizing security challenge device 1101D. This security challenge device 1101D may for example perform facial recognition scans, require passwords, keycards presentation, or fingerprint validation, much like other security challenge devices 1101. This security challenge device 1101D may however require completion of a feature identification security challenge: a security challenge where the operator must identify a feature within the physical space 2 or within the vicinity 180. For example, the operator possessing the mobile device 25 may be asked to identify a light color emitted by the arming switch 56A-B they are interacting with, or a number displayed on a screen connected to the arming switch 56A-B. They may also be asked to identify a flashing pattern emitted by the general illumination light sources 18 of the luminaires 10G-L. This security challenge device 1101D of feature identification may be used in lieu of any other security challenge device 1101, and can potentially allow for the mobile device 25 to perform security challenge validation without being directly connected to the disinfection light control network 7. For example, rather than the mobile device 25 communicating the security challenge device response signal 171A to the primary relay pack 111, the mobile device 25 can instead communicate to the cloud computing device 266, using a network different from the disinfection light control network 7, such as a mobile data LTE network. The cloud computing device 266 can then forward the security challenge device response signal 171A to the primary relay pack 111. Furthermore, the cloud computing device 266 itself can act as the security challenge device 1101. This means that the mobile device 25, or any member of the control group 8, instead of performing the validation of the security challenge input and generating the security challenge device response signal 171A, could instead forward the security challenge input to the cloud computing device 266, and the cloud computing device 266 may act as the security challenge device 1101, with the cloud computing device 266 performing the validation of the security challenge input and generating the security challenge device response signal 171A A third difference in design between the example of FIGS. 2A-B and FIG. 3 is that in the example of FIG. 3 each luminaire 10G-L has a respective room (e.g. occupancy) sensor 45G-L. Each luminaire 10G-L having a respective room sensor 45G-L means that, once the authenticated safe lockout protocol 1001 (see FIG. 10A) has completed and the luminaires 10G-L are emitting disinfection light 17, if a particular luminaire 10G detects an occupant human 185, only luminaire 10G would be required to stop emitting disinfection light 17. This could be advantageous if the physical space 2 is particularly large, and it is difficult to complete sufficient disinfection before a human 185 inadvertently enters the secured physical space 2. If the room sensors 45M-N that are not integrated into a luminaire 10G-L detect an occupancy human 185, then all of the luminaires 10G-L stop emitting light as the primary relay pack 111 stops providing power to the luminaires 10G-L.

Furthermore, even though each luminaire 10G-L is capable of individually detecting an occupant human 185 and only stopping the emission of disinfection light 17 in the vicinity 180 of that luminaire 10G-L, the antimicrobial system 1 may nevertheless still behave like the example in FIG. 2A-B and stop all luminaires 10G-L from emitting disinfection light 17 if any luminaire 10G-L detects an occupant human 185 while the antimicrobial system 1 is emitting disinfection light 17.

If any of the luminaires 10G-L are connected to the disinfection light control network 7, and can communicate with the rest of the antimicrobial system 1, then more advanced behavior may be implemented: for example, a luminaire 10G that detects an occupant human 185 may communicate to neighboring luminaires 10H, L to also stop emitting disinfection light 17. If the disinfection light 17 is not within the visible light spectrum, if a luminaire 10I detects an occupant human 185, the antimicrobial system 1 may direct any luminaires 10G-I along a path to the entryway 201A to stop emitting disinfection light 17, and to additionally emit illumination light 19 as shown in FIG. 4A, potentially directing the occupant human 185 out of the physical space 2 while only requiring the antimicrobial system 1 to stop emitting disinfection light 17 from a minimum of luminaires 10G-I. This behavior assumes the human 185 will follow the illumination light 19 path made by the luminaires 10G-I, and not move into the vicinities 180J-L covered by other luminaires 10J-L with integrated room sensors 45.

FIG. 4A is a block diagram of a disinfection lighting device (e.g., luminaire 10) of the antimicrobial system 1. As shown, the luminaire 10 includes a disinfection light source 16 to emit a disinfection light 17, e.g., in a ultraviolet (UV) band for disinfecting a vicinity 180 of a physical space 2 of a target pathogen 187 that is exposed to the disinfection light 17. Generally, the UV band can cover the wavelength range 100-400 nanometers (nm), which is sub-divided into three bands: UVA (315-400 nm) UVB (280-315 nm) UVC (100-280 nm). In a first example, the UV band of the disinfection light 17 can be UVC spectrum between 200 nm to 280 nm wavelength. More specifically, the UV band of the disinfection light 17 can be UVC spectrum between approximately 200 nm to 230 nm. In another example, the UV band is approximately 222 nm or approximately 254 nm. In yet another example, the disinfection light 17 may be just outside of the UV band, such as the visible light spectrum between 405-430 nm.

Luminaire 10 includes a power supply 105 that is driven by a line power source 101 and optionally a non-line power source 102. Power supply 105 may include a magnetic transformer, electronic transformer, switching converter, rectifier, or any other similar type of circuit to convert an input power signal into a power signal suitable for a disinfection light source 16 and an optional general illumination light source 18. Luminaire 10 includes power distribution circuitry 125 driven by the line power source 101 or non-line power source 102. The power distribution circuitry 125 distributes power and ground voltages to the luminaire processor 130; luminaire memory 131; luminaire wireless radio communication interface system 155 (e.g., wireless transceivers); and optional on-board occupancy, motion, ozone, daylight, or audio sensor 45 to provide reliable operation of the various circuitry on the luminaire 10. Luminaire processor 130 includes a central processing unit (CPU) that controls the light source operation of the disinfection light source 16 and the optional general illumination light source 18. Luminaire memory 131 can include volatile and/or non-volatile storage.

In the case of luminaire 10, the disinfection light source 16 is configured to emit disinfection light 17 in a UV band for disinfecting a vicinity 180 of a physical space 2 of a target pathogen 187. The optional general illumination light source 18 is configured to emit illumination lighting 19 in the vicinity 180 of the physical space 2. The physical space 2 can include an office, hospital, medical facility, classroom, restaurant, retail store, restroom, and other private or public facilities.

Disinfection light source 16 can be an electrodeless UV lamp, such as a gas excimer lamp. An excimer lamp is a source of ultraviolet light produced by spontaneous emission of excimer molecules from an excited electronic state to the ground state. To excite emission of excimer molecules, an electric discharge that releases and transmits electricity in an applied electric field through a medium, such as a gas, can be utilized. The excimer lamp can include arc discharge light sources with a special chamber filled with noble gas, completely mercury-free, and without electrodes. One example disinfection light source 16 commercially available from Ushio America, Inc. is the Care222® UV disinfection module. The disinfection light source 16 can include filtered excimer lamps, which use a KrCL working excimer molecule, to generate 222 nm far-UVC light capable of inactivating a target pathogen 187, such as viruses and bacteria, on surface(s) 188 of various objects (e.g. desk, table, counter, chairs, etc.) and suspended in air 189. Disinfection light source 16 can emit intermittent pulses of the disinfection light 17 to reduce the target pathogen 187 on the surface 188 and suspended in air 189, and can include a short pass filter to filter out from the lamp the longer UV wavelengths that are harmful to a human 185. Other types of disinfection light sources 16 that are unfiltered are commercially available from High Energy Ozone LLC (HEO3), Sterilray™, and Eden Park Illumination, although these are examples of disinfection light sources 16 that are unfiltered. The disinfection light source 16 can be a disinfection light module that includes one or more disinfection light sources (e.g., one, two, three, four, or more excimer lamps). Commercially available lamps for illumination lighting 19 sometimes included coatings to block UV light. In one example, the disinfection light source 16 can be a commercially available xenon lamp that has the coatings that block UV light removed to allow the UV light to emanate out as the disinfection light 17.

Luminaire 10 further includes a driver circuit 11 coupled to control the disinfection light source 16 (e.g., lamp) to control light source operation of the disinfection light source 16. Driver circuit 11 can include an electrical circuit that pulses a high voltage to ignite or strike an arc of the disinfection light source 16, after which the discharge of the disinfection light source 16 can be maintained at a lower voltage. For example, the driver circuit 11 can include a ballast and an igniter, which can be wired in series with the disinfection light source 17 to control current flow through the gas medium of the disinfection light source 17. When the power is first switched on, the igniter/starter of the driver circuit 11 (which can be wired in parallel across the lamp) sets up a small current through the ballast and starter. This creates a small magnetic field within the ballast windings. A moment later, the starter interrupts the current flow from the ballast, which has a high inductance and therefore tries to maintain the current flow (the ballast opposes any change in current through it); it cannot, as there is no longer a circuit. As a result, a high voltage appears across the ballast momentarily, to which the lamp is connected; therefore the lamp receives this high voltage across it which strikes the arc within the tube/lamp. The driver circuit 11 will repeat this action until the lamp of the disinfection light source 16 is ionized enough to sustain the arc. When the lamp sustains the arc, the ballast of the driver circuit 11 performs its second function, to limit the current to that needed to operate the lamp of the disinfection light source 16. The lamp, ballast and igniter are typically rating-matched to each other; these parts are typically replaced with the same rating as the failed component to ensure proper operation.

Disinfection light source 16 and the optional general illumination light source 18 may include electrical-to-optical transducers, such as various light emitters. The emitted disinfection light 17 may be in the UV spectrum in the case of the disinfection light source 16, the visible spectrum for the illumination lighting 19 emitted from the general illumination light source 18, or in other wavelength ranges. Suitable light generation sources include various conventional lamps, such as incandescent, fluorescent or halide lamps; one or more light emitting diodes (LEDs) of various types, such as planar LEDs, micro LEDs, micro organic LEDs, LEDs on gallium nitride (GaN) substrates, micro nanowire or nanorod LEDs, nanoscale LEDs, photo pumped quantum dot (QD) LEDs, micro plasmonic LED, micro resonant-cavity (RC) LEDs, and micro photonic crystal LEDs; as well as other sources such as micro super luminescent Diodes (SLD) and micro laser diodes. A luminaire 10 that includes a laser diode as the disinfection light source 16 can include a light frequency up-converter to convert original light produced from the laser diode via second, third, or fourth harmonic light generation into disinfection light 17 (of a shorter wavelength) to deactivate a target pathogen 187. Examples of such a light frequency up-converter to emit disinfection light 17 (e.g., UV light) from converted original light (e.g., visible light) from the laser diode are disclosed in U.S. Patent Pub. No. 2020/0073199, published Mar. 5, 2020, titled "Light Frequency Upconversion of Laser Light, for Cleansing," the entirety of which is incorporated by reference herein. Of course, these light generation technologies are given by way of non-limiting examples, and other light generation technologies may be used. For example, it should be understood that non-micro versions of the foregoing light generation sources can be used.

A lamp or "light bulb" is an example of a single light source. An LED light engine may use a single output for a single source but typically combines light from multiple LED type emitters within the single light engine. Disinfection light source 16 can include a module of multiple gas excimer lamps and LEDs to emit the disinfection light 17. Optional general illumination light source 18 can include light emitting diodes (LEDs) that emit red, green, and blue (RGB) light or tunable white light to emit the illumination lighting 19. Many types of light sources provide uniform light output, although there may be some intensity striations. For purposes of the present examples, however, the light source output may not be strictly uniform across the output area or aperture of the source. For example, although the source may use individual emitters or groups of individual emitters to produce the light generated by the overall source; depending on the arrangement of the emitters and any associated mixer or diffuser, the light output may be relatively uniform across the aperture. The individual emitters or groups of emitters may be separately controllable, for example to control intensity of the source output.

Driver circuit 11 can also be coupled to the optional general illumination light source 18. Driver circuit 11 can drive the disinfection light source 16 and/or the optional general illumination light source 18 by regulating the power to disinfection light source 16 and the optional general illumination light source 18 by providing a constant quantity or power to the disinfection light source 16 and the optional general illumination light source 18 as their electrical properties change with temperature, for example. The driver circuit 11 provides power to disinfection light source 16 and the optional general illumination light source 18. As noted above, the driver circuit 11 may include a ballast and an igniter for an arc gaslamp type of disinfection light source 16. Alternatively or additionally, driver circuit 11 can include a constant-voltage driver, constant-current driver, or AC LED driver type circuit that provides dimming through a pulse width modulation (PWM) circuit and may have many channels for separate control of different LEDs or LED arrays that comprise the optional general illumination light source 18 or even a disinfection light source 16 formed of LEDs. An example of a commercially available driver circuit 11 is manufactured by EldoLED®. In the case of luminaire 10, the driver circuit 11 is coupled to the disinfection light source 16 and the optional general illumination light source 18 to control light source operation of the disinfection light source 16 and the optional general illumination light source 18. In particular, the luminaire 10 can include a luminaire optical wireless communication interface 441. Luminaire optical wireless communication interface 441 includes the general illumination light source 18, driver circuit 11, and light modulator 416 to transmit data over the VLC communication band 407. A VLC communication band 407 is a data communications network variant, which uses visible light between 400 and 800 THz (780-375 nm), and is a subset of optical wireless communications technologies. VLC can be done by having the luminaire 10 output oscillating visible light or illumination lighting 19 (e.g., projection of a barcode) in combination with the general illumination light source 18. A common method of VLC modulation or oscillation is to rapidly vary luminaire 10 brightness too quickly for a human eye to detect.

Luminaire optical wireless communication interface 441 transmits a security challenge signal 171B, containing a security challenge to a receiving mobile device 25 via the image sensor 181 of the mobile device 25. The visible light output from the general illumination light source 18 over the VLC communication band 407 is detectable by the mobile device 25 (e.g., via image sensor 181) and can be quickly decoded. The security challenge sent may be any kind of security challenge previously disclosed, including a random number generated by the luminaire 10 to serve as a distinctive temporary ID or a nonce string, with the security challenge being for the mobile device 25 to provide that distinctive temporary ID or nonce string to another device in the antimicrobial system 1. Luminaire optical wireless communication interface 441 can also optionally include an image sensor, such as a VLC camera 481 to receive data over the VLC band 407. This data may include a security challenge input signal 171C containing the security challenge input provided by the operator into the mobile device 25. The security challenge input from the security challenge input signal 171C is processed by the VLC security challenge device 1118, which is a sub-type of the security challenge device 1101 designed to process security challenge inputs provided over VLC. The VLC security challenge device 1118 validates the security challenge input, and transmits the security challenge response signal 171A.

Driver circuit 11 can further include an AC or DC current source or voltage source, a regulator, an amplifier (such as a linear amplifier or switching amplifier), a buck, boost, or buck/boost converter, or any other similar type of circuit or component. Driver circuit 11 may output a variable voltage or current to the disinfection light source 16 and the optional general illumination light source 18 that may include a DC offset, such that its average value is nonzero, and/or an AC voltage.

In order to advantageously reduce a physical size of a rectifier (AC-DC converter), e.g., included in the power supply 105 or the driver circuit 11, the luminaire 10 can include a plurality of disinfection light sources 16A-N (e.g., two, three, four, or more).

Luminaire 10 includes a luminaire control circuit 12, for example, to modulate pulses of the disinfection light 17 emitted from the disinfection light source 16 at an appropriate dose, for example, to operate within American Conference of Governmental Industrial Hygienists (ACGIH) safety guidelines of an ultraviolet radiation threshold limit 133. The luminaire control circuit 12 includes a luminaire processor 130 coupled to the driver circuit 11 and configured to control the disinfection light source 16 via the driver circuit 11. Luminaire control circuit 12 further includes a luminaire memory 131 accessible to the luminaire processor 130.

Luminaire memory 131 can optionally implement a disinfection light exposure and dosage limit control protocol via exposure and dosage control programming 132 (not shown) as described as disclosed in U.S. patent application Ser. No. 17/186,832, filed Feb. 26, 2021, titled "Luminaire with Disinfection Light Exposure and Dosage Limit Control Protocol and Sensor Integration with Height Controller," the entirety of which is incorporated by reference herein.

As shown, luminaire processor 130 is coupled to a luminaire communication interface system 155 for receiving and transmitting various control signals 170F-N and security challenge control signals 171A-D for disinfection light 17. Luminaire communication interface system 155 of FIG. 4A, mobile device network communication interface 186 of FIG. 4B, primary relay communication interface system 555 of FIG. 5, room sensor communication interface system 655 of FIG. 6, arming switch communication interface system 755 of FIG. 7, control station communication interface system 855 of FIG. 8, safeguard relay communication interface system 955 of FIG. 9, security challenge device communication interface system 1155 of FIG. 11, cloud computing device communication interface system 1355 of FIG. 13, integrated arming switch communication interface system 1755 of FIG. 17, standalone arming switch communication interface 2055 of FIG. 20, and standalone room sensor communication interface 2155 of FIG. 21 allow for data communication (e.g., wired or wireless) over various networks, including the disinfection light control network 7 of FIGS. 1-3. Communication interface systems 155, 186, 555, 655, 755, 855, 955, 1155, 1355, 1755, 2055, 2155 include at least one radio frequency (RF) transceiver (XCVR), for example, a single-band, dual-band, or tri-band chipset of RF transceiver(s) 156A-B configured for wireless communication via separate radios that operate at three different frequencies, such as sub-GHz (e.g., 900 MHz), Bluetooth Low Energy (BLE) (2.4 GHz), and 5 GHz, for example. For example, luminaire communication interface system 155 of luminaire 10A includes a first luminaire RF transceiver 156A configured for wireless communication (e.g., unicast and multicast) via a wireless disinfection light control network 7 over a first wireless disinfection light control network communication band (e.g., sub-GHz) for lighting control and systems operations (or information), such as control signals 170A-N and security challenge control signals 171A-D for disinfection light 17, with member devices of the disinfection light control group 8. Wireless radio communication interface system 155 can include a second luminaire wireless RF transceiver 156B for communication (e.g., point-to-point) via a commissioning network (not shown) with the control group 8 member (e.g., mobile device 25) over a second different wireless communications commissioning network communication band, such as 1 GHz or above communications (e.g., 2.4 GHz for Bluetooth) for commissioning, configuration, or maintenance operations. Luminaire 10 can communicate over an optional secondary network (e.g., wired or wireless LAN) via the second luminaire wireless RF transceiver 156B, such as a backhaul network for communication between the luminaires 10A-F, control group 8 members, and a network controller (e.g., gateway) 220. Transport layer methods ride on the network layer function of the RF transceivers 156A-B. The second luminaire RF transceiver 156B is optional. As further shown, luminaire communication interface system 155 can include an optional wired network communication interface 157 for communication over a wired disinfection light control network 7.

Figure 13:
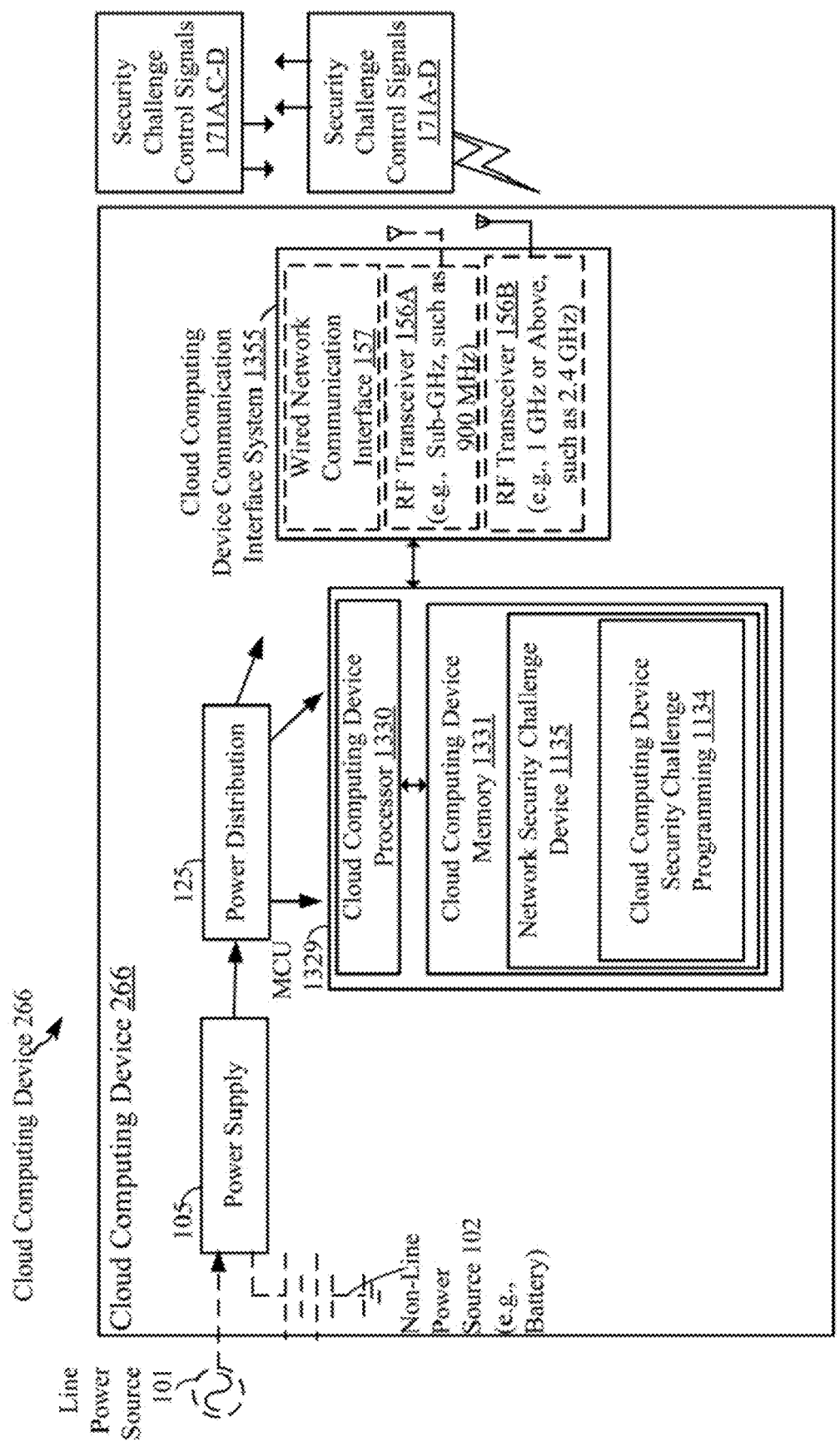
FIG. 13 is a block diagram of a cloud computing device of the antimicrobial system.
Figure 17:
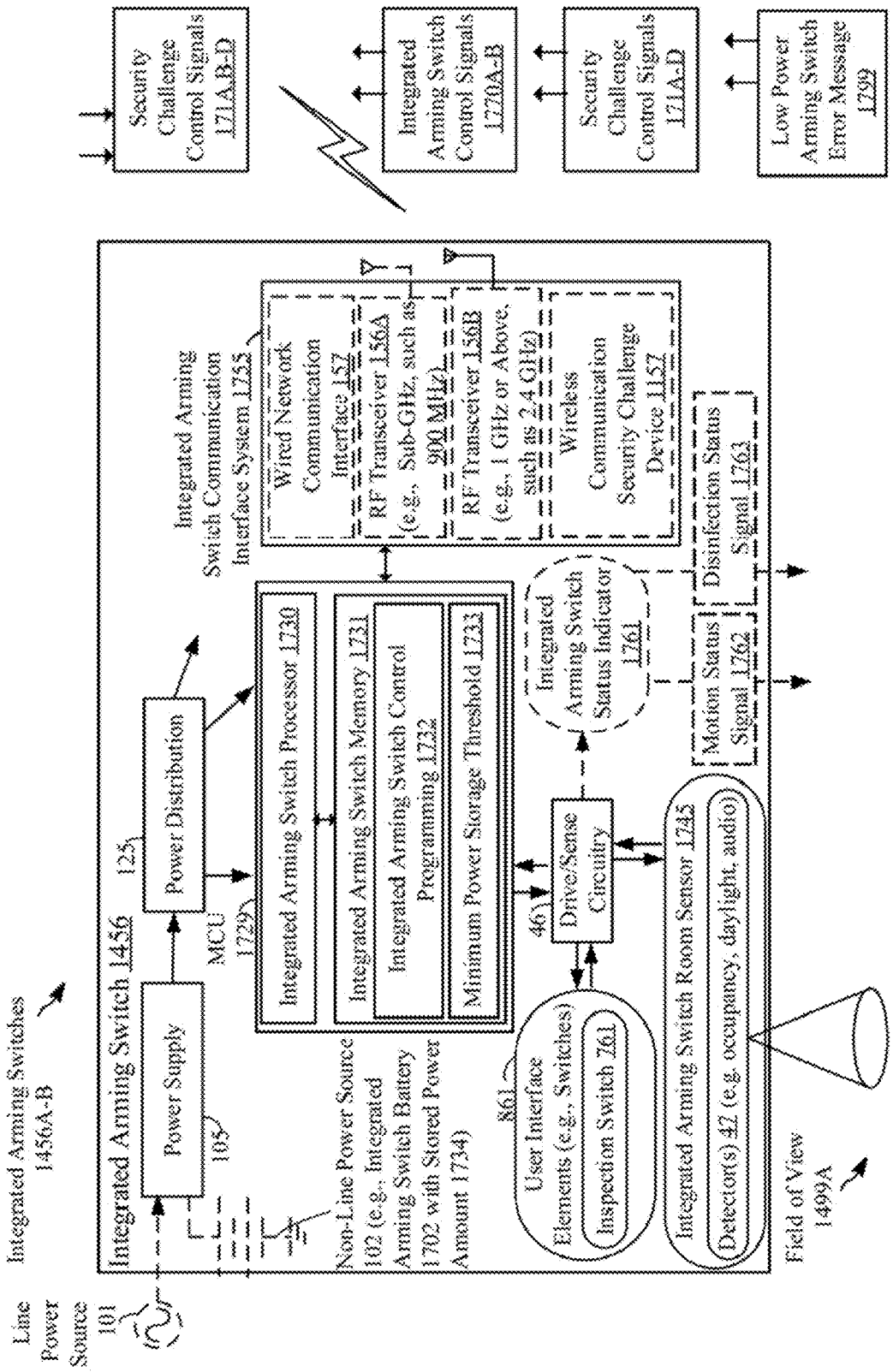
FIG. 17 is a block diagram of an integrated arming switch of the antimicrobial system.
Figure 20:
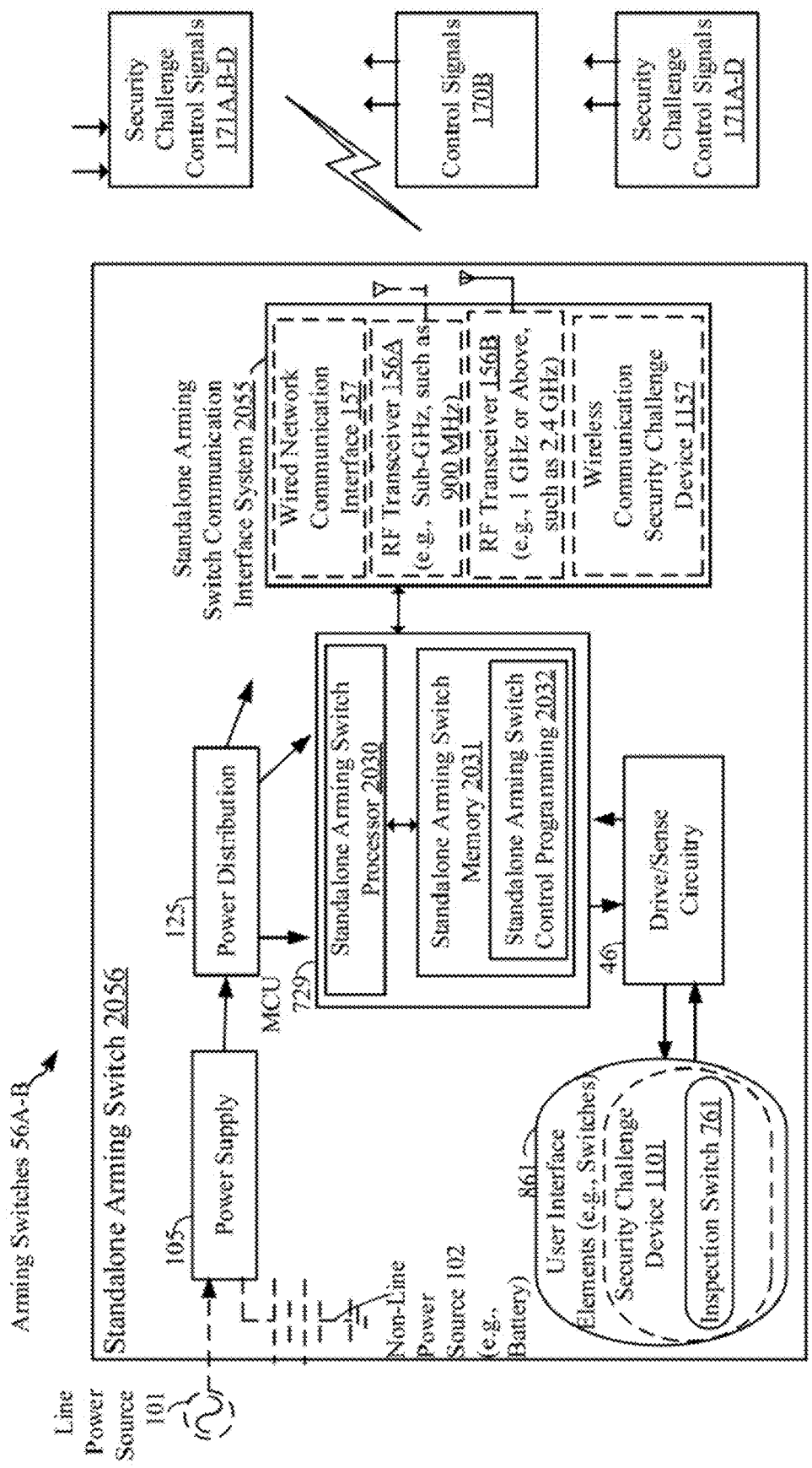
FIG. 20 is a block diagram of a standalone arming switch of the antimicrobial system.
Figure 21:
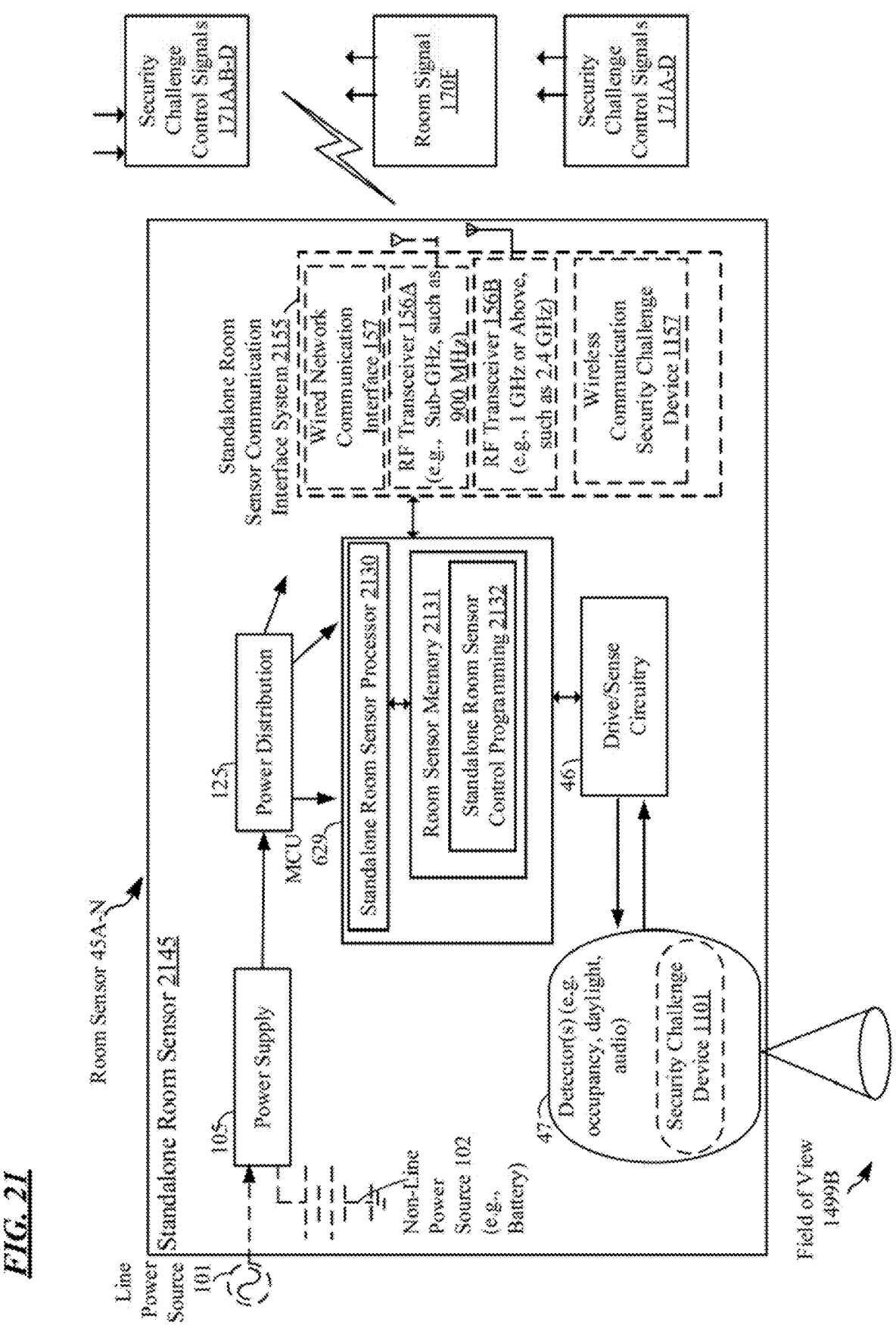
FIG. 21 is a block diagram of a standalone room sensor of the antimicrobial system.

Luminaire processor 130, mobile device processor 190 of FIG. 4B, primary relay pack processor 530 of FIG. 5, room sensor processor 630 of FIG. 6, arming switch processor 730 of FIG. 7, control station processor 830 of FIG. 8, safeguard relay pack processor 930 of FIG. 9, security challenge device processor 1130 of FIG. 11, cloud computing device processor 1330 of FIG. 13, integrated arming switch processor 1730 of FIG. 17, standalone arming switch processor 2030 of FIG. 20, and standalone room sensor processor 2130 of FIG. 21 serve to perform various operations, for example, in accordance with instructions or programming executable by processors 130, 190, 530, 630, 730, 830, 930, 1130, 1330, 1730, 2030, 2130. For example, such operations may include operations related to communications with various antimicrobial system 1 elements, such as luminaires 10A-F and control group 8 members during to implement the authenticated safe lockout protocol 1001 and the distributed disinfection control programming 532. Although a processor 130, 190, 530, 630, 730, 830, 930, 1130, 1330, 1730, 2030, 2130 may be configured by use of hardwired logic, typical processors are general processing circuits configured by execution of programming. Processors 130, 530, 630, 730, 830, 930, 1130, 1330, 1730, 2030, 2130 include elements structured and arranged to perform one or more processing functions, typically various data processing functions. Although discrete logic components could be used, the examples utilize components forming a programmable CPU. A processor 130, 190, 530, 630, 730, 830, 930, 1130, 1330, 1730, 2030, 2130 for example includes one or more integrated circuit (IC) chips incorporating the electronic elements to perform the functions of the CPU. The processors 130, 190, 530, 630, 730, 830, 930, 1130, 1330, 1730, 2030, 2130 for example, may be based on any known or available microprocessor architecture, such as a Reduced Instruction Set Computing (RISC) using an ARM architecture, as commonly used today in mobile devices and other portable electronic devices. Of course, other processor circuitry may be used to form the CPU or processor hardware in. Although the illustrated examples of the processors 130, 190, 530, 630, 730, 830, 930, 1130, 1330, 1730, 2030, 2130 include only one microprocessor, for convenience, a multi-processor architecture can also be used. A digital signal processor (DSP) or field-programmable gate array (FPGA) could be suitable replacements for the processors 130, 190, 530, 630, 730, 830, 930, 1130, 1330, 1730, 2030, 2130 but may consume more power with added complexity.

Luminaire memory 131, mobile device memory 191, primary relay pack memory 531 of FIG. 5, room sensor memory 631 of FIG. 6, arming switch memory 731 of FIG. 7, control station memory 831 of FIG. 8, safeguard relay pack memory 931 of FIG. 9, security challenge device memory 1131 of FIG. 11, cloud computing device memory 1331 of FIG. 13, integrated arming switch memory 1731 of FIG. 17, standalone arming switch memory 2031 of FIG. 20, and standalone room sensor memory 2131 of FIG. 21 are for storing data and programming. In the example, the main memory system 131, 191, 531, 631, 731, 831, 931, 1131, 1331, 1731, 2031, 2131 may include a flash memory (non-volatile or persistent storage) and/or a random access memory (RAM) (volatile storage). The RAM serves as short term storage for instructions and data being handled by the processors 130, 190, 530, 630, 730, 830, 930, 1130, 1330, 1730, 2030, 2130 e.g., as a working data processing memory. The flash memory typically provides longer term storage.

Of course, other storage devices or configurations may be added to or substituted for those in the example. Such other storage devices may be implemented using any type of storage medium having computer or processor readable instructions or programming stored therein and may include, for example, any or all of the tangible memory of the computers, processors or the like, or associated modules.

FIG. 4B is an isometric view of a luminaire 10A mounted in the physical space 2 and in communication with the mobile device 25. In the example of FIG. 4B, the drop light fixture type luminaire 10A was hung below the ceiling by multiple support rods or cables attached to a number of brackets on the luminaire 10A. The example of FIG. 4B represents a pendant type light fixture implementation of the luminaire 10A in which the fixture has a bracket on a surface opposite the artificial illumination lighting output, providing an attachment point for a single strut attached to or through the ceiling. Other aspects of structure, orientation and operation of the other luminaires 10B-F is generally similar to the luminaire 10A discussed herein. Location of electronics should be decided (e.g. in ceiling or on fixture) size and weight considerations, since fixture weight may be an issue. For example, the electronics of the lighting device may be in the suspended luminaire portion or included in or near the support structure in our above the ceiling to reduce the weight held below the ceiling by the support(s) and bracket (s).

Luminaire 10A controls the general illumination light source 18, via the light modulator 416, to transmit over the VLC band 407, the respective security challenge signal 171B to the mobile device 25.

Mobile device 25 includes the image sensor 181 to receive VLC over the VLC band 407. In a first example, the VLC sent by the luminaire 10A is a security challenge signal 171B containing a security challenge. The mobile device 25, utilizing the mobile security challenge device 1125, converts the security challenge signal 171B into the security challenge. Again, this security challenge may be any previously disclosed security challenge, and in this example is a password request. The security challenge may utilize any user interface component of the mobile device 25. The operator uses the mobile device 25 to make a password entry as the security challenge input, and the mobile device 25 validates this security challenge input to create the security challenge response signal 171A.

The luminaire 10A is capable of broadcasting data, including the security challenge within the security challenge signal 171B, to an environment such as the physical space 2 by modulating a respective visible light output in a manner not visible to the human eye. The visible light output is detectable by mobile device 25 (e.g., via image sensor 181) and can be quickly decoded. A common method of VLC modulation is to rapidly vary luminaire brightness too quickly for a human eye to detect.

In this example, the mobile device 25 transmits the security challenge response signal 171A back to the luminaire 10A via the image sensor 481 of the luminaire 10A. Alternatively, the mobile device 25 may use the mobile device network communication interface 186 to transmit the security challenge response signal 170A to any luminaire 10A-F, control group member 8, or the remote cloud computing device 266.

However, in some examples the mobile device 25 may not perform security challenge input validation—instead, the mobile device 25 collects the security challenge input, then forwards the security challenge input to another device for validation. This is exemplified by the network security challenge device 1135 within the primary relay pack 111. In such an example, the mobile device 25 collects the security challenge input, and transmits the security challenge input signal 171C to a device on the disinfection light control network 7. The mobile device 25 may directly transmit the security challenge input signal 171C to a validating network security challenge device 1135, or the security challenge input signal 171C may be forwarded by another device on the disinfection light control network 7. This is needed in particular in examples where the mobile device 25 transmits the security challenge input signal 171C via the VLC band 407, but the intended network security challenge device 1135 does not have direct access to an image sensor 481. The security challenge input signal 171C would be received by, for example, the image sensor 481 of a luminaire 10A, which then transmits the security challenge input signal 171C to the network security challenge device 1135 of the primary relay pack 111. This network security challenge device 1135 would then validate the security challenge input from the security challenge input signal 171C, and if necessary send the security challenge response signal 171A over the disinfection light control network 7 to inform other control group 8 devices of the validity of the security challenge input made by the operator.

FIG. 5 is a block diagram of the switching device 110 including a single primary relay pack 111 of the antimicrobial system 1. The primary relay pack 111 is a networked electrical relay used to control the flow of electricity to the luminaires 10G-L. Primary relay pack 111 includes a primary relay pack control circuit 512, primary relay pack regulator 511, and an optional primary relay pack communication interface system 555. The primary relay pack regulator 511 is able to increase and decrease the current and voltage outflow to the luminaires 10G-L, and can detect changes in voltage and current both on the electrical inflow and outflow to and from the primary relay pack regulator 511. As shown, primary relay pack control circuit 512 includes primary relay pack processor 530 and arming switch memory 731 to implement the authenticated safe lockout protocol 1001 and the distributed disinfection control programming 532 described herein.

The circuitry, hardware, and software of the arming switch 56 is similar to the luminaire 10 of FIG. 4A, including the line power source 101, non-line power source 102, power supply 105, power distribution 125, and the primary relay pack communication interface system 555. The primary relay pack 111 can include a primary relay pack communication interface system 555 like the luminaire communication interface system 155 of FIG. 4A.

As described herein, an antimicrobial system 1 includes a luminaire 10A configured to emit a disinfection light 17 in an ultraviolet (UV) band for disinfecting a vicinity 180 of a physical space 2 of a target pathogen 187 that is exposed to the disinfection light 17. The UV band of the luminaire 10A can be 200 nanometers (nm) to 280 nm wavelength. The antimicrobial system 1 further includes a switching device 110 that includes a primary relay pack 111. The primary relay pack 111 includes a primary relay pack regulator 511 coupled to the luminaire 10A and configured to control power to the luminaire 10A. The primary relay pack 111 further includes a primary relay pack processor 530 coupled to the primary relay pack regulator 511 and configured to control the primary relay pack regulator 511. The primary relay pack 111 further includes a primary relay pack memory 531 accessible to the primary relay pack processor 530. The primary relay pack 111 further includes distributed disinfection control programming 532 in the primary relay pack memory 531.

Antimicrobial system 1 further includes a control station 20 of FIG. 8 located outside the physical space 2 and coupled to the switching device 110. The control station 20 includes: (a) a disinfection initiation user interface element 862 to produce an arming initiation signal 170A based on a first input from an operator, (b) an arming completion interface user element 863 to produce an arming completion signal 170C based on a third input from the operator, and (c) a disinfection commencement user interface element 864 to produce a disinfection commencement signal 170D based on a fourth input from the operator.

The antimicrobial system 1 further includes an arming switch 56A located inside the physical space 2, coupled to the switching device 110. The arming switch 56A is configured to produce a visual inspection signal 170B based on a second input from the operator. The antimicrobial system 1 further includes a room sensor 45A located inside the physical space 2 and coupled to the switching device 110. The room sensor 45A is configured to produce a room state signal 170F in response to detecting occupancy of the vicinity 180 of the physical space 2 by a human 185.

In this example, the primary relay pack 111 does not have any direct user interface elements, like those found in the control station 20. Therefore, this example primary relay pack 111 has no means of interacting directly with an operator, and either receives a security challenge response signal 171A indicating that the operator security challenge input was validated, or will receive the operator security challenge input directly from a security challenge input signal 171C, upon which the primary relay pack 111 will perform validation of the operator security challenge input directly by utilizing the network security challenge device 1135.

Execution of the distributed disinfection control programming 532 by the primary relay pack processor 530 configures the primary relay pack 111 to perform the following functions. First, in response to the control station 20 producing the arming initiation signal 170A that is ON based on the first input, track the visual inspection signal 170B based on the second input produced by the arming switch 56A. Second, determine that the tracked visual inspection signal 170B is ON based on the second input produced by the arming switch 56A. Third, in response to determining that the tracked visual inspection signal 170B is ON and the control station 20 producing the arming completion signal 170C that is ON based on the third input, receive the disinfection commencement signal 170D that is ON based on the fourth input from the control station 20. Fourth, in response to receiving the disinfection commencement signal 170D that is ON based on the fourth input from the control station 20, control power to the luminaire 10A to emit the disinfection light 17 via the primary relay pack regulator 511.

In an example, the first input from the operator is a first button press, the second input from the operator is a second button press, the third input from the operator is a third button press, and the fourth input from the operator is a turn of a key. The arming initiation signal 170A, the visual inspection signal 170B, the arming completion signal 170C, and the disinfection commencement signal 170D are disinfection control signals produced in a disinfection control signal sequence, for example, successively in order. Each of the disinfection controls signals 170A-D are switched between an on signal or an off signal by the operator to control power to the disinfection light source 16 to emit the disinfection light 17 via the primary relay pack regulator 511. In response to each of the disinfection controls signal 170A-D being switched to the on signal by the operator within a limited time (e.g., 5 minutes), the primary relay pack regulator 511 powers on the disinfection light source 16 to emit the disinfection light 17. In response to one or more of the disinfection controls signals 170A-D being switched to the off signal, the primary relay pack regulator 511 powers off the disinfection light source 16 to stop emitting the disinfection light 17.

Additionally, the function to determine that the tracked visual inspection signal 170B is ON enables or unlocks the disinfection commencement user interface element 864, via an enablement signal 170E. The function to control the luminaire 10A to emit the disinfection light 17 further includes to control the luminaire 10A to stop emitting the disinfection light 17 in response to one or more of: (i) the visual inspection signal 170B produced by the arming switch 56A indicates to turn off the disinfection light 17, or (ii) the room state signal 170F produced by the room sensor 45A indicates to turn off the disinfection light 17. Moreover, the function to control the luminaire 10A to emit the disinfection light 17 further includes to control the luminaire 10A to stop emitting the disinfection light in response to the expiration of a primary emission timer 921 of the primary relay pack 111, or the expiration of a safeguard emission timer 922 of the safeguard relay pack 112.

Switching device 110 can further include a safeguard relay pack 112, coupled to the primary relay pack 111. The safeguard relay pack 112 is configured to detect a failure of the primary relay pack 111. Safeguard relay pack 112 further includes a first terminal 913 coupled to the primary relay pack regulator 511. The safeguard relay pack 112 detects, via the first terminal 913, a failure of the primary relay pack 111 when the luminaire 10A emits the disinfection light 17 and one or more of: (i) the visual inspection signal 170B produced by the arming switch 56A indicates to turn off the disinfection light 17, (ii) the room state signal 170F produced by the room sensor 45A indicates to turn off the disinfection light 17, (iii) the expiration of a safeguard emission timer 922 of the safeguard replay pack 112, or (iv) the primary relay pack 111 is unsuccessfully attempting to control the luminaire 10A to stop emitting the disinfection light 17. In response to the safeguard relay pack 112 still sensing sufficient power at the first terminal 913 for the luminaire 10A to emit the disinfection light 17, the safeguard relay pack 112 generates an error message 599A indicating the failure of the primary relay pack 111, and the safeguard relay pack regulator 911 powers of the disinfection light source 16 to stop emitting the disinfection light 17.

In examples with multiple luminaires 10A-F, the idle current load of the multiple luminaires 10A-F may be equal or greater than the active load of a single luminaire 10A. In such a circumstance, "sufficient power" is to be understood as more power than expected by the safeguard relay pack 112, given that the primary relay pack 111 is attempting to control the luminaires 10A-F to stop emitting the disinfection light 17.

Safeguard relay pack 112 further includes a second terminal 914 coupled to the luminaire 10A. The safeguard relay pack 112 detects a second failure of the luminaire 10A when: (i) the safeguard relay pack 112 senses sufficient power at the first terminal 913 that is enough to power the luminaire 10A to emit the disinfection light 17, and (ii) the safeguard relay pack 112 senses insufficient power at the second terminal 914 for the luminaire 10A to emit the disinfection light 17. In response to the safeguard relay pack 112 sensing insufficient power at the second terminal 914 for the luminaire 10A to emit the disinfection light 17, the safeguard relay pack 112 generates a second error message 599B indicating the second failure of the luminaire 10A. The safeguard relay pack 112 can be co-located within the luminaire 10A.

Referring to FIG. 3, the antimicrobial system 1 can further include a plurality of luminaries 10G-L. A respective luminaire 10G-L is located in a respective vicinity 180G-L of the physical space 2. The antimicrobial system 1 further includes a plurality of room sensors (e.g., occupancy sensors) 45G-L. A respective occupancy sensor 45G-L is located in the respective vicinity 180G-L. The respective occupancy sensor 45G-L is coupled to the respective luminaire 10G-L. The respective occupancy sensor 45G-L is coupled to the switching device 110 to produce a respective occupancy signal 170G-L in response to sensed occupancy. Execution of the distributed disinfection control programming 532 by the primary relay pack processor 531 further configures the primary relay pack 111 to perform the following functions. First, in response to determining that the tracked visual inspection signal 170B is ON, determine that the respective occupancy signal 170G-L indicates the respective vicinity 180G-L is unoccupied by the human 185. Second, in response to determining that the respective occupancy signal 170G-L indicates the respective vicinity 180G-L is unoccupied and receiving the disinfection commencement signal 170D from the control station 20, control power to the respective luminaire 10G-L to emit the disinfection light 17 via the primary relay pack regulator 511. Third, control the respective luminaire 10G-L to stop emitting the disinfection light 17 in response to one or more of:

(i) the visual inspection signal 170B produced by the arming switch 56A indicates to turn off the disinfection light 17, (ii) the room state signal 170F produced by the room sensor 45M (shown as entry sensor in FIG. 3) indicates to turn off the disinfection light 17, or (iii) the respective occupancy signal 170G-L produced by the respective occupancy sensor 45G-L indicates to turn off the disinfection light 17. The respective occupancy sensor 45G-L can be co-located within the respective luminaire 10G-L.

Again referring to FIG. 3, the antimicrobial system 1 can further include a plurality of luminaires 10G-L. Execution of the distributed disinfection control programming 532 by the primary relay pack processor 511 further configures the primary relay pack 111 to perform the following functions. First, control each of the luminaires 10G-L to stop emitting the disinfection light 17 in response to one or more of: (i) the visual inspection signal 170B produced by the arming switch 56A indicates to turn off the disinfection light 17, or (ii) the room state signal 170F produced by the room sensor 45M (shown as entry sensor in FIG. 3) indicates to turn off the disinfection light 17.

In another example, execution of the distributed control programming 532 by the primary relay pack processor 511 further configures the primary relay pack 111 to perform the following function. In response to the control station 20 producing the arming initiation signal 170A, confirm the arming switch 56A is able to produce the visual inspection signal 170B; and confirm the room sensor 45A is able to produce the room state signal 170F.

FIG. 6 is a block diagram of a room sensor 45 of the antimicrobial system 1. The room sensor 45 can be an occupancy, audio, light, motion, ozone, or daylight sensor. The room sensor 45 can be a standalone device in the antimicrobial system 1 as shown in FIGS. 2A-B or included (e.g., integrated) in the luminaire 10 as shown in FIGS. 3-4. Room sensor 45 includes a micro-control unit (MCU) 629, drive/sense circuitry 46, detector(s) 47 (e.g., occupancy, light, or audio), and an optional sensor communication interface system 655. Detectors 47 can be a sensor of occupancy (e.g., infrared sensor or image sensor, such as a camera, for occupancy or motion detection), a light sensor, an audio sensor, a temperature sensor, or other environmental sensor. Drive/sense circuitry 46, such as application firmware, drives the occupancy, audio, and photo sensor hardware. The detectors 47 can additionally be configured to act as or to include a security challenge device 1101, in particular as part of a retinal scanner 1206 as discussed in FIGS. 11 and 12, as well as a camera utilizing facial recognition to perform a facial scan of the operator. The room sensor 45 may incorporate any type of security challenge device 1101 or variant disclosed herein.

As shown, MCU 629 includes room sensor processor 630 and room sensor memory 631 to implement the authenticated safe lockout protocol 1001 of the distributed disinfection control programming 532 described herein. The circuitry, hardware, and software of the room sensor 45 is similar to the luminaire 10 of FIG. 4A, including the line power source 101, non-line power source 102, power supply 105, power distribution 125, and the room sensor communication interface system 655. If the room sensor 45 is a standalone device, then the room sensor 45 can include a room sensor communication interface system 655 like the luminaire communication interface system 155 of FIG. 4A. If the room sensor 45 is integrated into the luminaire 10 like that shown in FIG. 4A, then the room sensor 45 does not include the room sensor communication interface system 655. However, the circuitry of the room sensor 45 can be extremely simple, potentially providing a binary switch value (on/off) via current or voltage interruption to the switching device 110 based upon whether the detector 47 of the room sensor 45 is stimulated.

FIG. 7 is a block diagram of an arming switch 56 of the antimicrobial system 1. The arming switch 56 can be a toggle switch, button, keypad 1211, or other interactable component. Arming switch 56 includes a micro-control unit (MCU) 729, drive/sense circuitry 46, switches 861, and an optional arming switch communication interface system 755. The switches 861 of the arming switch at least include an inspection switch 761, which sends the visual inspection signal 170B to the disinfection light control network 7 and in particular the switching device 110. The example arming switch 56 are simple on/off switches, but the inspection switch 761 could by any kind of user interface element; the arming switches 56A-B could require a key, or a security challenge such as a passphrase, PIN, or fingerprint scan. Additionally, an arming switch 56A can implement a different security challenge, or could implement no security challenge or key requirement at all, even if another arming switch 56B implements a security challenge or key requirement. The inspection switch 761 could also be implemented virtually, as a digital object an operator interacts with via a computing component like the touch screen device 811 of FIG. 8.

As shown, MCU 729 includes arming switch processor 730 and arming switch memory 731 to implement the authenticated safe lockout protocol 1001 and the distributed disinfection control programming 532 described herein. The circuitry, hardware, and software of the arming switch 56 is similar to the luminaire 10 of FIG. 4A, including the line power source 101, non-line power source 102, power supply 105, power distribution 125, and the arming switch communication interface system 755. The arming switch 56 can include an arming switch communication interface system 755 like the luminaire communication interface system 155 of FIG. 4A. However, the circuitry of the arming switch 56 can be extremely simple, potentially providing a binary switch value (on/off) via current or voltage interruption to the switching device 110 based upon whether inspection switch 761 (e.g. a toggle switch, button, etc.) of the room sensor 45 is activated.

The arming switch communication interface system 755 can also include a wireless communication security challenge device 1157. The wireless communication security challenge device 1157 utilizes the one or more of the RF transceivers 156A-B for short wireless communication over a short range wireless communication network 399 to transmit a security challenge via a security challenge signal 171B to a mobile device 25. The operator then enters the security challenge input, and the mobile device 25 sends the security challenge input signal 171C to the wireless communication security challenge device 1157. The wireless communication security challenge device 1157 then validates the security challenge input from the security challenge input signal 171C, and transmits the security challenge response signal 171A to the disinfection light control network 7.

Alternatively, the arming switch communication interface system 755 may not include a wireless communication security challenge device 1157—instead, the arming switch communication interface system 755 transmits the security challenge signal 171B to the mobile device 25. Then, the mobile security challenge device 1125 determines if the security challenge input of the operator is a valid security challenge input for the security challenge, and transmits the security challenge response signal 171A into the disinfection light control network 7, possibly via the arming switch communication interface system. In another alternative, the arming switch communication interface system 755 transmits the security challenge signal 171B to the mobile device 25. Then, the operator inputs the security challenge input into the mobile device 25 based upon the security challenge from the security challenge signal, and the mobile device transmits the security challenge input signal 171C to another security challenge device 1101 in the disinfection light control network, possibly a network security challenge device 1135 of the arming switch 56, for validation.

FIG. 8 is a block diagram of a control station 20 device of the antimicrobial system 1. The circuitry, hardware, and software of the control station 20 shown are similar to the luminaire 10 of FIG. 4A, including the control station communication interface system 855. As shown, the control station 20 includes an MCU 829 that includes a control station memory 830 and control station processor 831 to implement the authenticated safe lockout protocol 1001 and the distributed disinfection control programming 532 described herein. The drive/sense circuitry 46 of the control station 20 responds to user interface elements (e.g., switches 861). Switches 861 can be an on/off switch, dimmer switch, etc. to control the disinfection light source 17 of the luminaire 10 based on Acuity Brands Lighting's commercially available xPoint® Wireless ES7 product. In this example, control station 20 includes three switches: the disinfection initiation user interface element 862 that sends the arming initiation signal 170A, the arming completion interface user element 863 (e.g., a button) that sends the arming completion signal 170C, and the commencement user interface element 864 (e.g., a keyswitch) that sends the disinfection commencement signal 170D. The control station 20 may further include a pilot light status indicator (not shown) to visually display the state of the various switches 761, 862-864 in response to the first, second, third, and fourth inputs of the operator during the authenticated safe lockout protocol 1001.

In some examples, control station 20 includes a single shared button switch 861 for the disinfection initiation user interface element 862, arming completion interface user element 863, and disinfection commencement user interface element 864. When the switches 861 are implemented as a button station, the button station can include various button settings that can have the settings for the disinfection light 17 emitted from the luminaire 10 adjusted, for example, four buttons can be arranged with two longitudinal buttons (north-south) and two lateral buttons (east-west).

Alternatively, instead of physical buttons or switches 861, the control station 20 may implement a touch screen display 811. The touch screen display 811 enables setting adjustments for the disinfection light source 17 emitted from the luminaire 10 to be inputted via a user interface application (not shown) through manipulation or gestures on a touch screen display 811. The touch screen display 811 may also implement one or all of the disinfection initiation user interface element 862, arming completion interface user element 863, or disinfection commencement user interface element 864. For output purposes, the touch screen display 811 includes a display screen, such as a liquid crystal display (LCD) or light emitting diode (LED) screen or the like. For input purposes, the touch screen display 811 includes a plurality of touch sensors.

A keypad 1211 may be implemented in hardware as a physical keyboard of control station 20, and keys may correspond to hardware keys of such a keyboard. Alternatively, some or all of the keys (and keyboard) of control station 20 may be implemented as "soft keys" of a virtual keyboard graphically represented in an appropriate arrangement via touch screen display 811. The soft keys presented on the touch screen display 811 may allow the user of control station 20 to invoke the same user interface functions as with the physical hardware keys.

Drive/sense circuitry 46 is coupled to touch sensors of touch screen display 811 for detecting the occurrence and relative location/position of each touch with respect to a content display area of touch screen display 811. In this example, drive/sense circuitry 46 is configured to provide control station processor 830 with touch-position information based on user input received via touch sensors. In some implementations, control station processor 830 is configured to correlate the touch position information to specific content being displayed within the content display area on touch screen display 811. The touch-position information captured by the drive/sense circuitry 46 and provided to control station processor 830 may include, but is not limited to, coordinates identifying the location of each detected touch with respect to the display area of touch screen display 811 and a timestamp corresponding to each detected touch position.

In general, touch screen display 811 and its touch sensors (and one or more keys, if included) are used to provide a textual and graphical user interface for the control station 20. Touch screen display 811 also enables the user to interact directly with the viewable content provided in the content display area, typically by touching the surface of the screen with a finger or an implement such as a stylus. The control station 20 may display a disinfection status indicator on the touch screen display 811 to display a disinfection state of the vicinity 180 of the luminaires 10A-F or via the pilot light status indicator.

An operator of an antimicrobial system 1 may only be aware of features and functionality that other similar products possess and the operator has experience with. For example, an antimicrobial system 1 provides functionality to turn the luminaires 10A-F on in a physical space 2, turn the luminaires 10A-F off, and possibly raise and lower the lighting level of the luminaires 10A-F. These operations can be performed by a user interface element, such as a labeled mechanical button, keypad 1211, touch screen display 811, or a graphical user interface element, among others.

The antimicrobial system 1 that implements the authenticated safe lockout protocol 1001 includes various interface elements. The user interface elements include inspection switch 761 of the arming switches 56A-B. The user interface elements further include disinfection initiation user interface element 862, arming completion user interface element 863, and disinfection commencement user interface element 864 of the control station 20. User interface elements 761, 861-864 can be mechanical or software components, such as buttons, a keypad 1211, the touch screen display 811, etc.

FIG. 9 is a block diagram of a switching device 110 including both a primary relay pack 111 and a safeguard relay pack 112 of the antimicrobial system 1. The circuitry, hardware, and software of the safeguard relay pack 112 is similar to the primary relay pack 111 of FIG. 5. However, the safeguard relay pack 112 may have less programming, or reduced components or processing capability as compared to the primary relay pack 111. Alternatively, the safeguard relay pack 112 may be identical to the primary relay pack 111, and the two relay packs 111, 112 may need to determine which of the two relay packs 111, 112 is the primary relay pack 111 and which relay pack is the safeguard relay pack 112. Furthermore, the switching device 110 may by a single physical device, which includes the primary relay pack 111 and the safeguard relay pack 112. A singular switching device 110 would be advantageous in that the primary relay pack 111 and safeguard relay pack 112 are ordered near manufacturing time, can be configured to know which relay pack is the primary relay pack 111, which relay pack is the safeguard relay pack 112, and therefore may not require programming to determine the ordering of the relay packs. In the antimicrobial system 1, the relay pack 112 closer on the power line to the luminaires 10A-F is the safeguard relay pack 112, and the relay pack 111 closer on the power line to the line power source 101 is the primary relay pack 111. There are several methods for the two relay packs 111, 112 to determine their roles and ordering, including communicating between the primary relay pack communication interface system 555 and the safeguard relay pack communication interface system 955, or by using the primary relay pack regulator 511 and the safeguard relay pack regulator 911 to detect voltage and current changes, or a combination of both methods.

FIG. 10A is a flowchart diagramming the authenticated safe lockout protocol 1001 of the antimicrobial system 1. This authenticated safe lockout protocol 1001 can be designed to comply with safety regulations for UV light disinfection of a physical space 2 where human(s) 185 travel through or occupy, and prevents non-authorized personnel from activating the disinfection light source of a luminaire 10 known to be hazardous to humans 185 and animals. The authenticated safe lockout protocol can be implemented in the control station 20, arming switches 56A-B, or a hybrid system with identifications methods implemented across different types of control group devices 8. Any authentication method listed herein, or combination of multiple authentication methods, can be implemented in any of the antimicrobial system 1 devices. For authentication methods requiring an operator physically interface with the security challenge device operator interface 1161, the surface of the security challenge device operator interface 1161 can incorporate antimicrobial coatings, finishings, and materials.

Beginning in step 1005, the authenticated safe lockout protocol 1001 includes in response to a control station 20 producing an arming initiation signal 170A that is ON based on a first input from an operator, tracking a visual inspection signal 170B produced by an arming switch 56A. The first input from the operator is a first button press. An operator uses the control station 20 to indicate their intention to disinfect the physical space 2, and to do so the operator interacts with the disinfection initiation user interface element 862 to produce an arming initiation signal 170A based on a first input. The tracking of a visual inspection signal 170B occurs at the primary relay pack 111, and is a tracking process, determining whether the inspection switch 761 at each arming station 56A-B has been pressed. The primary relay pack 111 will attempt to track one visual inspection signal 170B for each arming switch 56A-B in the antimicrobial system 1. The logic to determine whether the luminaires 10A-F should be powered (e.g., energized) will be implemented in the "lead" primary relay pack 111 of switching device 110 of the pair of relay packs 111, 112 within the switching device 110. The primary relay pack 111 will act as a poller.

The primary relay pack 111: (a) confirms the arming switch 56A is able to produce the visual inspection signal 170B; and (b) the room sensor 45A (e.g., occupancy sensor) is able to produce the room state signal 170F. The primary relay pack 111 is able to confirm the capability of the other devices in the control group 8 because during commissioning, the number of room sensors 45A-F and arming switches 56A-B which are installed in the physical space 2 were found using standard network discovery. When the arming initiation signal 170A is produced, the primary relay pack 111 will check to make sure that all arming switches 56A-B and room sensors 45A-F are online through network polling. If any of the control group 8 members are offline, the arming sequence will be aborted and an error code 599A-D will blink on the control station 20, or will be transmitted to the cloud computing device 266, or both. This confirmation of the producibility of signals by control group 8 members may occur multiple times, or continuously, at any point during the authenticated safe lockout protocol 1001 and during the operation of the disinfection light 17.

Moving to step 1010, the authenticated safe lockout protocol 1001 further includes determining that the tracked visual inspection signal 170B is ON based on a second input produced by the arming switch 56A. The operator inspects the physical space 2, and presses all of the arming switches 56A-B, such as arming switch 56A to produce the visual inspection signal 170B. The second input from the operator is a second button press.

Continuing to step 1015, the authenticated safe lockout protocol 1001 further includes in response to determining that the tracked visual inspection signal 170B is ON and the control station 20 subsequently producing the arming completion signal 170C that is ON based on a third input from the operator, receiving a disinfection commencement signal 170D that is ON based on a fourth input from the control station 20. For example, the operator presses the arming completion interface user element 863 at the control station 20, to produce the arming completion signal 170C. The third input from the operator is a third button press. After the control station 20 produces the arming completion signal 170C, the primary relay pack 111 determines the arming switch 56A produced the visual inspection signal 170B and that the visual inspection signal 170B is ON. The ON signal could be a formatted message, or the presence or absence of power in a communication line during a particular period of time.

After the arming completion signal 170C is produced but before the operator can trigger the arming commencement signal 170D, the authenticated safe lockout process 1001 implements the following steps. Checking that no room state signal 170F is indicated as OFF by at least one room sensor 45G-N, meaning that, during the check, no human 185 is detected by the antimicrobial system 1 within the physical space 2. The OFF signal could be a formatted message, or the presence or absence of power in a communication line during a particular period of time. If even one room state signal 170F has been indicated as OFF by at least one room sensor 45G-N, then it is possible that a human 185 is within the physical space 2, and a safe lockout cannot occur.

After checking that no room state signal 170F of any room sensor 45G-N is set to OFF and determining that the visual inspection signal 170B is ON, the primary relay pack 111 enables the disinfection commencement user interface element 864. An operator triggering the disinfection commencement user interface element 864 while the disinfection commencement user interface element 864 is not enabled will have no effect on the antimicrobial system 1, or will cancel the safe lockout protocol 1001.

The operator, after the disinfection commencement user interface element 864 is enabled, will perform a fourth user input into the disinfection commencement user interface element 864, in this example by inserting and turning a key. Entering this fourth input into the disinfection commencement user interface element 864 causes the control station 20 to produce the disinfection commencement signal 170D.

While steps 1005-1015 proceed, a parallel line of steps is occurring. In step 1025, the authenticated safe lockout protocol 1001 includes receiving a security challenge input from the operator via the security challenge device operator interface 1161. The security challenge input may take a variety of forms, from a correct sequence of button presses in order to enter a password, to the presentation of a proper retina in order to perform a retina scan. Any relevant action that the operator performs on the security challenge device operator interface 1161, or relevant data that the operator presents to the security challenge device operator interface 1161, qualifies as security challenge input.

Moving to step 1030, the authenticated safe lockout protocol 1001 includes, in response to receiving the security challenge input, generating a security challenge response signal 171A. This step includes the validation of the input: determining whether the password entered is a valid password, or whether the presented retina is the retina of an authorized operator. The security challenge response signal 171A will indicate either to turn on the disinfection light 17, or to turn off the disinfection light 17. Generally, valid security challenge inputs indicate to turn on the disinfection light 17, but they also may indicate an emergency shut off, in certain contexts for example. Similarly, invalid security challenge inputs indicate to turn off the disinfection light 17, but they also may be ignored as noise in certain contexts.

Continuing to step 1035, the authenticated safe lockout protocol 1001 includes sending, via a security challenge communication interface 1155, the security challenge response signal 171A. This security challenge response signal 171A will either indicate to turn on the disinfection light 17, to turn off the disinfection light 17, or to not alter the state of the disinfection light 17.

Finishing in step 1040, the authenticated safe lockout protocol 1001 further includes in response to receiving the disinfection commencement signal 170D that is ON based on the fourth input from the control station 20, and receiving the security challenge response signal 171A, controlling power to a luminaire 10A to emit a disinfection light 17 via a primary relay pack regulator 511. As noted above, the fourth input from the operator can be a turn of a key. The steps 1005-1015 and 1040 are performed sequentially, and therefore the arming initiation signal 170A, the visual inspection signal 170B, the arming completion signal 170C, and the disinfection commencement signal 170D are disinfection control signals 170A-D are produced in a disinfection control signal sequence. The steps 1025-1035 are also performed sequentially. Step 1025 in particular can be interleaved into steps 1005-1015, as the security challenge input may double as the first input, the second input, or the third input or fourth input. The authenticated safe lockout protocol 1001 interweaving strategy 1090 is shown in more detail in FIG. 10B. Each of the disinfection control signals are switched between an on signal or an off signal by the operator to control power to the disinfection light source 16 to emit the disinfection light 17 via the primary relay pack regulator 511. Hence, the authenticated safe lockout protocol 1001 further includes in response to each of the disinfection controls signals 170A-D and security challenge response signal 171A being switched to the on signal by the operator within a limited time (e.g., 5 minutes), powering on, via the primary relay pack regulator 511, the disinfection light source 16 to emit the disinfection light 17.

As an alternative, the authenticated safe lockout protocol 1001 may use a security challenge device 1101 at the arming switches 56A-B, rather than at the control station 20. This alternative is useful because it confirms that the person operating the arming switches 56A-B is the authorized operator, and not an unauthorized user. In this alternative, the first input from the operator is a first button press, the second input from the operator is also the security challenge input, the third input from the operator is a second button press, and the fourth input from the operator is a third button press.

An additional alternative, disclosed in FIG. 8, involves the control station 20 utilizing a touch screen display 811 acting as a security challenge device 1101. In this alternative, the first input from the operator is a first interaction with the touch screen display, the second input from the operator is also the security challenge input, the third input from the operator is a second interaction with the touch screen display, and the fourth input from the operator is a third interaction with the touch screen display.

In a further example, while at least one luminaire 10G-L emits the disinfection light 17, the physical space 2 is being disinfected. If uninterrupted, eventually the disinfection will complete and the luminaires 10G-L will power down: either at their own determination of sufficient disinfection, or at the determination of the primary relay pack 111. However, the primary relay pack 111 may control the luminaires 10G-L to stop emitting the disinfection light 17 in response to one or more of: a visual inspection signal 170B produced by an arming switch 56A-B indicating OFF, a room state signal 170F produced by a room sensor 45M-N indicating OFF, an occupancy signal 170G produced by a occupancy or room sensor 45G-L indicating OFF or a security challenge response signal 171A produced by a security challenge device 1101 indicating OFF. These control signals 170B,F,G and security challenge response signal 171A in this context all indicate that either a human 185 is sensed in the physical space 2, and that the luminaires 10G-L need to stop emitting disinfection light 17.

The occupancy sensors can be room sensors 45G-L that are integrated within the luminaires 10G-L (see FIG. 3). When the occupancy signals 170G-L produced by the occupancy sensors 45G-L indicate a respective vicinity 180G-L is occupied, this causes the switching device 110 to either revoke power from all luminaires 10G-L when a human 185 is detected in the respective vicinity 180G-L. Alternatively, the switching device 110 may only revoke power from a single respective luminaire 10G-L when a human 185 is detected in the single respective vicinity 180G-L of the single luminaire 10G.

FIG. 10B is a block flowchart diagramming of the authenticated safe lockout protocol interleaving strategy 1090. As noted in FIG. 10A, step 1005, step 1010, and step 1015 of the authenticated lockout protocol 1001 are to be performed sequentially in what can be labelled an inspection sequence 1098. Step 1025, step 1030, and step 1035 are to be performed sequentially as well, in what can be labelled a challenge sequence 1099. Step 1040 is performed after both step 1015 and step 1035 are performed. The inspection sequence 1098 is independent of the challenge sequence 1099, and so consequently the two sequences may be interleaved chronologically, so long as step 1005, step 1010, and step 1015 remain in sequence, and step 1025, step 1030, and step 1035 remain in sequence, respectively.

Therefore, block 1091 through block 1097 indicate the chronological order of the authenticated safe lockout protocol 1001, showing possible interleaving strategies. Block 1091 is the first step chronologically, block 1092 is the second step chronologically, block 1093 is the third step chronologically, block 1094 is the fourth step chronologically, block 1095 is the fifth step chronologically, block 1096 is the sixth step chronologically, and block 1097 is the seventh step chronologically. In the authenticated safe lockout protocol 1001, step 1040 is always the last step, and so in the authenticated safe lockout protocol 1001 interleaving strategy 1090, step 1040 is always within block 1097.

Step one, or block 1091, either includes step 1005, the first step of the inspection sequence 1098, or step 1025, the first step of the challenge sequence. Step two, or block 1092, includes either the second step of the sequence included in block 1091, or the first step of the sequence not included in block 1091. For example, if block 1091 includes step 1005, then block 1092 includes either step 1025 or step 1010. Step three, or block 1093, includes either the third step of the sequence with steps included in both block 1091 and block 1092, the second step of either sequence if block 1091 and block 1092 include steps from different sequences, or the first step of the sequence with no steps included in either block 1091 or block 1092. Continuing the previous example, if block 1092 included step 1025 of the inspection sequence 1098, then block 1093 includes either step 1010 of the inspection sequence 1098, or step 1030 of the challenge sequence 1099. Step four, or block 1094, includes the earliest unblocked step from the inspection sequence 1098 or the earliest unblocked step from the challenge sequence 1099 that does not appear in block 1091, block 1092, or block 1093. Step five, or block 1095, includes the earliest unblocked step from the inspection sequence 1098 or the earliest unblocked step from the challenge sequence 1099 that does not appear in block 1091, block 1092, block 1093, or block 1094. Step six, or block 1096, includes the unblocked step from either the inspection sequence 1098 or the challenge sequence 1099 that does not appear in in block 1091, block 1092, block 1093, block 1094, or block 1095, which will be either step 1015 or step 1035. Step 7, or block 1097, will always include step 1040.

The specific sequence of the steps of the authenticated safe lockout protocol 1001 interleaving strategy 1090 can either be restricted as part of a specific embodiment, or enforced by the owner of the antimicrobial system 1 as part of the system configuration, for example by not allowing step 1025 to occur before step 1015. Alternatively, the operator of the antimicrobial system 1 may have some freedom to determine an interleaving order, to accomplish the authenticated safe lockout protocol 1001 most efficiently.

FIG. 11 is a block diagram of a security challenge device 1101 of the antimicrobial system 1. The security challenge device 1101 includes a micro-control unit (MCU) 1129, drive/sense circuitry 46, user interface elements 1161, and an optional security challenge device communication interface system 1155. The user interface elements 1161 of the security challenge device 1101 at least include a security challenge device operator interface 1161. This security challenge device operator interface 1161 collects the security challenge input from the operator.

Therefore, the security challenge operator interface 1161 takes on a form dependent upon the security challenge which the operator is providing the security challenge input. If the security challenge input includes entry of a password or both a username and password, then the security challenge device operator interface 1161 can include a keypad 1211, keyboard, or a touchscreen, like the touch screen display 811 of the control station 20. If the security challenge input includes insertion of a physical key, then the security challenge device operator interface 1161 can include a lock cylinder. If the security challenge input includes presentation of an identification badge, then the security challenge device operator interface can include a card swipe reader 1216 or a near field communication (NFC) wireless interface. If the security challenge input includes a retinal scan, then the security challenge device operator interface 1161 can include a retinal scanner 1206. If the security challenge input includes a facial scan, then the security challenge device operator interface 1161 can include a camera utilizing facial recognition. If the security challenge input includes a fingerprint scan, then the security challenge device operator interface 1161 can include a fingerprint reader 1201. For authentication forms requiring an operator physically interface with the security challenge device operator interface 1161, the surface of the security challenge device operator interface 1161 can incorporate antimicrobial coatings, finishings, and materials: for example, on push buttons, touch screens, touchpads, and any exposed surface.

Additionally, any of these security challenge device operator interfaces 1161 can be implemented virtually, for example utilizing a mobile device 25 or a touch screen display 811 to present a virtual keypad 1211. Furthermore, the security challenge device 1101 itself, when embedded in another device within the antimicrobial system 1, may completely utilize the existing hardware of the device. For example, within an arming switch 56, the security challenge device processor 1130 may be virtually implemented within the arming switch processor 730, and the security challenge device memory 1131 may be virtually implemented within the arming switch memory 731. Functionally, the security challenge device 1101 is reduced to the security challenge programming, and is executed by the hardware of the antimicrobial system 1 device into which the security challenge programming 1132 is installed.

As shown, MCU 1129 includes security challenge device processor 1130 and security challenge device memory 1131 to implement the authenticated safe lockout protocol 1001, the distributed disinfection control programming 532, the security challenge device programming 1132, the mobile device security challenge programming 1133 if embedded in a mobile device 25, and the cloud computing device security challenge programming 1134 if embedded in a cloud computing device 266, described herein. The circuitry, hardware, and software of the security challenge device 1101 is similar to the luminaire 10 of FIG. 4A, including the line power source 101, non-line power source 102, power supply 105, power distribution 125, and the security challenge device communication interface system 1155. The security challenge device 1101 can include a security challenge device communication interface system 1155 like the luminaire communication interface system 155 of FIG. 4A. However, the circuitry of the security challenge device 1101 can be extremely simple, potentially providing a binary switch value (on/off) via current or voltage interruption to the switching device 110 based upon whether the security challenge device operator interface 1161 (e.g. a toggle switch, button, etc.) of the security challenge device 1101 is activated.

As described herein, an antimicrobial system 1 includes a luminaire 10A configured to emit a disinfection light 17 in an ultraviolet (UV) band for disinfecting a vicinity 180 of a physical space 2 of a target pathogen 187 that is exposed to the disinfection light 17. The antimicrobial system 1 further includes a switching device 110 that includes a primary relay pack 111.

Antimicrobial system 1 further includes a control station 20 of FIG. 8 located outside the physical space 2 and coupled to the switching device 110. The control station 20 includes a disinfection initiation user interface element 862 to produce an arming initiation signal 170A based on a first input from an operator, an arming completion interface user element 863 to produce an arming completion signal 170C based on a third input from the operator, and a disinfection commencement user interface element 864 to produce a disinfection commencement signal 170D based on a fourth input from the operator.

The antimicrobial system 1 further includes an arming switch 56A located inside the physical space 2, coupled to the switching device 110. The arming switch 56A is configured to produce a visual inspection signal based on a second input from the operator. The antimicrobial system 1 further includes a room sensor 45A located inside the physical space 2 and coupled to the switching device 110. The room sensor 45A is configured to produce a room state signal 170F in response to detecting occupancy of the vicinity 180 of the physical space 2 by a human 185.

The antimicrobial system 1 further includes a security challenge device 1101. The security challenge device 1101 includes a security challenge device communication interface 1155. The security challenge device 1101 further includes a security challenge device operator interface 1161 to receive a security challenge input from an operator. The security challenge device 1101 further includes a security challenge device processor 1130 coupled to the security challenge device network communication interface 1155 and the security challenge device operator interface 1161. The security challenge device 1101 further includes a security challenge device memory 1131 coupled to the security challenge device processor 1130. The security challenge device 1101 further includes security challenge device programming 1132 in the security challenge device memory 1131.

Execution of the security challenge device programming 1132 in the by the security challenge device processor 1130 configures the security challenge device 1101 to perform the following functions. First receive the security challenge input from the operator via the security challenge device operator interface 1161. Second, in response to receiving the security challenge input, generate a security challenge response signal 171A. Third, send, via the security challenge device communication interface 1155, the security challenge response signal 171A to enable the primary relay pack 111 to control power to the luminaire 10A to emit the disinfection light 17 via the primary relay pack regulator 511.

In an example, the arming initiation signal 170A, the visual inspection signal 170B, the arming completion signal 170C, the security challenge response signal 171A, and the disinfection commencement signal 170D are disinfection control signals produced in a disinfection control signal sequence, for example, successively in order. Each of the disinfection controls signals 170A-D, 171A are switched between an on signal or an off signal by the operator to control power to the disinfection light source 16 to emit the disinfection light 17 via the primary relay pack regulator 511. In response to each of the disinfection controls signal 170A-D, 171A being switched to the on signal by the operator within a limited time (e.g., 5 minutes), the primary relay pack regulator 511 powers on the disinfection light source 16 to emit the disinfection light 17. In response to one or more of the disinfection controls signals 170A-D, 171A being switched to the off signal, the primary relay pack regulator 511 powers off the disinfection light source 16 to stop emitting the disinfection light 17.

Additionally, the security challenge input includes entry of a password, or both a username and the password; an insertion of a physical key; a presentation of an identification badge; an authorization by an authentication application 1125 on a mobile device 25; an identification of a visible-light communication (VLC) signal 171B; a retinal scan generated by a retinal scanner 1206; a facial scan generated by a camera with facial recognition; a fingerprint scan generated by a fingerprint reader 1201; or a combination thereof. The security challenge device operator interface 1161 includes a keypad 1211 or a keyboard; a touchscreen or touch screen display 811; a lock cylinder; a card swipe reader 1216; a near field communication (NFC) wireless interface like the wireless communication security challenge device 1157; a mobile device 25; a retinal scanner 1206; a camera with facial recognition; a fingerprint reader 1201; or a combination thereof.

In one example, the security challenge input is the first input, the second input, the third input, or a fifth input from the operator. The control station 20 produces the disinfection commencement signal 170D based on the fourth input from the operator and the security challenge response signal 171A. The security challenge device 1101 is integrated with the luminaire 10A, the switching device 110, the control station 20, the arming switch 56A, the room sensor 45A, or the mobile device 25.

Alternatively, the security challenge device 1101 is a standalone device separate from the luminaire 10A, the switching device 110, the control station 20, the arming switch 56A, and the room sensor 45A.

As a particular example, the security challenge device 1101 is integrated with the control station 20 such that the control station 20 includes the security challenge device 1101. The security challenge input is a fifth input from the operator, and the security challenge response signal 171A is generated in response to the fifth input from the operator. This example illustrates a scenario where, in addition to the control station 20 having a disinfection initiation user interface element 862, arming completion user interface element 863, and disinfection commencement user interface element 864 among the user interface elements 861, the security challenge device operator interface 1161 is among the user interface elements 861 as a separate element, to have a separate input in addition to the inputs for the disinfection initiation user interface element 862, arming completion user interface element 863, and disinfection commencement user interface element 864.

Alternatively, the security challenge device is integrated with the control station 20 such that the control station 20 includes the security challenge device 1101, and the security challenge input is the first input, the third input, or the fourth input. This example illustrates a scenario where, rather than the operator pushing a button to send the control signals 170A,C,D from the control station 20, the operator must complete the security challenge of the security challenge device 1101. Completing the security challenge of the security challenge device 1101 both sends the security challenge response signal 171A, as well as the control signal 170A,C,D for which the security challenge device 1101 has replaced the user interface element. If the security challenge device 1101 has replaced the disinfection initiation user interface element 862, the security challenge device sends the arming initiation signal 170A as well as the security challenge response signal 171A. If the security challenge device 1101 has replaced the arming completion user interface element 863, the security challenge device sends the arming completion signal 170C as well as the security challenge response signal 171A. If the security challenge device 1101 has replaced the disinfection user interface element 864, the security challenge device sends the disinfection commencement signal 170D as well as the security challenge response signal 171A.

As an additional alternative, the security challenge device 1101 is integrated with the arming switch 56A such that the arming switch 56A includes the security challenge device 1101, and the security challenge input is the second input. This example illustrates a scenario where, rather than the operator pushing a button to send the visual inspection signal 170B from the arming switch 56A, the operator must complete the security challenge of the security challenge device 1101. Completing the security challenge of the security challenge device 1101 both sends the security response signal 171A, as well as the visual inspection signal 170B.

As per the example in FIG. 4B, the security challenge device 1101 is the standalone device separate from the luminaire 10A, the switching device 110, the control station 20, the arming switch 56A, and the room sensor 45A. The standalone device is a mobile device 25, that includes a mobile device network communication interface 186 configured for a short range wireless communication over a short range network 399. A mobile device processor 190 coupled to the mobile device network communication interface 186, and an image sensor 181 coupled to the mobile device processor 190, configured to receive a visible light communication (VLC) over a VLC band 407. A mobile device memory 191 accessible to the mobile device processor 190, and mobile device security challenge programming 492 in the mobile device memory 191. The luminaire 10A further includes a general illumination light source 18 and a light modulator 416 to modulate a visible light emitted from the general illumination light source 18 for the VLC over the VLC band 407 to transmit a security challenge. The security challenge is transmitted within a security challenge signal 171B.

Execution of the mobile device security challenge programming 492 by the mobile device processor 190 configures the mobile device 25 to perform the following functions. Receive, via the image sensor 181, over the VLC band 407, the security challenge. In response to receiving the security challenge, generate the security challenge response signal 171A. In some examples, there is no direct input required from the operator, as the security challenge is itself to be present within the illumination lighting 19. Thus, the security challenge response signal 171A will just evidence the fact that the mobile device 25 received the security challenge within the security challenge signal 171B over the VLC band 407.

As another alternative, the security challenge device 1101 is the standalone device separate from the luminaire 10A, the switching device 110, the control station 20, the arming switch 56A, and the room sensor 45A. The standalone device is a mobile device 25, that includes a mobile device network communication interface 186 configured for a short range wireless communication over a short range network 399. A mobile device processor 190 coupled to the mobile device network communication interface 186, and an image sensor 181 coupled to the mobile device processor 190, configured to receive a visible light communication (VLC) over a VLC band 407. A mobile device memory 191 accessible to the mobile device processor 190, and mobile device security challenge programming 492 in the mobile device memory 191. The arming switch 56A or the control station 20 further includes a radio frequency transceiver 156A-B configured for the short wireless communication over the short range wireless communication network 399 to transmit a security challenge.

Execution of the mobile device security challenge programming 492 by the mobile device processor 190 configures the mobile device 25 to perform the following functions. Receive, via the mobile device network communication interface 186, over the short range wireless network 399, the security challenge, and in response to receiving the security challenge, generate the security challenge response signal 171A. In some examples, there is no direct input required from the operator, as the security challenge is itself to be present within the short range wireless communication network 399 of the arming switch 56A or the control station 20. Thus, the security challenge response signal 171A will just evidence the fact that the mobile device 25 received the security challenge within the security challenge signal 171B over the short range wireless communication network 399.

A different example shows the security challenge device 1101 includes a mobile device 25 and a cloud computing device 266. The mobile device 25 includes a mobile device network communication interface 186 configured for network communication over a wide area network 255. A mobile device processor 190 coupled to the mobile device network communication interface 186, a mobile device memory 191 accessible to the mobile device processor 190, and mobile device security challenge programming 492 in the mobile device memory 191. Execution of the mobile device security challenge programming 492 by the mobile device processor 191 configures the mobile device 25 to perform the following functions. Transmit the security challenge input to the cloud computing device 266 via the mobile device network communication interface 186, over the wide area network 255, the security challenge input transmitted from the mobile device 25. The security challenge input is transmitted within the security challenge input signal 171C. In response to receiving the security challenge input, generate the security challenge response signal 171A.

The primary relay pack 111 includes a primary relay pack regulator 511 coupled to the luminaire 10A and configured to control power to the luminaire 10A. The primary relay pack 111 further includes a primary relay pack processor 530 coupled to the primary relay pack regulator 511 and configured to control the primary relay pack regulator 511. The primary relay pack 111 further includes a primary relay pack memory 531 accessible to the primary relay pack processor 530. The primary relay pack 111 further includes distributed disinfection control programming 532 in the primary relay pack memory 531. Execution of the distributed disinfection control programming 532 by the primary relay pack processor 530 configures the primary relay pack 111 to perform the following functions. In response to the security challenge response signal 171A, control power to the luminaire 10A to emit the disinfection light 17 via the primary relay pack regulator 511. In response to the control station 20 producing the arming initiation signal 170A, confirm the security challenge device 1101 is able to generate the security challenge response signal 171A.

The function to control power to the luminaire 10A to emit the disinfection light 17 further includes to control power to the luminaire 10A to stop emitting the disinfection light 17 in response to the security challenge response signal 171A generated by the security challenge device 1101 indicating to turn off the disinfection light 17.

In an example where the antimicrobial system includes a plurality of luminaires 10A-F, execution of the distributed disinfection control programming 532 by the primary relay pack processor 530 configures the primary relay pack 111 to perform the following functions. Control each luminaire 10A-F to stop emitting the disinfection light 17 in response to the security challenge response signal 171A generated by the security challenge device 1101 indicating to turn off the disinfection light.

In another example, the antimicrobial system 1 includes a second security challenge device 1101B configured to generate a second security challenge response signal 171D based on a second security challenge input from the operator. The second security challenge device 1101B is in addition to the first security challenge device 1101A. The function of the distributed disinfection control programming 532 to control power to the luminaire 10A to emit the disinfection light 17 further includes to control power to the luminaire 10A to emit the disinfection light 17 in response to both the security challenge response signal 171A generated by the security challenge device 1101A indicating to turn on the disinfection light, and the second security challenge response signal 171D produced by the second security challenge device 1101B indicating to turn on the disinfection light 17.

FIG. 13 is a block diagram of a cloud computing device 266 of the antimicrobial system 1. Cloud computing device 266 includes a micro-control unit (MCU) 1329 and n cloud computing device communication interface system 1355. The cloud computing device 266 is off-premises 265, and cannot be directly interacted with by an operator in the physical space 2. Therefore, the cloud computing device 266 can generally implement a network security challenge 1134, where the cloud computing device 266 validates a security challenge input in a security challenge input signal 171C sent by another device in the antimicrobial system. Alternatively, the cloud computing device 266 may be used as a forwarding device, sending a security challenge input signal 171C sent by a mobile device 25 not on the disinfection light control network 7, to a security challenge device 1101 on the disinfection light control network 7 for validation and generation of the security challenge response signal 171A.

As shown, MCU 1329 includes a cloud computing device processor 1330 and cloud computing device memory 1331 to implement the authenticated safe lockout protocol 1001 and the distributed disinfection control programming 532 described herein. The circuitry, hardware, and software of the cloud computing device 266 is similar to the luminaire 10 of FIG. 4A, including the line power source 101, non-line power source 102, power supply 105, power distribution 125, and the cloud computing device communication interface system 1355. The cloud computing device 266 can include a cloud computing device communication interface system 1355 like the luminaire communication interface system 155 of FIG. 4A.

Figure 14:
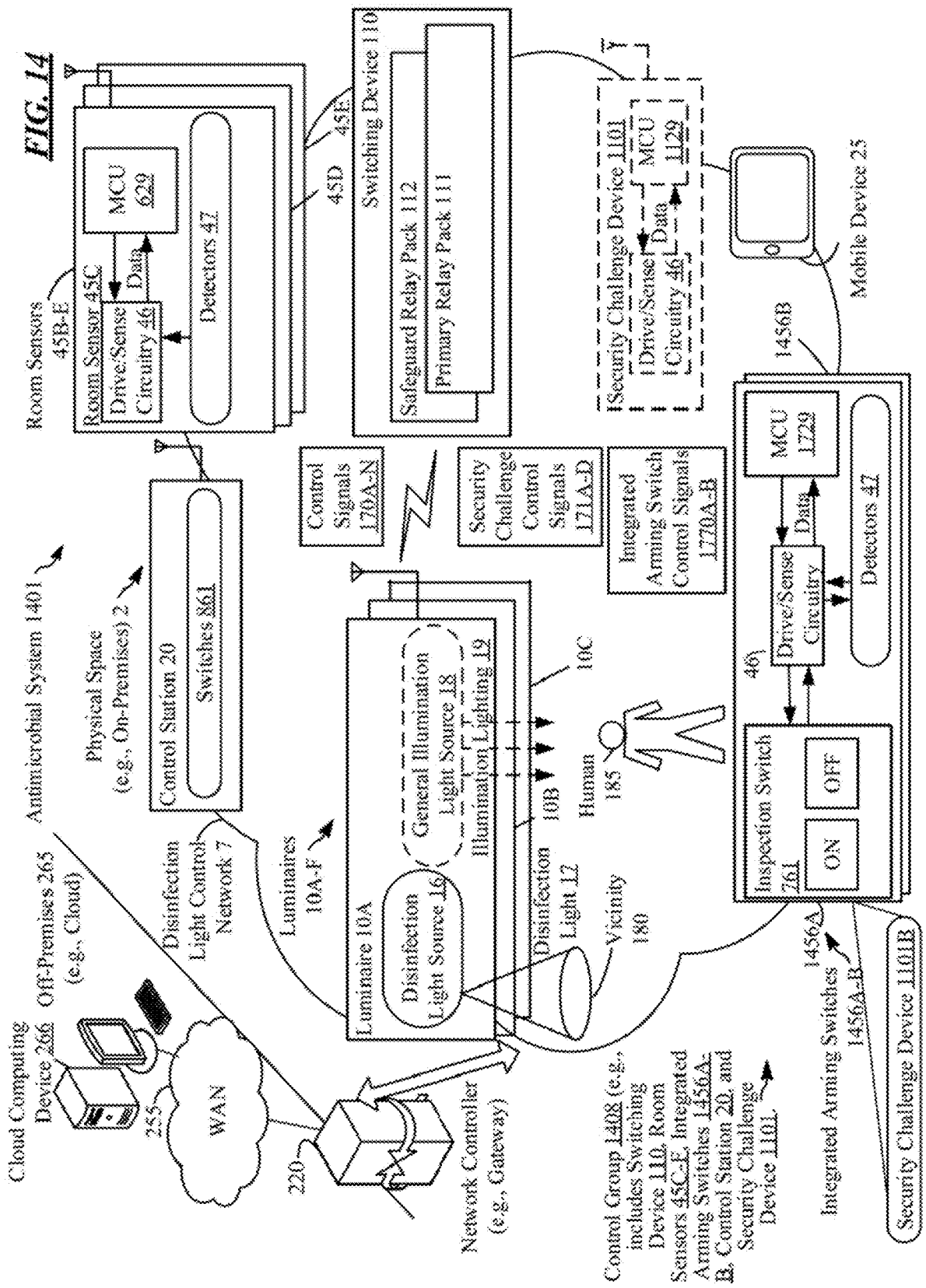
FIG. 14 is a high-level functional block diagram of an example of an antimicrobial system that distributed disinfection controls includes integrated arming switches.

FIG. 14 is a high-level functional block diagram of an example of an antimicrobial system 1 that includes six luminaires 10A-F like that of FIG. 4 and a control group 1408. FIG. 14 is a variation on FIG. 1A, illustrating an antimicrobial system 1 utilizing integrated arming switches 1456A-B. Certain components, such as some of the internal components of the primary relay pack 111, control station 20, and luminaire 10A have been omitted from FIG. 14 to improve readability—these omitted components are nevertheless present in the same manner as within the antimicrobial system 1 depicted in FIG. 14.

In particular, FIG. 14 differs from FIG. 1A in the inclusion of integrated arming switches 1456A-B. These integrated arming switches 1456A-B take on the functional roles of both the arming switches 56A-B of FIG. 1A, as well as the room sensors 45A,F of FIG. 1A. Consequently, in FIG. 14, arming switches 56A-B have been removed as compared to FIG. 1A, and room sensors 45A,F have been removed as compared to FIG. 1A. Room sensors 45B-E remain. Antimicrobial system 1401 is substantially the same as antimicrobial system 1 other than noted differences herein, and implements the authenticated safe lockout protocol 1001. However, antimicrobial system 1401 further enhances the authenticated safe lockout protocol 1001 with the streamlined safe lockout protocol 1800 (see FIG. 18). As described herein, the authenticated safe lockout protocol 1001 in combination with the streamlined safe lockout protocol 1800 (see FIG. 18) also includes communications in support of turning a disinfection light source 16 of luminaires 10A-F on/off, adjusting intensity, sensor trip events, and other control signals 170A-N, integrated arming switch control signal 1770A-B, and security challenge control signals 171A-D. As shown, the control signals 170A-N, integrated arming switch control signals 1770A-B, and security challenge control signals 171A-D can be received from the control group 1408 via the disinfection light control network 7.

Figure 18:
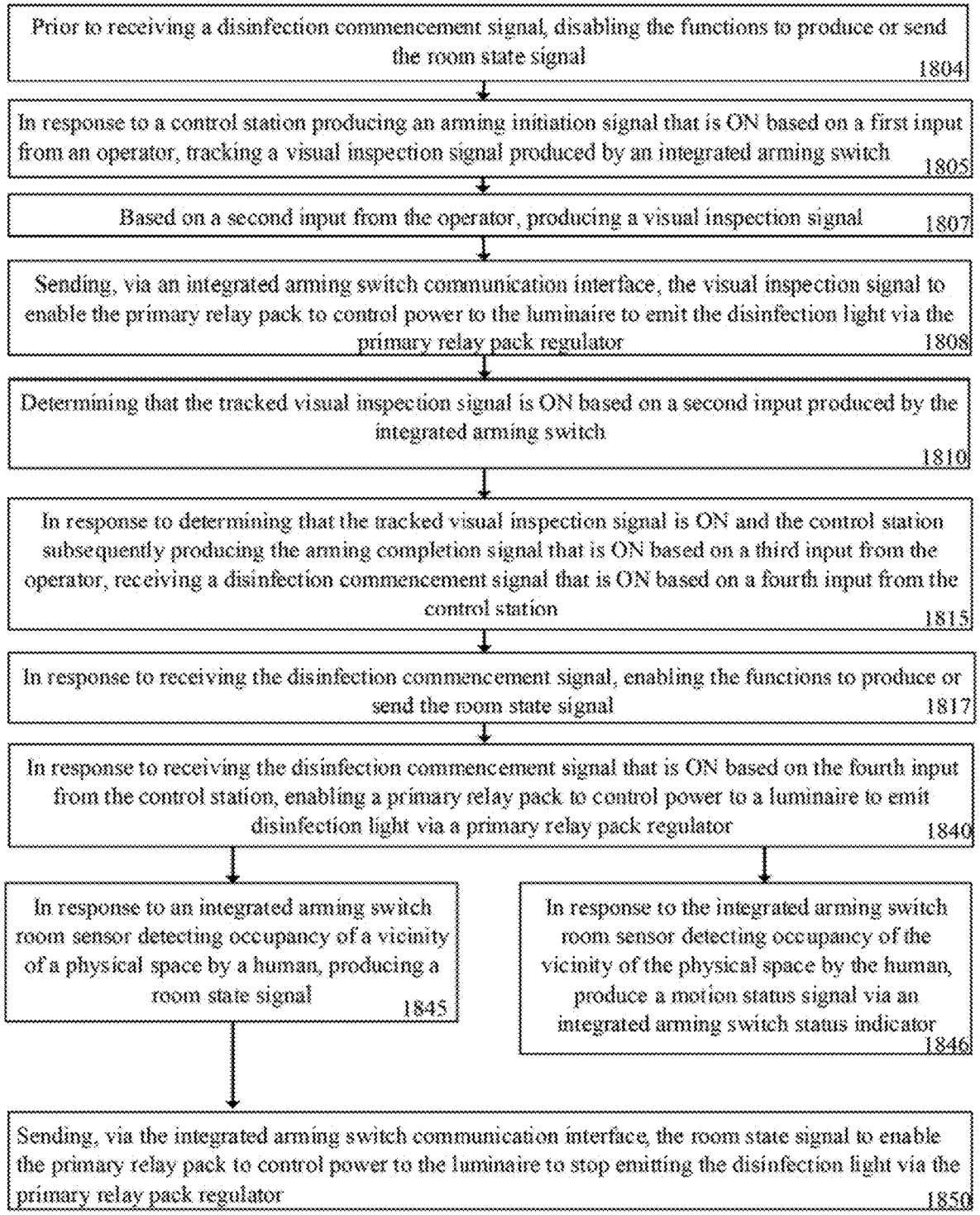
FIG. 18 is a block diagram of a safe lockout protocol of the antimicrobial system utilizing integrated arming switches.

The control group 1408 includes room sensors 45B-E, which are occupancy, motion, ozone, daylight, or audio detector(s) 47, to enable controls for occupancy and intensity adjustment of the disinfection light 17. The integrated arming switches 1456A-B are included within the control group 1408 in order to allow an operator to input into the antimicrobial system 1401 that no human 185 is within the vicinity 180 of any disinfection light 17. Additionally, the integrated arming switches 1456A-B include occupancy, motion, ozone, daylight, or audio detector(s) 47, to enable controls for occupancy and intensity adjustment of the disinfection light 17. The control station 20 includes user interface elements (e.g., switches 861) to allow an operator to activate the arming switches 56A-B, and ultimately energize the luminaires 10A-F in order to emit disinfection light 17. Setting aside utilizing integrated arming switches 1456A-B rather than arming switches 56A-B and room sensors 45A-B, control group 1408 operates substantially the same as control group 8, again other than noted differences herein. The control group 1408 members communicating on the disinfection light control network 7 are designed to perform an authenticated safe lockout protocol 1001 of FIG. 10A as well as the streamlined safe lockout protocol 1800 of FIG. 18, confirming that no human 185 is within the physical space 2 once the disinfection light 17 is activated. Once the authenticated safe lockout protocol 1001 is completed, the switching device 110 provides power to the luminaires 10A-F. Once the full the streamlined safe lockout protocol 1800 of FIG. 18 is completed, the switching device 110 will stop providing power to the luminaires 10A-F.

The integrated arming switches 1456A-B, much like the arming switches 56A-B of FIG. 1A, are mounted in a physical space 2 as needed to validate that all areas of the physical space 2 have been visually inspected for human(s) 185. The integrated arming switches 1456A-B functionally double as room sensors 45A-B of FIG. 1A, and will disable the luminaires 10A-F that emit disinfection light 17 when someone enters the room during the disinfectant period. Alternatively, some integrated arming switches 1456A-B may not be mounted near the door, but rather may be mounted on the room corners or walls, in order to provide overlapping coverage. In this example, the switching device 110 monitors the status of all networked devices, and enables power delivery to the luminaires 10A-F only after all devices of the control group 1408 are discovered, and all of the following conditions are confirmed in the system. First, a healthy hardware status of each device of the control group 1408 broadcasting on the disinfection light control network 7, meaning all devices are discovered and communicating with other devices. Second, a healthy network status between each device in the antimicrobial system 1401, for example no errors, dropped packets, nor significant noise detected. Third, all integrated arming switches 1456A-B are functional. Fourth, no room state signals 170F of FIG. 6 indicating human(s) 185 (e.g., people) or animals are present in the vicinity 180 of the physical space are detected from room occupancy sensor type of room sensors 45B-E. Fifth, no integrated room state signals 1770A of FIG. 17 indicating human(s) 185 (e.g., people) or animals are present in the vicinity 180 of the physical space are detected from integrated arming switches 1456A-B. Sixth, all integrated arming switches 1456A-B are enabled. Seventh, any security challenge devices 1101A-B are enabled.

The detectors 47 of the integrated arming switches 1456A-B may be further improved with a proximity and ranging sensor based on radar, UWB, BLE, WiFi active infrared based technology, or other sensory technology disclosed herein, in order to count occupants during regular room usage time of the vicinity 180 of the physical space 2, so that this information can be processed by the control group 1408 to automatically calculate the required dosage disinfection time necessary to sanitize the room. These proximity and ranging sensors may be used in conjunction with other occupancy sensing technologies or be used independently and serve as both room sensors and as occupancy counters. Primary relay pack 111, safeguard relay pack 112, or both may be integrated into the integrated arming switches 1456A-B.

Integrated arming switches 1456A-B and the control group 1408 can communicate integrated arming switch control signal(s) 1770A-B, control signals 170A-N, and security challenge control signal(s) 171A-D for the disinfection light 17 over a wireless disinfection light control network 7 (e.g., 900 MHz) and accordingly each include a first radio 156A in the sub-GHz range. Alternatively, the integrated arming switches 1456A-B may be partially or completely wired, and the luminaires 10A-F and the control group 1408 communicate over wired data connections. Furthermore, some integrated arming switch control signals 1770A-B can be communicated over energy-providing wired connections, for example in the presence or absence of voltage or current, or in the timing of the presence or absence of voltage or current.

Figure 15:
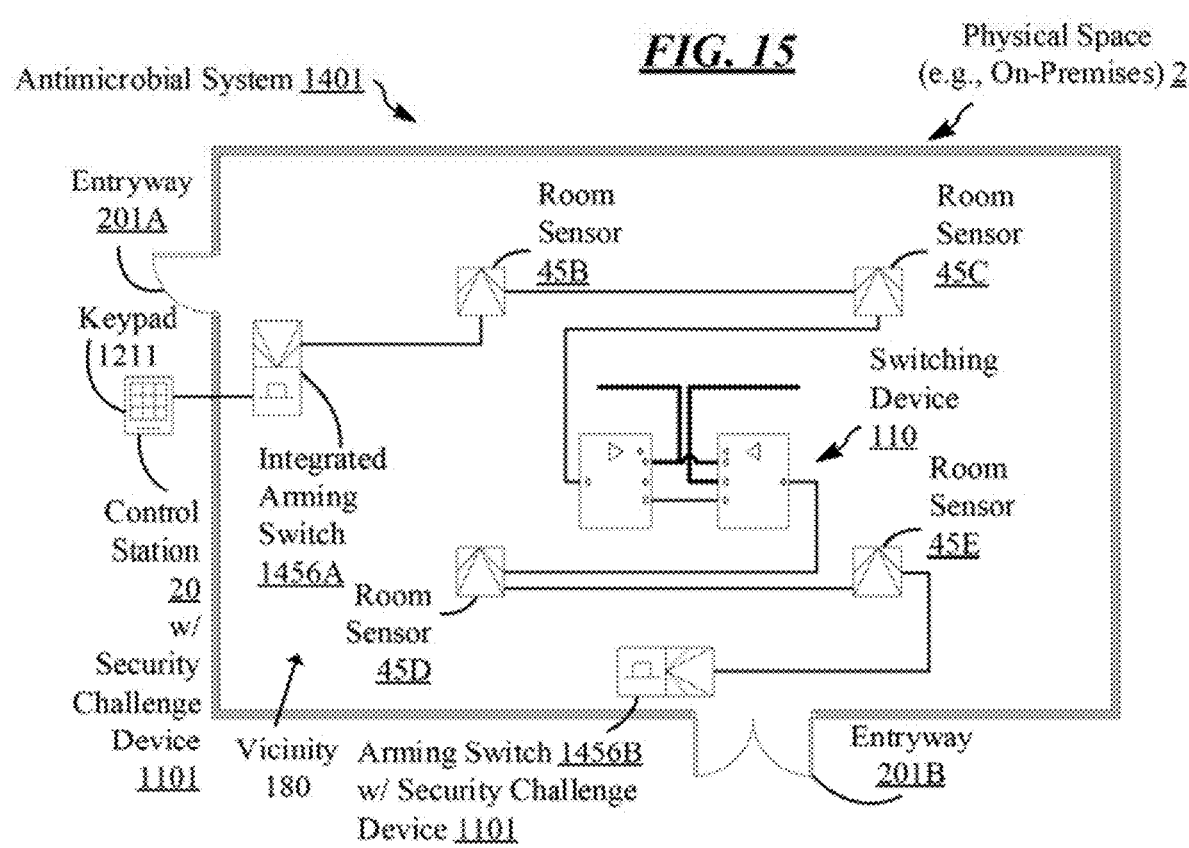
FIG. 15 is a high-level functional block diagram of an example of an antimicrobial system that includes luminaires with external sensors, integrated arming switches, and data connections.

FIG. 15 is a high-level functional block diagram of an example of an antimicrobial system 1401 that includes luminaires 10A-F with external sensors, integrated arming switches 1456A-B, and data connections. FIG. 15 is a variation on FIG. 2A, illustrating an antimicrobial system 1401 utilizing integrated arming switches 1456A-B. The antimicrobial system 1401 does not vary from antimicrobial system 1 with respect to the electrical connections, as the electrically-connected components are the luminaires 10A-F, the primary relay pack 111, safeguard relay pack 112, and the line power source 101. Consequently, a figure variation on FIG. 2B for antimicrobial system 1401 is omitted.

The antimicrobial system 1401 includes four room sensors 45B-E: in addition, two room sensors are within the integrated arming switches 1456A-B near the two entryways 201A-B, and the remaining four are room sensors 45B-E mounted in the ceiling. In this example, these four room sensors 45B-E and integrated arming switches 1456A-B form part of the disinfection light control network 7 by being wired together, for example via an RS485 or Ethernet connection. The connections between the four room sensors 45B-E, the integrated arming switches 1456A-B, and the rest of the disinfection light control network 7 do not need to be digital messaging connections. For example, each integrated arming switch 1456A-B can have two contact closures which are connected back to inputs on the primary relay pack 111: a first contact closure could close for a limited time when the inspection switch 761 has been pressed, and the second contact closure could close when detector 47 does not detect occupancy of the vicinity 180. The first contact closure closing would act as the visual inspection signal 1770A to the primary relay pack 111, and the second contact closure opening would act as the room state signal 1770B. Alternatively, the integrated arming switches 1456A-B could be connected together using one or more current loops configured such that the circuit within the one or more current loops is not completed, and current does not flow through the one or more current loops, unless all inspection switches 761 of the integrated arming switches 1456A-B have been pressed within a certain time period while the detectors 47 of the integrated arming switches 1456A-B do not detect occupancy of the vicinity 180. These four room sensors 45B-E and integrated arming switches 1456A-B are also joined to the switching device 110 by a wired data connection, which brings the switching device 110, primary relay pack 111, and safeguard relay pack 112 onto the disinfection light control network 7. The integrated arming switches 1456A-B are located near the entryways 201A-B to the physical space 2 containing the vicinity 180, and the detectors 47 of these integrated arming switches 1456A-B are pointed to detect if a human 185 enters or leaves the physical space 2. The four remaining room sensors 45B-E are ceiling-mounted, and are pointed to generally detect motion within the physical space 2. The room sensors 45B-E and integrated arming switches 1456A-B are, when necessary, pointed with overlapping sensed areas, rather than pointed with gaps between a sensed area and the area of the physical space 2.

Though the integrated arming switches 1456A-B are located near the entryways 201A-B, the integrated arming switches 1456A-B can be placed anywhere that a), after a human 185 stands in the nearby surrounding area of each integrated arming switch 1456A-B and performs a visual inspection, the entire physical space 2 has been visually inspected for occupants, and b) allows for the detectors 47 of the integrated arming switches 1456A-B to assist in detecting motion within the physical space 2. More integrated arming switches 1456 can be used than two integrated arming switches 1456A-B, and if only one integrated arming switch 1456A is needed to meet the standing visual inspection requirement, only one integrated arming switch 1456A is required. More integrated arming switches 1456 than are minimally required may be used, in order to enforce improved visual inspection by the operator performing the visual inspections in front of the arming switches 56A-B. The antimicrobial system 1401 may also utilize both integrated arming switches 1456 and arming switches 56 to meet the standing visual inspection requirement. Arming switches 56 used in concert with integrated arming switches 1456 may be called standalone arming switches 56 in order to distinguish the integrated arming switch 1456 from the arming switch 56. Additionally, room sensors 45 used in concert with integrated arming switches 1456 may be called standalone room sensors 45 to distinguish the integrated arming switch room sensor 1745 of FIG. 17 from the room sensor 45.

The integrated arming switches 1456A-B have additional components as described in FIG. 17, but can also minimally be a user interface element, such as simple inspection switch 761 and passive sensory detector 47: one which sends a visual inspection signal 1770A when the inspection switch 761 of the integrated arming switch 1456A is triggered; sends no signal when the inspection switch 761 of the integrated arming switch 1456A is not triggered; sends a room state signal 1770B when the detector 47 of the integrated arming switch 1456A is triggered; and sends no signal when the detector 47 of the integrated arming switch is not triggered. The example inspection switches 761 of the integrated arming switches 1456A-B are simple pushbutton switches, but the inspection switch 761 could by any kind of user interface element; the integrated arming switches 1456A-B could require a key, or a security challenge device operator interface 1161 such as a passphrase or PIN entry device like a keypad 1211, a badge scan or swipe into a card swipe reader 1216, or fingerprint scan by a fingerprint reader 1201, all shown in greater detail in FIGS. 11 and 12. Additionally, an integrated arming switch 1456A can implement a different security challenge, or could implement no security challenge or key requirement at all, even if another integrated arming switch 1456B or arming switch 56A implements a security challenge or key requirement. The inspection switch 761 could also be implemented virtually, as a digital object an operator interacts with via a computing component like the touch screen device 811 of FIG. 8.

Figure 16:
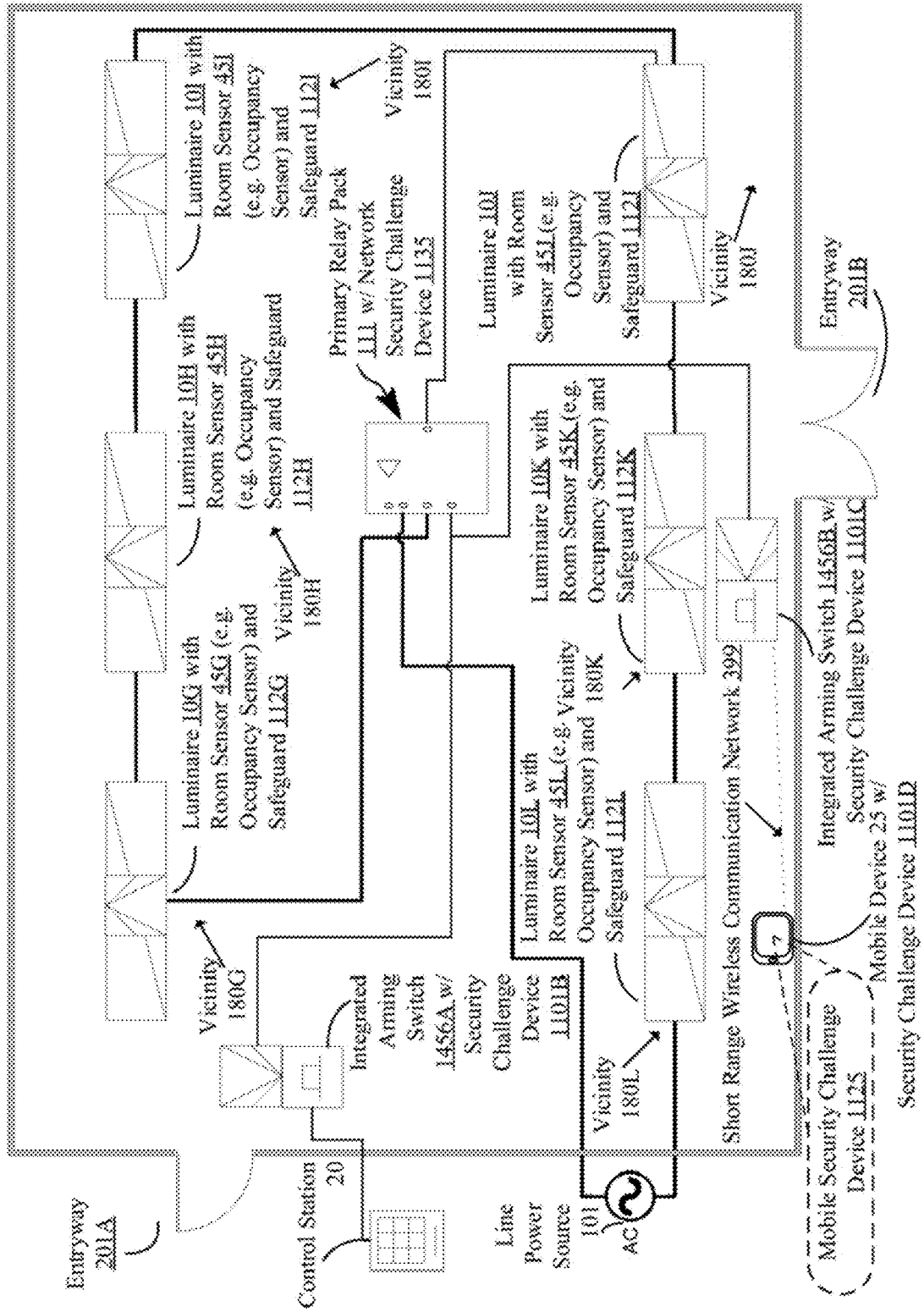
FIG. 16 is a high-level functional block diagram of an alternative example of an antimicrobial system that includes luminaires with integrated sensors, integrated arming switches, and integrated switching devices.

FIG. 16 is a high-level functional block diagram of an alternative example of an antimicrobial system 1 that includes luminaires 10G-L with integrated room (e.g. occupancy) sensors 45G-L and integrated switching devices (e.g. safeguard relay packs 112G-L.) FIG. 16 is a variation on FIG. 3, illustrating an antimicrobial system 1401 utilizing integrated arming switches 1456A-B. Therefore this example is also similar to the example of FIG. 15, as FIG. 16 relates to FIG. 15 in an analogical manner as FIG. 3 relates to FIG. 2A. However, the only difference between FIG. 16 and FIG. 3 is the use of integrated arming switches 1456A-B, which implement the security challenge device 1101 split between two security challenge devices 1101B-C within the integrated arming switches 1456A-B. These security challenge devices 1101B-C implement the wireless communication security challenge device 1157 shown in FIG. 7. These example wireless communication security challenge devices 1157 implement near-field communication (NFC) as described in FIG. 3. The use of integrated arming switches 1456A-B allows for the data connection of the integrated arming switches 1456A-B to connect directly to the primary relay pack 111, rather than route indirectly through a room sensor 45M-N. Reducing the number of connection points in a series reduces the number of failure points within the antimicrobial system 1401, improving system robustness and overall safety. The integrated arming switches 1456A-B are able to directly send integrated arming switch control signals 1770A-B and any security challenge control signals 171A-D needed by the security challenge devices 1101B-C.

FIG. 17 is a block diagram of an integrated arming switch 1456 of the antimicrobial system 1401. The arming switch 1456 can include a toggle switch, button, keypad 1211, or other interactable component to act as an inspection switch 761, and can include occupancy, audio, light, motion, ozone, or daylight sensor as a detector 47. Integrated arming switch 1456 includes a micro-control unit (MCU) 1729, drive/sense circuitry 46, detector(s) 47 (e.g., occupancy, light, or audio), switches 861, an optional integrated arming switch status indicator 1761, and an optional integrated arming switch communication interface system 1755. The switches 861 of the arming switch at least include an inspection switch 761, which sends the visual inspection signal 1770A to the disinfection light control network 7 and in particular the switching device 110. Detectors 47 can be a sensor of occupancy (e.g., infrared sensor or image sensor, such as a camera, for occupancy or motion detection), a light sensor, an audio sensor, a temperature sensor, or other environmental sensor. Drive/sense circuitry 46, such as application firmware, drives the occupancy, audio, and photo sensor hardware.

The detectors 47 are a component of the integrated arming switch room sensor 1745. The integrated arming switch room sensor 1745 may simply pass through sensory data from the detector(s) 47 to the MCU 1729, or the integrated arming switch room sensor 1745 may itself have components and complexity equal to a room sensor 45 embedded within the integrated arming switch 1456. This embedded integrated arming switch room sensor 1745 may have the MCU 629 of a room sensor, as well as a room sensor communication interface system 655. Some of the components of the embedded integrated arming switch room sensor 1745 present in a room sensor 45 may be omitted and the embedded integrated arming switch room sensor 1745 may share with the encasing integrated arming switch 1456.

The detector(s) 47 have a field of view 1499A, represented as a conical projected field with an acute end emanating from the detector(s) 47. The field of view 1499A with the conical projected field forms a cone-shaped pattern within which the detector(s) 47 sense for occupancy. This pattern is defined with a point emanating from the detector (s) 47, and extending away from the detector(s) 47 in an increasing radius. Thus, when observed from the side, the pattern has a roughly triangular shape, widening as the field of view 1499A approaches a surface. The pattern has an elliptical shape when projected on a surface such as the ground or a wall of the physical space 2. The field of view 1499A however may take on a variety of shapes depending upon the sensory technology of the detector(s) 47. For example, if the detector(s) 47 are light-based detectors, and the field of view 1499A is projected into a rectangular hallway within the physical space 2, then the field of view 1499A will project a rectangular shape, or an ovoid shape with flat sides, on surfaces from the perspective of the detector(s) 47. However, if a penetrating radio waveform is used by the detector(s) 47, then the field of view 1499A may penetrate through the walls or columns forming the rectangular hallway within the physical space 2, and the field of view 1499A will project an elliptical shape from the perspective of the detector(s) 47. Either the projected two-dimensional shape, or the three dimensional shape of the field of view 1499A may overlap partially or completely with another field of view 1499 of another detector 47. This other detector 47 may be within another room sensor 45, standalone room sensor 2145, another integrated arming switch room sensor 1745, or a different detector 47 of the same integrated arming switch room sensor 1745.

A traditional passive infrared motion sensor (PIR) detector 47 is enhanced with microphonics, or audio detector circuit, for improved reliability of motion and occupancy sensing. In other embodiments, the motion sensor detector (s) 47 may be based on ultrasonic, UWB, radar, or other motion sensing technologies known to the art.

The example inspection switch 761 of the integrated arming switch 1456 are simple pushbutton switches, but the inspection switch 761 could by any kind of user interface element; the integrated arming switches 1456A-B could require a key, or a security challenge such as a passphrase, PIN, or fingerprint scan. Additionally, an integrated arming switch 1456A can implement a different security challenge, or could implement no security challenge or key requirement at all, even if another integrated arming switch 1456B or arming switch 56A implements a security challenge or key requirement. The inspection switch 761 could also be implemented virtually, as a digital object an operator interacts with via a computing component like the touch screen device 811 of FIG. 8.

As shown, MCU 1729 includes integrated arming switch processor 1730 and integrated arming switch memory 1731 to implement the authenticated safe lockout protocol 1001, streamlined safe lockout protocol 1800, integrated arming switch control programming 1732, as well as the distributed disinfection control programming 532 an arming switch 56 would implement, described herein. The circuitry, hardware, and software of the integrated arming switch 1456 is similar to the luminaire 10 of FIG. 4A, including the line power source 101, non-line power source 102, power supply 105, power distribution 125, and the arming switch communication interface system 755. The integrated arming switch 1456 can include an integrated arming switch communication interface system 1755 like the luminaire communication interface system 155 of FIG. 4A. The non-line power source 102 may include an integrated arming switch battery 1702, which has a stored power amount 1734 indicating either a relative or absolute amount of power currently stored within the integrated arming switch battery 1702. The integrated arming switch memory 1731 also tracks a minimum power storage threshold 1733 when the non-line power source 102 is an integrated arming switch battery 1702. The minimum power storage threshold 1733 indicates a level of stored power amount 1734 below which the extended stability of the integrated arming switch 1456 (and consequently the antimicrobial system 1401) cannot be ensured. When the stored power amount 1734 is below the minimum power storage threshold 1733, then the integrated arming switch communication interface system 1755 may send a low power arming switch error message 1799 to the disinfection light control network 7. This may indicate to the switching device 110 that the disinfection lights 17 cannot be energized until the stored power amount 1734 is higher than the minimum power storage threshold 1733 of the integrated arming switch 1456, and may also indicate to an off-premises 265 device such as the cloud computing device 266 that an operator must be sent to check the integrated arming switch battery 1702.

The integrated arming switch communication interface system 1755 is able to generally transmit signals throughout the antimicrobial system 1401, and in particular sends out the visual inspection signal 1770A produced based on a second input from the operator, and sends out the room state signal 1770B produced in response to the integrated arming switch room sensor 1745 detecting occupancy of the vicinity 180 of the physical space 2 by the human 185. The visual inspection signal 1770A is treated by the members of the control group 1408 as functionally equivalent to the visual inspection signal 170B from an arming switch 56, and the room state signal 1770B is treated by the members of the control group 1408 as functionally equivalent to the room state signal 170F from a room sensor 45.

The integrated arming switch communication interface system 1755 can also include a wireless communication security challenge device 1157. The wireless communication security challenge device 1157 utilizes the one or more of the RF transceivers 156A-B for short wireless communication over a short range wireless communication network 399 to transmit a security challenge via a security challenge signal 171B to a mobile device 25. The operator then enters the security challenge input, and the mobile device 25 sends the security challenge input signal 171C to the wireless communication security challenge device 1157. The wireless communication security challenge device 1157 then validates the security challenge input from the security challenge input signal 171C, and transmits the security challenge response signal 171A to the disinfection light control network 7.

Alternatively, the integrated arming switch communication interface system 1755 may not include a wireless communication security challenge device 1157—instead, the integrated arming switch communication interface system 1755 transmits the security challenge signal 171B to the mobile device 25. Then, the mobile security challenge device 1125 determines if the security challenge input of the operator is a valid security challenge input for the security challenge, and transmits the security challenge response signal 171A into the disinfection light control network 7, possibly via the integrated arming switch communication interface system 1755. In another alternative, the integrated arming switch communication interface system 1755 transmits the security challenge signal 171B to the mobile device 25. Then, the operator inputs the security challenge input into the mobile device 25 based upon the security challenge from the security challenge signal, and the mobile device 25 transmits the security challenge input signal 171C to another security challenge device 1101 in the disinfection light control network, possibly a network security challenge device 1135 of the arming switch 56, for validation.

The integrated arming switch status indicator 1761 is a visual indicator for either the operator or other humans 185, and can operate like the pilot light status indicator of the control station 20. The integrated arming switch status indicator 1761 may display a motion status signal 1762 in the form of a light when the detector 47 of the integrated arming switch 1456 is enabled and detects occupancy of the vicinity 180 of the physical space 2 by the human 185. The integrated arming switch status indicator 1761 may also display a disinfection status signal 1763 in the form of a light when the luminaire 10A or any luminaires 10A-F in the antimicrobial system 1401 emit disinfection light 17. The status indicator may include multiple light source to indicate the motion status signal 1762 and the disinfection status signal 1763, or it may display multiple statuses via a single light source by varying the intensity and color of the light emitted by the light source. For example, the light source may emit a red light when the disinfection status signal 1763 indicates the luminaire 10A is emitting disinfection light and the motion status signal indicates no occupancy of the vicinity 180 by the human 185; may emit a green light when the disinfection status signal 1763 indicates the luminaire 10A is not emitting disinfection light and the motion status signal indicates no occupancy of the vicinity 180 by the human 185; may emit a blue light when the disinfection status signal 1763 indicates the luminaire 10A is not emitting disinfection light and the motion status signal indicates occupancy of the vicinity 180 by the human 185; and may emit a brighter flashing red light when the disinfection status signal 1763 indicates the luminaire 10A is emitting disinfection light and the motion status signal indicates occupancy of the vicinity 180 by the human 185.

The integrated arming switch 1456 provides an additional safety layer by preventing UV-C equipped light fixtures or luminaires 10A from turning ON when motion is detected. The integrated arming switch room sensor 1745 in this example is detecting motion in a horizontal view direction and overlaps detection area of the ceiling and corner mounted main motion room sensors 45B-E, and therefore prevents an inadvertent exposure of harmful UV-C light to humans 185 and animals in case of the main occupancy room sensor 45B-E failure(s).

As described herein, an antimicrobial system 1401 includes a luminaire 10A configured to emit a disinfection light 17 in an ultraviolet (UV) band for disinfecting a vicinity 180 of a physical space 2 of a target pathogen 187 that is exposed to the disinfection light 17. The UV band of the luminaire 10A can be 200 nanometers (nm) to 280 nm wavelength. The antimicrobial system 1 further includes a switching device 110 that includes a primary relay pack 111. The primary relay pack 111 includes a primary relay pack regulator 511 coupled to the luminaire 10A and configured to control power to the luminaire 10A. The primary relay pack 111 further includes a primary relay pack processor 530 coupled to the primary relay pack regulator 511 and configured to control the primary relay pack regulator 511. The primary relay pack 111 further includes a primary relay pack memory 531 accessible to the primary relay pack processor 530. The primary relay pack 111 further includes distributed disinfection control programming 532 in the primary relay pack memory 531.

Antimicrobial system 1401 further includes a control station 20 of FIG. 8 located outside the physical space 2 and coupled to the switching device 110. The control station 20 includes: (a) a disinfection initiation user interface element 862 to produce an arming initiation signal 170A based on a first input from an operator, (b) an arming completion interface user element 863 to produce an arming completion signal 170C based on a third input from the operator, and (c) a disinfection commencement user interface element 864 to produce a disinfection commencement signal 170D based on a fourth input from the operator.

The antimicrobial system 1401 further includes an integrated arming switch 1456A located inside the physical space 2. The integrated arming switch 1456A includes an integrated arming switch communication interface 1755. The integrated arming switch 1456A further includes an integrated arming switch processor 1730 coupled to the integrated arming switch communication interface 1755. The integrated arming switch 1456A further includes an integrated arming switch room sensor 1745 coupled to the integrated arming switch processor 1730. The integrated arming switch 1456A further includes an integrated arming switch memory 1731 coupled to the integrated arming switch processor 1730. The integrated arming switch 1456A further includes integrated arming switch control programming 1732 in the integrated arming switch memory 1731.

The arming switch 56A is configured to produce a visual inspection signal 170B based on a second input from the operator. The antimicrobial system 1 further includes a room sensor 45A located inside the physical space 2 and coupled to the switching device 110. The room sensor 45A is configured to produce a room state signal 170F in response to detecting occupancy of the vicinity 180 of the physical space 2 by a human 185.

Execution of the integrated arming switch control programming 1732 by the integrated arming switch processor 1730 configures the integrated arming switch 1456 to perform the following functions. First, based on a second input from the operator, produce a visual inspection signal 1770A. Second, in response to the integrated arming switch room sensor 1745 detecting occupancy of the vicinity 180 of the physical space 2 by the human 185, produce a room state signal 1770B. Third, send, via the integrated arming switch communication interface 1755, the visual inspection signal 1770A to enable the primary relay pack 111 to control power to the luminaire 10A to emit the disinfection light 17 via the primary relay pack regulator 511. Fourth, send, via the integrated arming switch communication interface 1755, the room state signal 1770B to enable the primary relay pack 111 to control power to the luminaire 10A to stop emitting the disinfection light 17 via the primary relay pack regulator 511.

In an example, the integrated arming switch room sensor 1745 includes a passive infrared motion sensor; microphonics; an audio detector circuit; an ultra-wideband radio; a RADAR antenna; a LIDAR scanner; a time-of-flight sensor; an ultrasonic sensor; a structured light sensor; a parallax sensor; or a combination thereof, as one or more detectors 47.

Additionally, execution of the integrated arming switch control programming 1732 by the integrated arming switch processor 1730 further configures the integrated arming switch 1456 to perform the following functions. First, prior to receiving the disinfection commencement signal 170D, disable the functions to produce or send the room state signal 1770B. Second, in response to receiving the disinfection commencement signal 170D, enable the functions to produce or send the room state signal 1770B.

In one example, the integrated arming switch 1456 further comprises an integrated arming switch status indicator 1761. Execution of the integrated arming switch control programming 1732 by the integrated arming switch processor 1730 further configures the integrated arming switch 1456 to perform the following functions. In response to the integrated arming switch room sensor 1745 detecting occupancy of the vicinity 180 of the physical space 2 by the human 185, produce a motion status signal 1762 via the integrated arming switch status indicator 1761.

In some examples, the integrated arming switch 1456 is powered by an integrated arming switch battery 1702. The integrated arming switch memory 1731 of the integrated arming switch 1456 stores a minimum power storage threshold 1733 for operation of the integrated arming switch 1456. Execution of the integrated arming switch control programming 1732 by the integrated arming switch processor 1730 further configures the integrated arming switch 1456 to perform the following functions. First, detect a stored power amount 1734 in the integrated arming switch battery 1702. Second, in response to the detected stored power amount 1734 in the integrated arming switch battery 1702 being less than the minimum power storage 1733 threshold, send, via the integrated arming switch communication interface 1755, a low-power arming switch error message 1799 indicating a low-power state of the integrated arming switch 1456 to enable the primary relay pack regulator 511 to power off the disinfection light source 16 to stop emitting the disinfection light 17.

Additionally, the antimicrobial system 1401 further comprises a standalone arming switch 2056 located inside the physical space 2 and coupled to the switching device 110. The standalone arming switch 2056 includes a standalone arming switch communication interface 2055. The standalone arming switch 2056 further includes a standalone arming switch processor 2030 coupled to the standalone arming switch communication interface 2055. The standalone arming switch 2056 further includes a standalone arming switch memory 2031 coupled to the standalone arming switch processor 2030. The standalone arming switch 2056 further includes standalone arming switch control programming 2032 in the standalone arming switch memory 2031. Execution of the standalone arming switch control programming 2032 by the standalone arming switch processor 2030 further configures the standalone arming switch 2056 to perform the following functions. First, produce a standalone visual inspection signal 170B based on a sixth input from the operator. Second, send, via the standalone arming switch communication interface 2055, the standalone visual inspection signal 170B to enable the primary relay pack 111 to control power to the luminaire 10A to emit the disinfection light 17 via the primary relay pack regulator 511.

As an example, the antimicrobial system 1401 further comprises a standalone room sensor 2145 located inside the physical space 2 and coupled to the switching device 110. The standalone room sensor 2145 includes a standalone room sensor communication interface 2155. The standalone room sensor 2145 further includes a standalone room sensor processor 2130 coupled to the standalone room sensor communication interface 2155. The standalone room sensor 2145 further includes a standalone room sensor memory 2131 coupled to the standalone room sensor processor 2130. The standalone room sensor 2145 further includes standalone room sensor control programming 2132 in the standalone arming switch memory 2031. Execution of the standalone room sensor control programming 2132 by the standalone room sensor processor 2130 further configures the standalone room sensor 2145 to perform the following functions. First, produce a standalone room state signal 170F in response to detecting occupancy of the vicinity 180 of the physical space 2 by the human 185. Second, send, from the standalone room sensor 2145, the standalone room state signal 170F to enable the primary relay pack 111 to control power to the luminaire 10A to stop emitting the disinfection light 17 via the primary relay pack regulator 511.

Additionally, the integrated arming switch room sensor 1745 includes a first field of view 1499A of the vicinity 180. The standalone room sensor 2145 includes a second field of view 1499B of the vicinity 180. The function of the integrated arming switch control programming 1732 to produce the room state signal 1770B further includes to produce the room state signal 1770B in response to the integrated arming switch room sensor 1745 detecting occupancy in the first field of view 1499A. The function of the standalone room sensor control programming 2132 to produce the standalone room state signal 170F further includes to produce the standalone room state signal 170F in response to the standalone room sensor 2145 detecting occupancy in the second field of view 1499B. The first field of view 1499A and the second field of view overlap 1499B.

Furthermore, execution of the integrated arming switch control programming 1732 by the integrated arming switch processor 1730 further configures the integrated arming switch 1456 to perform the following functions. First, send, via the integrated arming switch communication interface 1755, the room state signal 1770B to enable the primary relay pack 111 to control power to the luminaire 10A to stop emitting the disinfection light 17 within the vicinity 180 associated with the first field of view 1499A via the primary relay pack regulator 511. Still further, execution of the standalone room sensor control programming 2132 by the standalone room sensor processor 2130 further configures the standalone room sensor 2145 to perform the following functions. First, send, via the standalone room sensor communication interface 2155, the standalone room state signal 170F to enable the primary relay pack 111 to control power to the luminaire 10A to stop emitting the disinfection light 17 within the vicinity 180 associated with second field of view 1499B via the primary relay pack regulator 511.

In an example, the arming initiation signal 170A, the visual inspection signal 1770A, the arming completion signal 170C, the security challenge response signal 171A, and the disinfection commencement signal 170D are disinfection control signals produced in a disinfection control signal sequence, for example, successively in order. Each of the disinfection controls signals 170A-D, 171A, 1770A are switched between an on signal or an off signal by the operator to control power to the disinfection light source 16 to emit the disinfection light 17 via the primary relay pack regulator 511. In response to each of the disinfection controls signal 170A-D, 171A, 1770A being switched to the on signal by the operator within a limited time (e.g., 5 minutes), the primary relay pack regulator 511 powers on the disinfection light source 16 to emit the disinfection light 17. In response to one or more of the disinfection controls signals 170A-D, 171A, 1770A being switched to the off signal, the primary relay pack regulator 511 powers off the disinfection light source 16 to stop emitting the disinfection light 17.

In an additional example, execution of the distributed disinfection control programming 532 by the primary relay pack processor 511 further configures the primary relay pack 111 to perform the following functions. First, in response to the visual inspection signal 1770A or the room state signal 1770B, control power to the luminaire 10A to stop emitting the disinfection light 17 via the primary relay pack regulator 511. Furthermore, in a related example, the antimicrobial system 1401 includes a plurality of luminaires 10A-F, execution of the distributed disinfection control programming 532 by the primary relay pack processor 530 configures the primary relay pack 111 to perform the following functions. First, control each of the luminaires 10A-F to stop emitting the disinfection light 17 in response to the visual inspection signal 1770A or the room state signal 1770B produced by the integrated arming switch 1456 indicating to turn off the disinfection light 17.

In a different example, execution of the distributed disinfection control programming 532 by the primary relay pack processor 530 configures the primary relay pack 111 to perform the following functions. First, in response to the control station 20 producing the arming initiation signal 170A, confirm the integrated arming switch 1456 is able to generate the visual inspection signal 1770A and the room state signal 1770B.

FIG. 18 is a flowchart diagramming the streamlined safe lockout protocol 1800 of the antimicrobial system 1401. This streamlined safe lockout protocol 1800 can be designed to comply with safety regulations for UV light disinfection of a physical space 2 where human(s) 185 travel through or occupy, and prevents non-authorized personnel from activating the disinfection light source of a luminaire 10 known to be hazardous to humans 185 and animals. The streamlined safe lockout protocol 1800 can be implemented in the control station 20, integrated arming switches 1456A-B, arming switches 56A-B, or a hybrid system with identifications methods implemented across different types of control group devices 8. Any authentication method listed in the authenticated safe lockout protocol 1001, or combination of multiple authentication methods, can be implemented in any of the antimicrobial system 1401 devices. The security challenge-related steps 1025, 1030, 1035, and 1040 can be included in the streamlined safe lockout protocol 1800, but are omitted for clarity in writing.

Beginning in step 1804, the streamlined safe lockout protocol 1800 includes prior to receiving a disinfection commencement signal 170D, disabling the functions to produce or send the room state signal 1770B. This reduces extraneous processing and network traffic within the antimicrobial system 1401, because at this point in time humans 185, either operators or inhabitants, are expected within the physical space 2. Therefore, reporting occupancy is not necessary. This step and corresponding step 1817 described below are optional, however, and certain steps such as step 1815 can benefit from streamlined safe lockout protocol 1800 where the function to produce or send the room state signal 1770B are never disabled.

Next, in step 1805, in response to a control station 20 producing an arming initiation signal 170A that is ON based on a first input from an operator, tracking a visual inspection signal 1770A produced by an integrated arming switch 1456. The tracking of a visual inspection signal 1770A occurs at the primary relay pack 111, and is a tracking process, determining whether the inspection switch 761 at each integrated arming switch 1456A-B has been pressed. The primary relay pack 111 will attempt to track one visual inspection signal 1770A for each integrated arming switch 1456A-B in the antimicrobial system 1401.

Following in step 1807, based on a second input from the operator, producing a visual inspection signal 1770B. The operator inspects the physical space 2, and presses all of the inspection switches 761 of the integrated arming switches 1456A-B, such as integrated arming switch 1456A, to produce the visual inspection signal 1770A. In step 1808, the integrated arming switches begin sending, via an integrated arming switch communication interface 1755, the visual inspection signal 1770A to enable the primary relay pack 111 to control power to the luminaire 10A to emit the disinfection light 17 via the primary relay pack regulator 511. However, the primary relay pack 111 is waiting on additional inputs before the primary relay pack 111 will control power to the luminaire 10A to emit the disinfection light 17.

Moving to step 1810, the streamlined safe lockout protocol 1800 further includes determining that the tracked visual inspection signal 1770A is ON based on a second input produced by the integrated arming switch 1456A.

Continuing to step 1815, the streamlined safe lockout protocol 1800 further includes in response to determining that the tracked visual inspection signal 1770A is ON and the control station 20 subsequently producing the arming completion signal 170C that is ON based on a third input from the operator, receiving a disinfection commencement signal 170D that is ON based on a fourth input from the control station 20. After the control station 20 produces the arming completion signal 170C, the primary relay pack 111 determines the integrated arming switch 1456A produced the visual inspection signal 1770A and that the visual inspection signal 1770A is ON. The ON signal could be a formatted message, or the presence or absence of power in a communication line during a particular period of time.

After the arming completion signal 170C is produced but before the operator can trigger the arming commencement signal 170D, the streamlined safe lockout protocol 1800 implements the following steps. Checking that no room state signal 1770B is indicated as OFF by at least one integrated arming switch 1456A-B, meaning that, during the check, no human 185 is detected by the antimicrobial system 1 within the physical space 2. The OFF signal could be a formatted message, or the presence or absence of power in a communication line during a particular period of time. If even one room state signal 1770B has been indicated as OFF by at least one integrated arming switch 1456A-B, then it is possible that a human 185 is within the physical space 2, and a safe lockout cannot occur. If step 1804 has occurred, then the integrated arming switches 1456A-B are unable to send the room state signal 1770B, and so the room state signal 1770B cannot be indicated as OFF.

After checking that no room state signal 1770B of any integrated arming switch 1456A-B is set to OFF and determining that the visual inspection signal 1770A is ON, the primary relay pack 111 enables the disinfection commencement user interface element 864. An operator triggering the disinfection commencement user interface element 864 while the disinfection commencement user interface element 864 is not enabled will have no effect on the antimicrobial system 1, or will cancel the safe lockout protocol 1001.

The operator, after the disinfection commencement user interface element 864 is enabled, will perform a fourth user input into the disinfection commencement user interface element 864, in this example by inserting and turning a key. Entering this fourth input into the disinfection commencement user interface element 864 causes the control station 20 to produce the disinfection commencement signal 170D.

In step 1817, in response to receiving the disinfection commencement signal 170D, enabling the functions to produce or send the room state signal 1770B, if they were disabled in step 1804.

Following in step 1840, the streamlined safe lockout protocol 1800 further includes in response to receiving the disinfection commencement signal 170D that is ON based on the fourth input from the control station 20, enabling a primary relay pack 111 to control power to a luminaire 10A to emit disinfection light 17 via a primary relay pack regulator 511. As noted above, the fourth input from the operator can be a turn of a key. The steps 1805, 1807, 1808, 1810 1815, and 1840 are performed sequentially, and therefore the arming initiation signal 170A, the visual inspection signal 170B, the arming completion signal 170C, and the disinfection commencement signal 170D are disinfection control signals 170A-D are produced in a disinfection control signal sequence. Steps 1804 and 1817 are sequential, and step 1817 can be performed after any step between step 1805 and step 1840.

The next possible event is the detection of occupancy of the vicinity 180 of the physical space 2. In step 1845, in response to an integrated arming switch room sensor 1745 detecting occupancy of a vicinity 180 of the physical space 2 by a human 185, producing a room state signal 1770B. At almost the same time, in step 1846 in response to the integrated arming switch room sensor 1745 detecting occupancy of the vicinity 180 of the physical space 2 by the human 185, produce a motion status signal 1762 via an integrated arming switch status indicator 1761. The integrated arming switch status indicator 1761 helps an operator determine which integrated arming switch 1456 or room sensor 45 detected occupancy, and also can assist an operator in determining which vicinity 180 of the physical space 2 the occupancy was detected within. This is especially relevant when the field of view 1499A of the integrated arming switch room sensor 1745 does not cover the entire physical space 2, but rather only a portion of the full vicinity 180 of the physical space 2.

Following step 1845, the vicinity 180 of the physical space 2 is occupied, and therefore disinfection cannot continue. Therefore, in step 1850 the streamlined safe lockout protocol 1800 further includes sending, via the integrated arming switch communication interface 1755, the room state signal 1770B to enable the primary relay pack 111 to control power to the luminaire 10A to stop emitting the disinfection light 17 via the primary relay pack regulator 511. Upon receiving the room state signal 1770B while emitting the disinfection light 17, the primary relay pack 111 will control the luminaire 10A to stop emitting the disinfection light 17.

The steps 1025, 1030, and 1035 related to security challenges can also be taken in the streamlined safe lockout protocol 1800, and can occur in series at any point before step 1840. If the steps related to security challenges are taken in the streamlined safe lockout protocol 1800, then step 1840 further includes in response to receiving a security challenge response signal 171A, enabling the primary relay pack 111 to control power to the luminaire 10A to emit disinfection light via the primary relay pack regulator 511. Additionally, as in the authenticated safe lockout protocol 1001, the primary relay pack 111 may control the luminaires 10G-L to stop emitting the disinfection light 17 in response to one or more of: a visual inspection signal 170B produced by an arming switch 56A-B indicating OFF, a room state signal 170F produced by a room sensor 45M-N indicating OFF, an occupancy signal 170G produced by a occupancy or room sensor 45G-L indicating OFF or a security challenge response signal 171A produced by a security challenge device 1101 indicating OFF.

The sequence of operation of the streamlined safe lockout protocol 1800 is highly configurable, but one of many possible implementations is to enable motion detection functionality in step 1817 only after the disinfectant process is enabled and started in 1840, so the process would be disabled and power to UV-C fixtures disrupted when any motion in the treated space is detected by the integrated arming switch(es) 1456.

Figure 19:
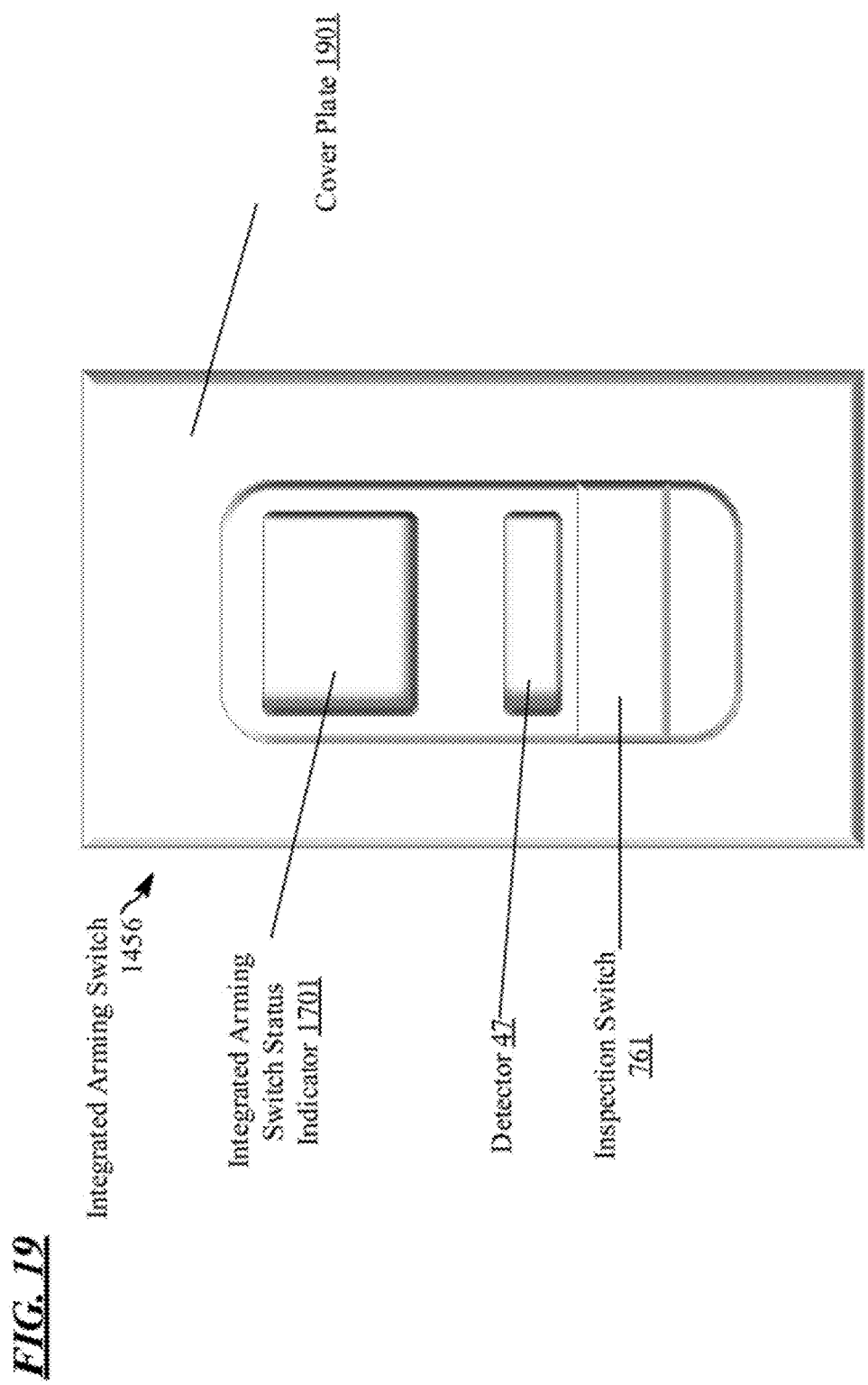
FIG. 19 is an example depiction of the front face of the integrated arming switch.

FIG. 19 is an example depiction of the front face of the integrated arming switch 1456. This depiction shows the integrated arming switch 1456 as resting in a conventional One-Gang cover plate 1901. The integrated arming switch status indicator 1701 showing the motion status signal 1762 is prominently displayed to inform operators as to whether the integrated arming switch 1456 has detected any occupancy in the physical space 2. The detector 47 itself is located below, passing sensory data to the integrated arming switch room sensor 1745 in order for the integrated arming switch room sensor 1745 to detect occupancy in the physical space 2 and send the room state signal 1770B. Below the detector 47 is the inspection switch, which the operator presses in order to provide the second input and send the visual inspection signal 1770A. However, these elements may be arranged in a number of different ways and may be designed using different shapes with different absolute and relative dimensions.

FIG. 20 is a block diagram of a standalone arming switch 2056 of the antimicrobial system 1401. This standalone arming switch 2056 is indistinguishable from the arming switch 56 of FIG. 7, except that the standalone arming switch 2056 has standalone arming switch control programming 2032, discussed in FIG. 17, to facilitate the standalone arming switch 2056 working cooperatively with the integrated arming switch 1456.

FIG. 21 is a block diagram of a standalone room sensor 2145 of the antimicrobial system 1401. This standalone room sensor 2145 is indistinguishable from the room sensor 45 of FIG. 6, except that the standalone arming switch 2056 has standalone room sensor control programming 2132, discussed in FIG. 17, to facilitate the standalone arming switch 2056 working cooperatively with the integrated arming switch 1456. This block diagram also includes the field of view 1499B of the standalone room sensor 2145, which may overlap in some instances with the field of view 1499A of the integrated arming switch 1456.

Any of the components of the antimicrobial system 1 and the antimicrobial system 1401, including integrated arming switches 1451, may be combined to perform any of the steps in the authenticated safe lockout protocol 1001 or the streamlined safe lockout protocol 1800. Responsive members of the control group 8 or 1408 will broadly not distinguish between the visual inspection signal 1770A from an integrated arming switch 1456 and the visual inspection signal 170B from an arming switch 56; likewise, responsive members of the control group 8 or 1408 will broadly not distinguish between the room state signal 1770B from the integrated arming switch 1456 and the room state signal 170F from a room sensor 45. Protocol step pairings 1005 and 1805, 1010 and 1810, 1015 and 1815, and 1040 and 1840 can be generally combined into a single step that does not distinguish between the control signals 170B,F of arming switches 56 and room sensors 45, and the corresponding integrated arming switch control signals 1770A-B of integrated arming switches 1456.

Any of the steps or functionality, e.g., of the distributed disinfection control techniques, such as authenticated safe lockout protocol 1001, streamlined safe lockout protocol 1800, integrated arming switch control programming 1732, standalone arming switch control programming 2032, standalone room sensor control programming 2132, security challenge device programming 1132, and distributed disinfection control programming 532, described herein for luminaires 10A-L, switching device 110, primary relay pack 111, safeguard relay pack 112, room sensors 45A-N, arming switches 56A-B, control station 20, gateway 220, cloud computing device 266, security challenge device 1101, integrated arming switch 1456, standalone arming switch 2056, and standalone room sensor 2145 can be embodied in programming or one more applications as described previously. This includes, for example, the authenticated safe lockout protocol 1001, the distributed disinfection control programming 532, and the security challenge device programming 1132. According to some embodiments, "function," "functions," "application," "applications," "instruction," "instructions," or "programming" are program(s) that execute functions defined in the programs. Various programming languages can be employed to create one or more of the applications, structured in a variety of manners, such as object-oriented programming languages (e.g., Objective-C, Java, or C++), procedural programming languages (e.g., C or assembly language), or firmware. In a specific example, a third party application (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating systems. In this example, the third party application can invoke API calls provided by the operating system to facilitate functionality described herein.

Hence, a machine-readable medium may take many forms of tangible storage medium. Non-volatile storage media include, for example, optical or magnetic disks, such as any of the storage devices in any computer(s) or the like, such as may be used to implement the client device, media gateway, transcoder, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims. It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," "containing," "contains,' "having," "has," "with, or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount. As used herein, the terms "substantially" or "approximately" mean the parameter value varies up to ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The invention claimed is:

1. An antimicrobial system, comprising:
a luminaire configured to emit a disinfection light in an ultraviolet (UV) band for disinfecting a vicinity of a physical space of a target pathogen that is exposed to the disinfection light,
a switching device that includes a primary relay pack;
a control station located outside the physical space and coupled to the switching device including: (a) a disinfection initiation user interface element to produce an arming initiation signal based on a first input from an operator, (b) an arming completion interface user element to produce an arming completion signal based on a third input from the operator, and (c) a disinfection commencement user interface element to produce a disinfection commencement signal based on a fourth input from the operator; and
an integrated arming switch located inside the physical space, including:
an integrated arming switch communication interface,
an integrated arming switch processor coupled to the integrated arming switch communication interface,
an integrated arming switch room sensor coupled to the integrated arming switch processor,
an integrated arming switch memory coupled to the integrated arming switch processor, and
integrated arming switch control programming in the integrated arming switch memory;
wherein execution of the integrated arming switch control programming by the integrated arming switch processor configures the integrated arming switch to perform functions, including functions to:
based on a second input from the operator, produce a visual inspection signal;
in response to the integrated arming switch room sensor detecting whether the vicinity is occupied or unoccupied, produce a room state signal;

send, via the integrated arming switch communication interface, the visual inspection signal to cause the luminaire to emit the disinfection light via the primary relay pack; and send, via the integrated arming switch communication interface, the room state signal to cause the luminaire to stop emitting the disinfection light via the primary relay pack.

2. The antimicrobial system of claim 1, wherein:
the integrated arming switch room sensor includes:
(a) a passive infrared motion sensor;
(b) microphonics;
(c) an audio detector circuit;
(d) an ultra-wideband radio;
(e) a RADAR antenna;
(f) a LIDAR scanner; or
(g) a combination thereof.

3. The antimicrobial system of claim 1, wherein:
execution of the integrated arming switch control programming by the integrated arming switch processor further configures the integrated arming switch to perform functions, including functions to:
prior to receiving the disinfection commencement signal, disable the functions to produce or send the room state signal; and
in response to receiving the disinfection commencement signal, enable the functions to produce or send the room state signal.

4. The antimicrobial system of claim 1, wherein:
the integrated arming switch further comprises an integrated arming switch status indicator; and
execution of the integrated arming switch control programming by the integrated arming switch processor further configures the integrated arming switch to perform functions, including functions to:
in response to the integrated arming switch room sensor detecting occupancy of the vicinity, produce a motion status signal via the integrated arming switch status indicator; and
in response to the luminaire emitting the disinfection light, produce a disinfection status signal via the integrated arming switch status indicator.

5. The antimicrobial system of claim 1, wherein:
the integrated arming switch is powered by an integrated arming switch battery;
the integrated arming switch memory of the integrated arming switch stores a minimum power storage threshold for operation of the integrated arming switch;
and execution of the integrated arming switch control programming by the integrated arming switch processor further configures the integrated arming switch to perform functions, including functions to:
detect a stored power amount in the integrated arming switch battery,
in response to the detected stored power amount in the integrated arming switch battery being less than the minimum power storage threshold, send, via the integrated arming switch communication interface, a low-power arming switch error message indicating a low-power state of the integrated arming switch to enable the primary relay pack to power off the disinfection light source to stop emitting the disinfection light.

6. The antimicrobial system of claim 1, further comprising:
a standalone arming switch located inside the physical space and coupled to the switching device, including:
a standalone arming switch communication interface,
a standalone arming switch processor coupled to the standalone arming switch communication interface,
a standalone arming switch memory coupled to the standalone arming switch processor, and
standalone arming switch control programming in the standalone arming switch memory;
wherein execution of the standalone arming switch control programming by the standalone arming switch processor configures the standalone arming switch to perform functions, including functions to:
produce a standalone visual inspection signal based on a sixth input from the operator; and
send, via the standalone arming switch communication interface, the standalone visual inspection signal to enable the primary relay pack to control power to the luminaire to emit the disinfection light via the primary relay pack.

7. The antimicrobial system of claim 1, further comprising:
a standalone room sensor independent from the integrated arming switch and located inside the physical space and coupled to the switching device, including:
a standalone room sensor communication interface,
a standalone room sensor processor coupled to the standalone room sensor communication interface,
a standalone room sensor memory coupled to the standalone room sensor processor, and
standalone room sensor control programming in the standalone room sensor memory;
wherein execution of the standalone room sensor control programming by the standalone room sensor processor configures the standalone room sensor to perform functions, including functions to:
produce a standalone room state signal in response to detecting occupancy of the vicinity; and
send, from the standalone room sensor, the standalone room state signal to enable the primary relay pack to control power to the luminaire to stop emitting the disinfection light via the primary relay pack.

8. The antimicrobial system of claim 7, wherein:
the integrated arming switch room sensor includes a first field of view of the vicinity;
the standalone room sensor includes a second field of view of the vicinity;
the function of the integrated arming switch control programming to produce the room state signal further includes to produce the room state signal in response to the integrated arming switch room sensor detecting occupancy in the first field of view;
the function of the standalone room sensor control programming to produce the standalone room state signal further includes to produce the standalone room state signal in response to the standalone room sensor detecting occupancy in the second field of view; and
the first field of view and the second field of view overlap.

9. The antimicrobial system of claim 8, wherein:
execution of the integrated arming switch control programming by the integrated arming switch processor further configures the integrated arming switch to perform functions, including functions to:
send, via the integrated arming switch communication interface, the room state signal to enable the primary relay pack to control power to the luminaire to stop emitting the disinfection light within the vicinity associated with the first field of view via the primary relay pack; and execution of the standalone room sensor programming by the standalone room sensor processor further configures the standalone room sensor to perform functions, including functions to:
send, via the standalone room sensor communication interface, the standalone room state signal to enable the primary relay pack to control power to the luminaire to stop emitting the disinfection light within the vicinity associated with second field of view via the primary relay pack.

10. The antimicrobial system of claim 1, wherein:
the arming initiation signal, the visual inspection signal, the arming completion signal, the security challenge signal, and the disinfection commencement signal are disinfection control signals produced in a disinfection control signal sequence.

11. The antimicrobial system of claim 10, wherein:
each of the disinfection control signals are switched between an on signal or an off signal by the operator to control power to the disinfection light source to emit the disinfection light via the primary relay pack; and
in response to each of the disinfection controls signals being switched to the on signal by the operator within a limited time, the primary relay pack powers on the disinfection light source to emit the disinfection light.

12. The antimicrobial system of claim 11, wherein:
in response to one or more of the disinfection controls signals being switched to the off signal, the primary relay pack powers off the disinfection light source to stop emitting the disinfection light.

13. The antimicrobial system of claim 1, wherein the primary relay pack further includes:
a primary relay pack regulator coupled to the luminaire and configured to control power to the luminaire,
a primary relay pack processor coupled to the primary relay pack regulator and configured to control the primary relay pack regulator,
a primary relay pack memory accessible to the primary relay pack processor, and
distributed disinfection control programming in the primary relay pack memory;
wherein execution of the distributed disinfection control programming by the primary relay pack processor configures the primary relay pack to perform functions, including functions to:
in response to the visual inspection signal or the room state signal, control power to the luminaire to stop emitting the disinfection light via the primary relay pack regulator.

14. The antimicrobial system of claim 13, further comprising a plurality of luminaires, wherein:
execution of the distributed disinfection control programming by the primary relay pack processor further configures the primary relay pack to perform functions, including functions to:
control each of the luminaires to stop emitting the disinfection light in response to the visual inspection signal or the room state signal produced by the integrated arming switch indicating to turn off the disinfection light.

15. The antimicrobial system of claim 13, wherein:
execution of the distributed control programming by the primary relay pack processor further configures the primary relay pack to perform functions, including functions to:
in response to the control station producing the arming initiation signal,
confirm the integrated arming switch is able to generate the visual inspection signal and the room state signal.

16. A method for an integrated arming switch lockout protocol, comprising:
providing a control station located outside a physical space, wherein the control station is coupled to a switching device and includes: (a) a disinfection initiation user interface element to produce an arming initiation signal based on a first input from an operator, (b) an arming completion interface user element to produce an arming completion signal based on a third input from the operator, and (c) a disinfection commencement user interface element to produce a disinfection commencement signal based on a fourth input from the operator;
based on a second input from the operator, producing a visual inspection signal;
in response to an integrated arming switch room sensor detecting whether a vicinity is occupied or unoccupied, producing a room state signal;
sending, via an integrated arming switch communication interface, the visual inspection signal configured to cause a luminaire to emit a disinfection light via a primary relay pack; and
sending, via the integrated arming switch communication interface, the room state signal configured to cause the luminaire to stop emitting the disinfection light via the primary relay pack.

17. The method of claim 16, wherein:
the integrated arming switch room sensor includes:
(a) a passive infrared motion sensor;
(b) microphonics;
(c) an audio detector circuit;
(d) an ultra-wideband radio;
(e) a RADAR antenna;
(f) a LIDAR scanner; or
(g) a combination thereof.

18. The method of claim 16, further comprising:
prior to receiving a disinfection commencement signal, disabling the functions to produce or send the room state signal; and
in response to receiving the disinfection commencement signal, enabling the functions to produce or send the room state signal.

19. The method of claim 16, further comprising:
in response to the integrated arming switch room sensor detecting occupancy of the vicinity, produce a motion status signal via an integrated arming switch status indicator.

* * * * *